US012570603B2

(12) United States Patent
Levi et al.

(10) Patent No.: US 12,570,603 B2
(45) Date of Patent: Mar. 10, 2026

(54) FABP4/5 INHIBITORS, METHODS OF USE AND METHODS OF MAKING

(71) Applicant: Novius Therapeutics, LLC, Cleveland, OH (US)

(72) Inventors: Liraz Levi, Pepper Pike, OH (US); Tej Pareek, Beachwood, OH (US); Elizabeth Meyers, Vermillion, OH (US); Seunghwan Lim, Solon, OH (US); William J. Greenlee, Teaneck, NJ (US); Seong-Jin Kim, Seocho-Gu (KR)

(73) Assignee: Celloram Inc., Cleveland, OH (US)

( * ) Notice: Subject to any disclaimer, the term of this patent is extended or adjusted under 35 U.S.C. 154(b) by 0 days.

(21) Appl. No.: 17/944,821

(22) Filed: Sep. 14, 2022

(65) Prior Publication Data

US 2023/0150931 A1 May 18, 2023

Related U.S. Application Data

(60) Provisional application No. 63/244,670, filed on Sep. 15, 2021.

(51) Int. Cl.

| | |
|---|---|
| ***C07C 323/61*** | (2006.01) |
| ***A61P 35/04*** | (2006.01) |
| ***C07C 235/74*** | (2006.01) |
| ***C07C 257/06*** | (2006.01) |
| ***C07C 311/13*** | (2006.01) |
| ***C07C 325/02*** | (2006.01) |
| ***C07D 263/44*** | (2006.01) |
| ***C07D 271/07*** | (2006.01) |
| ***C07D 285/08*** | (2006.01) |
| ***C07D 291/04*** | (2006.01) |
| ***C07D 307/24*** | (2006.01) |
| ***C07D 333/40*** | (2006.01) |

(52) U.S. Cl.

CPC ............ *C07C 323/61* (2013.01); *A61P 35/04* (2018.01); *C07C 235/74* (2013.01); *C07C 257/06* (2013.01); *C07C 311/13* (2013.01); *C07C 325/02* (2013.01); *C07D 263/44* (2013.01); *C07D 271/07* (2013.01); *C07D 285/08* (2013.01); *C07D 291/04* (2013.01); *C07D 307/24* (2013.01); *C07D 333/40* (2013.01)

(58) Field of Classification Search

CPC ... C07C 323/61; C07C 235/74; C07C 257/06; C07C 311/13; C07C 325/02; A61P 35/04; C07D 263/44; C07D 271/07; C07D 285/08; C07D 291/04; C07D 307/24; C07D 333/40

USPC .......................................................... 514/360

See application file for complete search history.

(56) References Cited

U.S. PATENT DOCUMENTS

| | | | | |
|---|---|---|---|---|
| 2,520,293 A * | 8/1950 | Weiss | C07C 323/60 548/197 |
| 3,660,408 A * | 5/1972 | Ackerman | C07D 207/452 548/545 |

FOREIGN PATENT DOCUMENTS

| | | | |
|---|---|---|---|
| EP | 3109239 A1 | 12/2016 |
| JP | S5439028 A | 3/1979 |
| WO | 2014146995 A1 | 9/2014 |
| WO | 2015065937 A1 | 5/2015 |
| WO | 2018078624 A1 | 5/2018 |

OTHER PUBLICATIONS

Gao et al., From hit to lead: Structure-based discovery of naphthalene-1-sulfonamide derivatives as potent and selective inhibitors of fatty acid binding protein 4, 2018, European Journal of Medicinal Chemistry, vol. 154, 44-59 (Year: 2018).*

Szawkalo et al., Synthesis and dynamic stereochemistry of 4-aryl-thiomorpholine-3,5-dione derivatives, 2015, Journal of Molecular Structure, 1079, 383-390 (Year: 2015).*

Cai Haiyan et al: "Discovery of highly selective inhibitors of human fatty acid binding protein 4 (FABP4) by virtual screening", Bioorganic & Medicinal Chemistry Letters, vol. 20, No. 12 , pp. 3675-3679, XP029212972, ISSN: 0960-894X, DOI: 10.1016/J.BMCL.2010.04.095, 2010.

Chang Ya-Nan et al: "Carbamylmethyl Mercaptoacetate Thioether: A Novel Scaffold for the Development of LI Metallo-[beta]-lactamase Inhibitors", ACS Medicinal Chemistry Letters, vol. 8, No. 5, Apr. 27, 2017 (Apr. 27, 2017), pp. 527-532, XP093005051, US ISSN: 1948-5875, DOI: 10.1021/acsmedchemlett.7b00058.

H. Lan et al: "Small-molecule inhibitors of FABP4/5 ameliorate dyslipidemia but not insulin resistance in mice with diet-induced obesity", Journal of Lipid Research, vol. 52, No. 4, Apr. 1, 2011 (Apr. 1, 2011), pp. 646-656, XP055226912, US ISSN: 0 022-2275, DOI: 10.1194/jlr.M012757.

Skinner G Charles: "Homeosterically Related Plant Growth Regulators. * 11 Synthesis", J. Agr. Food Chem.21, n°6, 1973, Jan. 1, 1973 (Jan. 1, 1973), pp. 1057-1060, XP093005089, Retrieved from the Internet: URL:https://pubs.acs.org/doi/abs/10.1021/jf60190a002 [retrieved on Dec. 5, 2022].

(Continued)

*Primary Examiner* — Kristin A Vajda

(74) *Attorney, Agent, or Firm* — FisherBroyles, LLP; Adam K. Whiting; Joseph Kim

(57) ABSTRACT

Disclosed herein are FABP4 and FABP5 inhibitor compounds and their use in pharmaceutical compositions for treating diseases relating to fatty acid metabolism, including cancer. Also disclosed herein are methods for preparing the disclosed compounds.

11 Claims, 25 Drawing Sheets

(56) References Cited

OTHER PUBLICATIONS

Szawkalo Joanna et al: “Synthesis and dynamic stereochemistry of 4-aryl-thiomorpholine-3,5-dione derivatives”, Journal of Molecular Structure, Elsevier Amsterdam, NL vol. 1079, Sep. 3, 2014 (Sep. 3, 2014), pp. 383-390, XP029083920 ISSN: 0022-2860, DOI: 10.1016/J.MOLSTRUC.2014.08.046.
Williams R et al: “Synthesis and SAR of a novel positive allosteric modulator (PAM) of the metabotropic glutamate receptor 4 (mGluR4)”, Bioorganic & Medicinal Chemistry Letters, Elsevier, Amsterdam NL, vol. 19, No. 17, Sep. 1, 2009 (Sep. 1, 2009), pp. 4967-4970, XP026458536, ISSN: 0960-894X [retrieved on Jul. 18, 2009].

* cited by examiner

113,

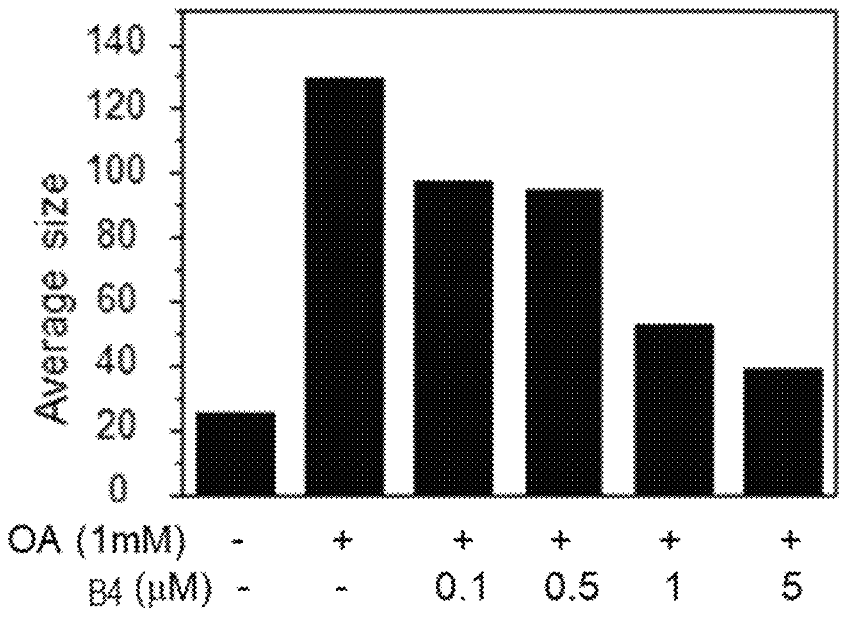
Fig. 29
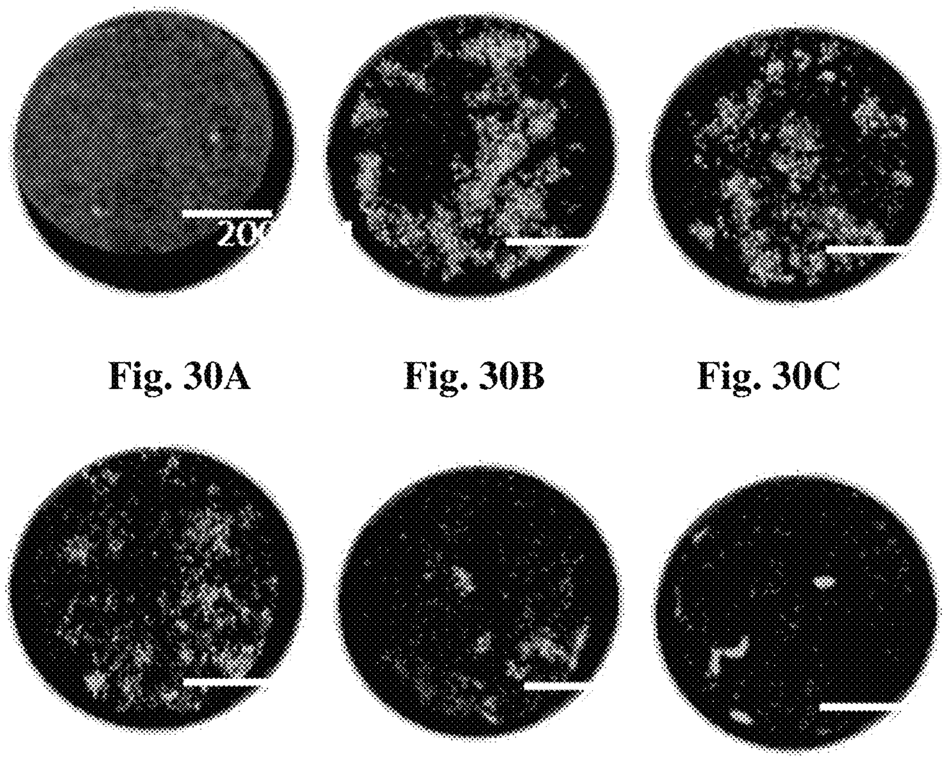
Fig. 30A Fig. 30B Fig. 30C
Fig. 30D Fig. 30E Fig. 30F

FABP4/5 INHIBITORS, METHODS OF USE AND METHODS OF MAKING

CROSS REFERENCE TO RELATED APPLICATIONS

This application claims priority of U.S. Provisional Patent Application No. 63/244,670, filed Sep. 15, 2021, the entirety of which is hereby incorporated by reference herein.

FIELD

Disclosed herein are compounds that inhibit fatty acid binding proteins 4 and 5 (FABP4 and FABP5), pharmaceutical compositions containing these inhibitor compounds, and uses of these compounds and compositions for treating diseases relating to fatty acid metabolism, including, but not limited to, cancers and metabolic disorders. Also disclosed herein are methods for preparing the disclosed FABP4/5 inhibitor compounds.

BACKGROUND

FABP4 and FABP5 are members of a family of small (~15 kDa), soluble intracellular lipid-binding proteins (iLBP) which associate with various lipid molecules such as long-chain fatty acids and thereby contribute to the trafficking of fatty acids within the cytosolic compartments of cells. FABP4 and FABP5 have no known catalytic function but facilitate the transport hydrophobic fatty acids to various destinations within the aqueous environment of the cytosol and thereby enable processes including fatty acid oxidation, membrane homeostasis, and/or nuclear signaling. In addition to playing a central role in lipid-mediated processes and metabolic and immune response pathways, it has been established that iLBPs are involved in the regulation of gene transcription by cooperating with specific ligand-activated transcription factors of the nuclear hormone receptor family (Senga, S. et al., "Fatty acid-binding protein 5 (FABP5) promotes lipolysis of lipid droplets, de novo fatty acid (FA) synthesis and activation of nuclear factor-kappa B (NF-kappaB) signaling in cancer cells," *Biochim Biophys Acta Mol Cell Biol Lipids* 1863, 1057-1067 (2018)).

FABP4 is highly expressed in adipose tissue, macrophages and endothelial cells. FABP5 is expressed in macrophages and endothelial cells, as well as in skin, adipocytes and several other tissues. Patient studies indicate that fatty acid-binding protein (FABP5) is highly upregulated in triple-negative breast cancer (TNBC) tumors and is associated with poor patient survival and the protein was reported to promote metastasis of the TNBC cell line MDA-MB-231 (Liu, R. Z. et al., "Association of FABP5 expression with poor survival in triple-negative breast cancer: implication for retinoic acid therapy," *Am J Pathol* 178, 997-1008 (2011); Powell, C. A. et al., "TRMT5 Mutations Cause a Defect in Post-transcriptional Modification of Mitochondrial tRNA Associated with Multiple Respiratory-Chain Deficiencies," *Am J Hum Genet* 97, 319-328 (2015); Apaya, M. K. et al., "Deregulating the CYP2C19/Epoxy-Eicosatrienoic Acid-Associated FABP4/FABP5 Signaling Network as a Therapeutic Approach for Metastatic Triple-Negative Breast Cancer," *Cancers* (*Basel*) 12, doi:10.3390/cancers12010199 (2020)). Additionally, FABP5 has been shown to promote resistance of prostate cancer cells to chemotherapy[4] (Carbonetti, G. et al., "Docetaxel/cabazitaxel and fatty acid binding protein 5 inhibitors produce synergistic inhibition of prostate cancer growth," *Prostate* 80, 88-98 (2020)). Both FABP5 and FABP4 has also been reported to promote proliferation and metastasis of cancer cells by altering lipid metabolism in prostate, breast, ovarian and colon cancer (Senga, S. et al., 2018, Guaita-Esteruelas, S. et al., "Adipose-Derived Fatty Acid-Binding Proteins Plasma Concentrations Are Increased in Breast Cancer Patients", *Oncologist* 22:1309-1315 (2017); Gharpure, K. M. et al., "FABP4 as a key determinant of metastatic potential of ovarian cancer", *Nature Communications* 26; 9(1):2923 (2018); Tian, Wenying et al., "FABP4 promotes invasion and metastasis of colon cancer by regulating fatty acid transport", Cancer Cell International 19; 20:512 (2020)). Studies show that cooperation between FABP5 and the pro-carcinogenic nuclear receptor PPARδ promotes survival and increased proliferation of breast cancer cells (Levi, L. et al., "Genetic ablation of the fatty acid binding protein FABP5 suppresses HER2-induced mammary tumorigenesis," *Cancer Res, doi:* 10.1158/0008-5472.CAN-13-0384 (2013); Levi, L. et al., "Saturated fatty acids regulate retinoic acid signalling and suppress tumorigenesis by targeting fatty acid-binding protein 5," *Nature communications* 6, 8794, doi:10.1038/ncomms9794 (2015)). It has been shown that genetic or chemical inhibition of FABP5 delays tumor initiation, stimulates apoptosis, and suppress the growth of cancer cells, including TNBC, that highly express the protein (Levi et al., 2013; Levi et al., (2015)). These observations point to FABP5 and FABP4 as a major pro-survival factors in multiple cancers and specifically in triple-negative breast carcinogenesis and indicate it as a therapeutic target for this disease. Like FABP5, PPARδ also displays pronounced pro-oncogenic activities and was shown to induce growth, invasiveness, and metastasis of cancer cells (Wagner, K. D. et al., "Peroxisome proliferator-activated receptor beta/delta (PPARbeta/delta) is highly expressed in liposarcoma and promotes migration and proliferation," *The Journal of pathology* 224, 575-588, doi:10.1002/path.2910 (2011); Wang, D. et al., "Crosstalk between peroxisome proliferator-activated receptor delta and VEGF stimulates cancer progression," *Proc Natl Acad Sci USA* 103, 19069-19074 (2006); Stephen, R. L. et al. "Activation of peroxisome proliferator-activated receptor delta stimulates the proliferation of human breast and prostate cancer cell lines," *Cancer Res* 64, 3162-3170 (2004)). Interestingly, PPARδ activation was shown to induce cancer stem cell (CSC) growth and to promote the development of adenosquamous carcinomas, and activation of PPARδ was reported to maintain hematopoietic stem cells population by increasing their asymmetric division (Ito, K. et al. "A PML-PPAR-delta pathway for fatty acid oxidation regulates hematopoietic stem cell maintenance," *Nat Med* 18, 1350-1358, doi:10.1038/nm.2882 (2012); Wang, X. Y. et al. "Musashil modulates mammary progenitor cell expansion through proliferin-mediated activation of the Wnt and Notch pathways," *Mol Cell Biol* 28, 3589-3599, doi:10.1128/MCB.00040-08 (2008)). The accumulated data raises the possibility that cooperation between FABP5 and PPARδ regulates self-renewal of CSCs in TNBC tumors.

Compounds that inhibit fatty acid binding proteins have been described in the art. U.S. Pat. No. 6,919,323 B2 (Sulsky et al.) describes certain pyridazinone compounds that inhibit the FABP aP2, and the use of these compounds for the treatment of type 2 diabetes and related diseases. U.S. Pat. No. 8,748,470 B2 (Lengyel et al.) describes methods for reducing or inhibiting cancer that include administering to a subject an inhibitor of FABP4 and/or FABP5, where the inhibitor is selected from a list of known compounds, including carbazole butanoic acid, aryl sulfonamide, sulfonylthiophene, 4-hydroxypyrimidine, 2,3-dimethylindole, benzoylbenzene, biphenyl-alkanoic acid, 2-oxazole-alkanoic acid, tetrahydropyrimidone, pyridone, pyrazinone, aryl carboxylic acid, tetrazole, triazolopyrimidinone, indole, or BMS480404. U.S. Pat. No. 8,815,875 B2 (Shipps, Jr. et al.) describes certain heterocyclic compounds that inhibit FABP, and the use of these compounds for the treatment of diseases or disorders including cardiovascular disease, a metabolic disorder, obesity, diabetes, dyslipidemia, and impaired glucose tolerance. U.S. Pat. No. 9,278,918 B2 (Buettelmann, et al.) describes certain urea derivative compounds that inhibit FABP4 and/or FABP5, and the use of these compounds for the treatment of diseases or disorders including type 2 diabetes, atherosclerosis, chronic kidney diseases, and cancer.

There exists a need for improved FABP4 and FABP5 inhibitor compounds, and uses of these compounds in the treatment of diseases and disorders, including cancer.

SUMMARY

The present disclosure generally relates to inhibitors of FABP4 and FABP5, and the use of these inhibitors, methods for preparing these inhibitors, and uses of these inhibitors in pharmaceutical compositions for treating diseases relating to fatty acid metabolism. This summary is intended to introduce the subject matter of the present disclosure, but does not cover each and every embodiment, combination, or variation that is contemplated and described within the present disclosure. Further embodiments are contemplated and described by the disclosure of the detailed description, drawings, and claims.

In at least one embodiment, the present disclosure provides a FABP4/5 inhibitor compound of structural formula I:

(I)

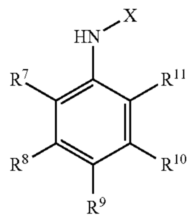

wherein $R^7$, $R^8$, $R^9$, $R^{10}$, and $R^{11}$ is each independently selected from hydrogen or a substitution for hydrogen; wherein X has the formula:

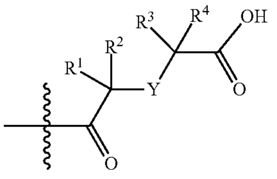

wherein Y is —$CR^5R^6$—, or a heteroatom selected from —S—, —O—, —SO—, and —$SO_2$—; and $R^5$ and $R^6$ are each independently selected from hydrogen, $C_1$-$C_4$ linear or branched alkyl, phenyl, and benzyl; wherein $R^1$, $R^2$, $R^3$ and $R^4$ is each independently selected from hydrogen, $C_1$-$C_4$ linear or branched alkyl, phenyl, and benzyl, $R^1$ and $R^4$ can be taken together to form a carbocyclic or heterocyclic ring containing from 5 to 6 atoms, or when Y is a carbon atom $R^5$ and $R^6$ can be taken together with the Y unit to form a ring having from 4 to 7 atoms; or a pharmaceutically acceptable salt thereof.

In at least one embodiment, the FABP4/5 inhibitor compounds of formula I of the present disclosure is subject to the provisos that: (i) when Y is —S—, $R^1$, $R^2$, $R^3$, $R^4$, $R^8$, and $R^{11}$ are hydrogen, and $R^7$ and $R^9$ are Cl, $R^{10}$ is not isopropoxy, benzyloxy, prop-2-yn-1-yloxy, methoxy, 2-methoxyethoxy, 2-ethoxy-2-oxoethoxy; and (ii) when Y is —O—, $R^1$, $R^2$, $R^3$, $R^4$, $R^8$, and $R^{11}$ are hydrogen, and $R^7$ and $R^9$ are Cl, $R^{10}$ is not hydrogen, or 2-methoxyethoxy.

In at least one embodiment of the FABP4/5 inhibitor compounds of formula I of the present disclosure, Y is chosen from —S— or —O— and $R^1$, $R^2$, $R^3$ and $R^4$ are each independently hydrogen or $C_1$-$C_4$ linear or branched alkyl.

In at least one embodiment of the FABP4/5 inhibitor compounds of formula I of the present disclosure, X has a formula selected from:

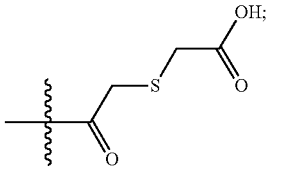

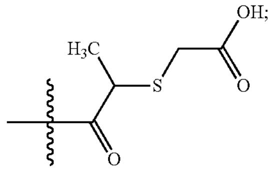

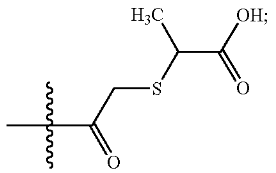

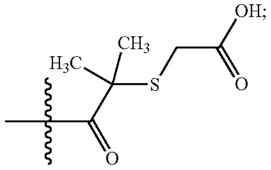

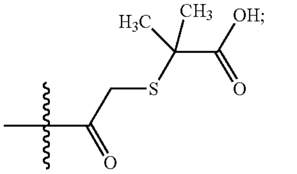

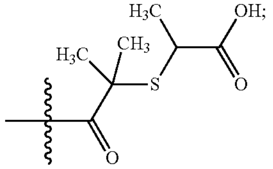

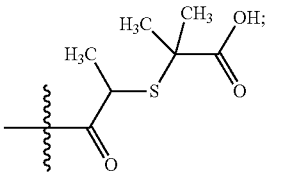

and

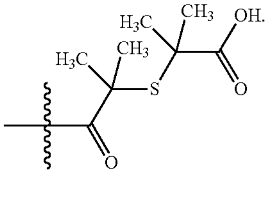

In at least one embodiment of the FABP4/5 inhibitor compounds of formula I of the present disclosure, X has a formula selected from:

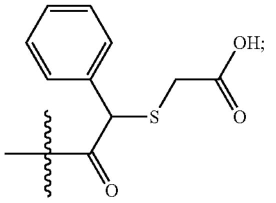

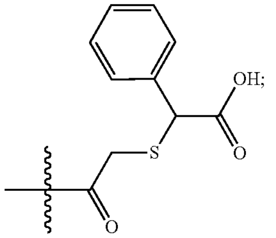

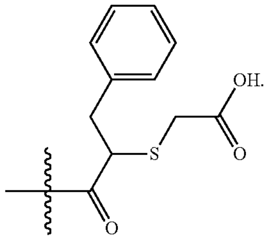

In at least one embodiment of the FABP4/5 inhibitor compounds of formula I of the present disclosure, X has a formula selected from:

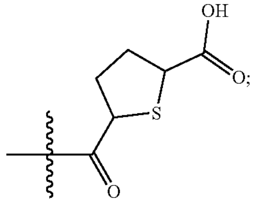

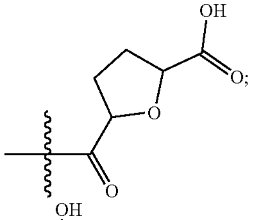

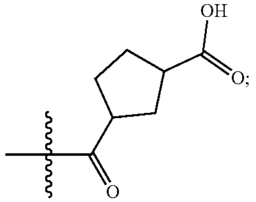

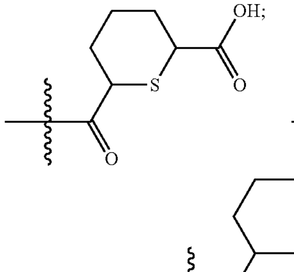

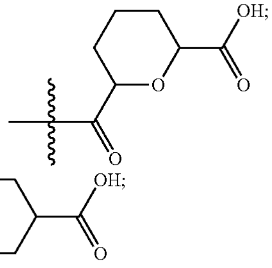

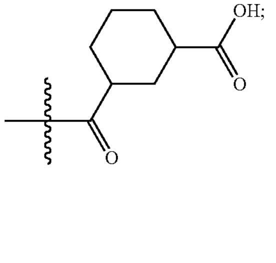

-continued

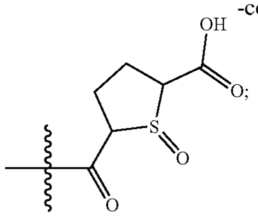

and

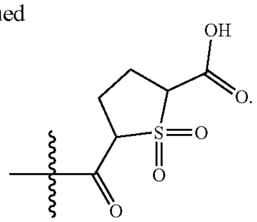

In at least one embodiment of the FABP4/5 inhibitor compounds of formula I of the present disclosure, X has a formula selected from:

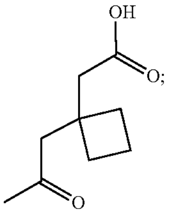

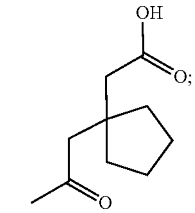

and

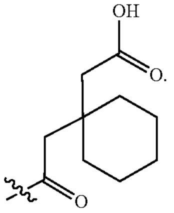

In at least one embodiment of the FABP4/5 inhibitor compounds of formula I of the present disclosure, $R^7$, $R^8$, $R^9$, $R^{10}$, and $R^{11}$ are each independently selected from: (i) hydrogen; (ii) halogen, for example, fluorine, chlorine, bromine or iodine; (iii) $C_1$-$C_4$ linear or branched, saturated or unsaturated alkyl, for example, methyl ($C_1$), ethyl ($C_2$), n-propyl ($C_3$), iso-propyl ($C_3$), cyclopropyl ($C_3$), propylen-2-yl ($C_3$), propargyl ($C_3$), n-butyl ($C_4$), iso-butyl ($C_4$), sec-butyl ($C_4$), tert-butyl ($C_4$); (iv) $C_1$-$C_4$ linear or branched, saturated or unsaturated alkoxy, for example, methoxy ($C_1$), ethoxy ($C_2$), n-propoxy ($C_3$), iso-propoxy ($C_3$), cyclopropoxy ($C_3$), propoxyen-2-oxy ($C_3$), propargoxy ($C_3$), n-butoxy ($C_4$), iso-butoxy ($C_4$), sec-butoxy ($C_4$), tert-butoxy ($C_4$); (v) $—(CR^{12a}R^{12b})_qOR^{13}$; for example, —OH, $—CH_2OH$, $—OCH_3$, $—CH_2OCH_3$, $—OCH_2CH_3$, $—CH_2OCH_2CH_3$, $—OCH_2CH_2CH_3$, and $—CH_2OCH_2CH(CH_3)_2$; (vi) $—(CR^{12a}R^{12b})_qC(O)R^{13}$; for example, $—COCH_3$, $—CH_2COCH_3$, $—OCH_2CH_3$, $—CH_2COCH_2CH_3$, $—COCH_2CH_2CH_3$, and $—CH_2COCH_2CH_2CH_3$; (vii) $—(CR^{12a}R^{12b})_qC(O)OR^{13}$; for example, $—CO_2CH_3$, $—CH_2CO_2CH_3$, $—CO_2CH_2CH_3$, $—CH_2CO_2CH_2CH_3$, $—CO_2CH_2CH_2CH_3$, and $—CH_2CO_2CH_2CH_2CH_3$; (viii) $—O(CR^{12a}R^{12b})_qC(O)OR^{13}$; for example, $—OCH_2CO_2CH_3$, $—OCO_2CH_2CH_3$, $—OCH_2CO_2CH_2CH_3$, $—OCO_2CH_2CH_2CH_3$, and $—OCH_2CO_2CH_2CH_2CH_3$; (ix) $—(CR^{12a}R^{12b})_qN(R^{13})_2$; for example, $—NH_2$, $—CH_2NH_2$, $—NHCH_3$, $—N(CH_3)_2$, $—NH(CH_2CH_3)$, $—CH_2NHCH_3$, $—CH_2N(CH_3)_2$, and $—CH_2NH(CH_2CH_3)$; (x) $—CH_mX_n$; wherein X is halogen, m is from 0 to 2, m+n=3; for example, $—CH_2F$, $—CHF_2$, $—CF_3$, $—CCl_3$, or $—CBr_3$; (xi) $—(CR^{12a}R^{12b})_qCN$; for example; —CN, $—CH_2CN$, and $—CH_2CH_2CN$; and (xii) $—(CR^{12a}R^{12b})_qNO_2$; for example; $—NO_2$, $—CH_2NO_2$, and $—CH_2CH_2NO_2$; wherein, for each of the above (i)-(xii) $R^{13}$ is independently hydrogen, $C_1$-$C_4$ linear or branched alkyl, phenyl, or benzyl; and wherein $R^{12a}$ and $R^{12b}$ are each independently hydrogen, methyl ($C_1$), or ethyl ($C_2$) and the index q is an integer from 0 to 4.

In at least one embodiment of the FABP4/5 inhibitor compounds of formula I of the present disclosure, $R^7$, $R^8$, $R^9$, $R^{10}$, and $R^{11}$ are each independently selected from hydrogen, halogen, $C_1$-$C_4$ linear, branched, or cyclic, saturated or unsaturated alkyl, phenyl, benzyl, substituted or unsubstituted $C_1$-$C_4$ linear, branched, or cyclic, saturated or unsaturated alkoxy, phenoxy, or benzyloxy.

In at least one embodiment of the FABP4/5 inhibitor compounds of formula I of the present disclosure, $R^7$, $R^8$, $R^9$, $R^{10}$, and $R^{11}$ are each independently selected from hydrogen, chloro, methoxy, ethoxy, propoxy, isopropoxy, cyclopropoxy, propargyloxy, butoxy, iso-butoxy, sec-butoxy, tert-butoxy, 2-methoxyethoxy, 2-ethoxy-2-oxoethoxy, or benzyloxy.

In at least one embodiment the present disclosure also provides a pharmaceutical composition comprising: (a) from about 10% to about 95% by weight of one or more compounds of structural formula I of the present disclosure; and (b) one or more adjunct ingredients.

In at least one embodiment the present disclosure also provides a method for treating a subject having a disease or condition affected by FABP4/5, comprising administering to a subject in need thereof a therapeutically effective amount of one or more compounds of structural formula I of the present disclosure. In at least one embodiment, the disease or condition affected by FABP4/5 is selected from: cancer (e.g., breast cancer, prostate cancer, ovarian cancer, hepatocellular cancer, multiple myeloma, neuroblastoma, lung adenocarcinoma or gastric carcinoma); metastasis of TNBC cells; free fatty acid serum levels; Type-2 diabetes; metabolic syndrome; and/or atherosclerosis.

In at least one embodiment the present disclosure also provides a process for preparing a compound of structural formula III:

(III)

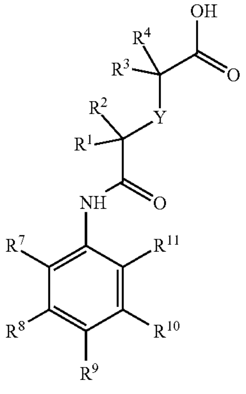

wherein Y, $R^1$, $R^2$, $R^3$, $R^4$, $R^5$, $R^6$, $R^7$, $R^8$, $R^9$, $R^{10}$, $R^{11}$, $R^{12}$, and $R^{13}$, are as defined for the compound of structural formula I (above), the process comprising: (a) combining in a solvent a compound having the formula:

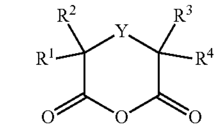

with a compound having the formula:

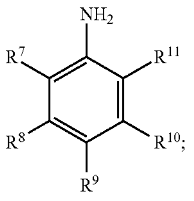

and (b) removing the solvent.

BRIEF DESCRIPTION OF THE DRAWINGS

A better understanding of the novel features and advantages of the present disclosure will be obtained by reference to the following detailed description that sets forth illustrative embodiments, in which the principles of the disclosure are utilized, and the accompanying drawings (also "Figure" and "FIG." herein), of which:

FIG. 23A and FIG. 23C are the media controls. FIG. 23A-FIG. 23D depict the amount of lipid droplets stained by Oil Red O. FIG. 23B and FIG. 23D show increased amount of stained lipid droplets when the disclosed compound B4 is added versus controls depicted in FIG. 23A and FIG. 23C.

FIG. 25A is a control sample. FIG. 25B shows the level of α-SMA following activation of the control sample. FIG. 25C discloses the effects of treatment with 0.1 μM B4, FIG. 25D discloses the effects of treatment with 0.5 μM B4, FIG. 25E discloses the effects of treatment with 1 μM B4, and FIG. 25F discloses the effects of treatment with 5 μM B4.

FIG. 27A is the control sample, FIG. 27B the oleic acid (OA) blank, FIG. 27C discloses the effects of treatment with 0.1 μM of the disclosed compound B4, FIG. 27D discloses the effects of treatment with 0.5 μM of the disclosed compound B4, FIG. 27E discloses the effects of treatment with 1 μM of the disclosed compound B4, and FIG. 27F discloses the effects of treatment with 5 μM of the disclosed compound B4.

FIG. 29 is a histogram depicting the size of the lipid droplets taken up by the cells depicted in FIG. 27A-FIG. 27F.

FIG. 30A, FIG. 30B, FIG. 30C, FIG. 30D, FIG. 30E, and FIG. 30F show that disclosed compound B4 inhibit uptake of lipids during maturation of 3T3-L1 adipocytes. Disclosed compound B4 was added to the cells at day six of the differentiation. On day 12 after administration of disclosed compound B4, the lipid droplets were stained. FIG. 30A is a control of undifferentiated pre-adipocyte cells, FIG. 30B are differentiated control cells, FIG. 30C discloses the effects of treatment with 0.1 μM of the disclosed compound B4, FIG. 30D discloses the effects of treatment with 0.5 μM of the disclosed compound B4, FIG. 30E discloses the effects of treatment with 1 μM of the disclosed compound B4, and FIG. 30F discloses the effects of treatment with 5 μM of the disclosed compound B4.

FIG. 31 shows the color intensity of the viable adipocytes over a range of B4 concentrations.

FIG. 38A: Tumor growth in MB-231 xenograft model. MB-231 cells ($5\times10^6$) were transplanted into the right flank of 7-week-old female NOD scid gamma (NSG) mice. One day later B4 treatment started by I.P. injections 5 times a week of B4 (20, or 40 mg/kg) or vehicle. Tumor growth was monitored twice a week. Mean±SD (n=5) (by unpaired t-test). FIG. 38B: Data plotted represents the volume of tumors in each mouse at the end point (day 14). Statistical significance between the control and treated mice in all experiments was evaluated using a Student's t-test.

DETAILED DESCRIPTION

Figure 1A:
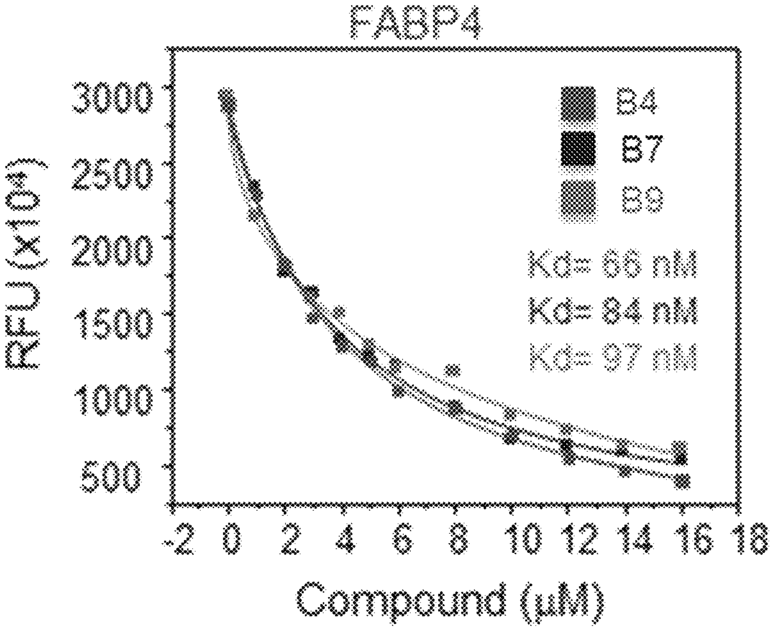
FIG. 1A and FIG. 1B depict the binding affinities of the disclosed compounds B4, B7, and B9 towards FABP4 and FABP5.

In this specification and in the claims that follow, reference will be made to a number of terms, which shall be defined to have the following meanings:

General Definitions

In this specification and in the claims that follow, reference will be made to a number of terms, which shall be defined to have the following meanings:

All percentages, ratios and proportions herein are by weight, unless otherwise specified. All temperatures are in degrees Celsius (C) unless otherwise specified.

The terms "a" and "an" are defined as one or more unless this disclosure explicitly requires otherwise.

Ranges may be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, an apparatus that "comprises," "has," "includes" or "contains" one or more elements possesses those one or more elements but is not limited to possessing only those elements. Likewise, a method that "comprises," "has," "includes" or "contains" one or more steps possesses those one or more steps but is not limited to possessing only those one or more steps.

Any embodiment of any of the disclosed methods or compositions can consist of or consist essentially of—rather than comprise/include/contain/have—any of the described steps, elements, and/or features. Thus, in any of the claims, the term "consisting of" or "consisting essentially of" can be substituted for any of the open-ended linking verbs recited above, in order to change the scope of a given claim from what it would otherwise be using the open-ended linking verb.

The feature or features of one embodiment may be applied to other embodiments, even though not described or illustrated, unless expressly prohibited by this disclosure or the nature of the embodiments.

Any embodiment of any of the disclosed compounds or methods can consist of or consist essentially of—rather than comprise/include/contain/have—any of the described steps, elements, and/or features. Thus, in any of the claims, the term "consisting of" or "consisting essentially of" can be substituted for any of the open-ended linking verbs recited above, in order to change the scope of a given claim from what it would otherwise be using the open-ended linking verb.

The feature or features of one embodiment may be applied to other embodiments, even though not described or illustrated, unless expressly prohibited by this disclosure or the nature of the embodiments.

As used herein, the term "subject" refers to a human or an animal that would benefit from being administered with the FABP4/5 inhibitor discussed in the present application, such as those suffering from, without limitation a disease affected by expression of FABP4/5, lack of control of free fatty acid serum levels, cancer, metabolic syndrome, or atherosclerosis.

As used herein, the terms "treat," "treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated.

As used herein, the terms "prevent," "preventing," "prevention," "prophylactic treatment" and the like are encompassed within the term "treating," and refer to reducing the probability of developing a disorder or condition in a subject, who does not have, but is at risk of or susceptible to developing a disorder or condition.

As used herein, "pharmaceutically acceptable" means physiologically tolerable, for either human or veterinary applications. In addition, "pharmaceutically acceptable" is meant a material that is not biologically or otherwise undesirable, i.e., the material may be administered to a subject without causing any undesirable biological effects or interacting in a deleterious manner with any of the other components of the pharmaceutical composition in which it is contained. Essentially, the pharmaceutically acceptable material is nontoxic to the recipient. The carrier would naturally be selected to minimize any degradation of the active ingredient and to minimize any adverse side effects in the subject, as would be well known to one of skill in the art. For a discussion of pharmaceutically acceptable carriers and other components of pharmaceutical compositions, see, e.g., Remington's Pharmaceutical Sciences, 18th ed., Mack Publishing Company, 1990.

"Test agents" or otherwise "test compounds" as used herein refers to an agent or compound that is to be screened in one or more of the assays described herein. Test agents include compounds of a variety of general types including, but not limited to, small organic molecules, known pharmaceuticals, polypeptides; carbohydrates such as oligosaccharides and polysaccharides; polynucleotides; lipids or phospholipids; fatty acids; steroids; or amino acid analogs. Test agents can be obtained from libraries, such as natural product libraries and combinatorial libraries. In addition, methods of automating assays are known that permit screening of several thousands of compounds in a short period.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the described invention, the preferred methods and materials are now described. All publications mentioned herein are incorporated herein by reference to disclose and describe the methods and/or materials in connection with which the publications are cited. Details associated with the embodiments described above and others are described below. The herein disclosed aryl, heterocyclic, and heteroaryl units can have one or more hydrogen atoms substituted therefor. Non-limiting examples of substitutions for hydrogen include the following:

Substituted and unsubstituted linear, branched, or cyclic alkyl units include the following non-limiting examples: methyl ($C_1$), ethyl ($C_2$), n-propyl ($C_3$), iso-propyl ($C_3$), cyclopropyl ($C_3$), n-butyl ($C_4$), sec-butyl ($C_4$), iso-butyl ($C_4$), tert-butyl ($C_4$), cyclobutyl ($C_4$), cyclopentyl ($C_5$), cyclohexyl ($C_6$), and the like; whereas substituted linear, branched, or cyclic alkyl, non-limiting examples of which includes, hydroxymethyl ($C_1$), chloromethyl ($C_1$), trifluoromethyl ($C_1$), aminomethyl ($C_1$), 1-chloroethyl ($C_2$), 2-hydroxyethyl ($C_2$), 1,2-difluoroethyl ($C_2$), 2,2,2-trifluoroethyl ($C_3$), 3-carboxypropyl ($C_3$), 2,3-dihydroxycyclobutyl ($C_4$), and the like.

Substituted and unsubstituted linear, branched, or cyclic alkenyl include, ethenyl ($C_2$), 3-propenyl ($C_3$), 1-propenyl (also 2-methylethenyl) ($C_3$), isopropenyl (also 2-methylethen-2-yl) ($C_3$), buten-4-yl ($C_4$), and the like; substituted linear or branched alkenyl, non-limiting examples of which include, 2-chloroethenyl (also 2-chlorovinyl) ($C_2$), 4-hydroxybuten-1-yl ($C_4$), 7-hydroxy-7-methyloct-4-en-2-yl ($C_9$), 7-hydroxy-7-methyloct-3,5-dien-2-yl ($C_9$), and the like.

Substituted and unsubstituted linear or branched alkynyl include, ethynyl ($C_2$), prop-2-ynyl (also propargyl) ($C_3$), propyn-1-yl ($C_3$), and 2-methyl-hex-4-yn-1-yl ($C_7$); substituted linear or branched alkynyl, non-limiting examples of which include, 5-hydroxy-5-methylhex-3-ynyl ($C_7$), 6-hydroxy-6-methylhept-3-yn-2-yl ($C_8$), 5-hydroxy-5-ethylhept-3-ynyl ($C_9$), and the like.

Substituted and unsubstituted "alkoxy" are used herein denotes a unit having the general formula $—OR^{100}$ wherein $R^{100}$ is an alkyl, alkylenyl, or alkynyl unit as defined herein above, for example, methoxy, methoxymethyl, methoxymethyl.

Substituted and unsubstituted "haloalkyl" are used herein denotes an alkyl unit having a hydrogen atom substituted by one or more halogen atoms, for example, trifluoromethyl, 1,2-dichloroethyl, and 3,3,3-trifluoropropyl.

The term "aryl" as used herein denotes cyclic organic units that comprise at least one benzene ring having a conjugated and aromatic six-membered ring, non-limiting examples of which include phenyl ($C_6$), naphthylen-1-yl ($C_{10}$), naphthylen-2-yl ($C_{10}$). Aryl rings can have one or more hydrogen atoms substituted by another organic or inorganic radical. Non-limiting examples of substituted aryl rings include: 4-fluorophenyl ($C_6$), 2-hydroxyphenyl ($C_6$), 3-methylphenyl ($C_6$), 2-amino-4-fluorophenyl ($C_6$), 2-(N,N-diethylamino)phenyl ($C_6$), 2-cyanophenyl ($C_6$), 2,6-di-tert-butylphenyl ($C_6$), 3-methoxyphenyl ($C_6$), 8-hydroxynaphthylen-2-yl ($C_{10}$), 4,5-dimethoxynaphthylen-1-yl ($C_{10}$), and 6-cyanonaphthylen-1-yl ($C_{10}$).

The term "heteroaryl" denotes an organic unit comprising a five or six membered conjugated and aromatic ring wherein at least one of the ring atoms is a heteroatom selected from nitrogen, oxygen, or sulfur. The heteroaryl rings can comprise a single ring, for example, a ring having 5 or 6 atoms wherein at least one ring atom is a heteroatom not limited to nitrogen, oxygen, or sulfur, such as a pyridine ring, a furan ring, or thiofuran ring. A "heteroaryl" can also be a fused multicyclic and heteroaromatic ring system having wherein at least one of the rings is an aromatic ring and at least one atom of the aromatic ring is a heteroatom including nitrogen, oxygen, or sulfur The following are non-limiting examples of heteroaryl rings according to the present disclosure:

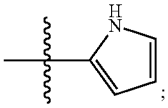
;
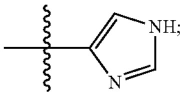
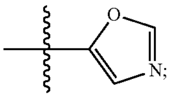
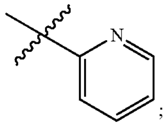
; and
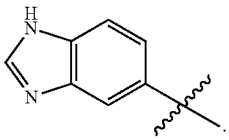
.

The term "heterocyclic" denotes a ring system having from 3 to 10 atoms wherein at least one of the ring atoms is a heteroatom not limited to nitrogen, oxygen, or sulfur. The rings can be single rings, fused rings, or bicyclic rings. Non-limiting examples of heterocyclic rings include:

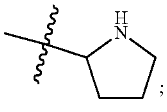
;
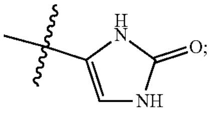
and

-continued

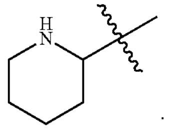

All of the aforementioned heteroaryl or heterocyclic rings can be optionally substituted with one or more substitutes for hydrogen as described herein further.

Throughout the description of the present disclosure the terms having the spelling "thiophene-2-yl and thiophene-3-yl" are used to describe the heteroaryl units having the respective formulae:

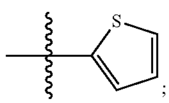
;
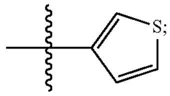
;

whereas in naming the compounds of the present disclosure, the chemical nomenclature for these moieties are typically spelled "thiophen-2-yl and thiophen-3-yl" respectively. Herein the terms "thiophene-2-yl and thiophene-3-yl" are used when describing these rings as units or moieties which make up the compounds of the present disclosure solely to make it unambiguous to the artisan of ordinary skill which rings are referred to herein.

The following are non-limiting examples of units which can substitute for hydrogen atoms on a hydrocarbyl ($C_1$-$C_{20}$ linear, branched or cyclic alkyl), aryl, heterocyclic or heteroaryl ring:

i) linear, branched, or cyclic alkyl, alkenyl, and alkynyl; for example, methyl ($C_1$), ethyl ($C_2$), n-propyl ($C_3$), iso-propyl ($C_3$), cyclopropyl ($C_3$), propylen-2-yl ($C_3$), propargyl ($C_3$), n-butyl ($C_4$), iso-butyl ($C_4$), sec-butyl ($C_4$), tert-butyl ($C_4$), cyclobutyl ($C_4$), n-pentyl ($C_5$), cyclopentyl ($C_5$), n-hexyl ($C_6$), and cyclohexyl ($C_6$);

ii) substituted or unsubstituted aryl; for example, phenyl, 2-fluorophenyl, 3-chlorophenyl, 4-methylphenyl, 2-aminophenyl, 3-hydroxyphenyl, 4-trifluoromethylphenyl, and biphenyl-4-yl;

iii) substituted or unsubstituted heterocyclic; examples of which are provided herein below;

iv) substituted or unsubstituted heteroaryl; examples of which are provided herein below;

v) alkoxy; for example, $-OH$, $-CH_2OH$, $-OCH_3$, $-CH_2OCH_3$, $-OCH_2CH_3$, $-CH_2OCH_2CH_3$, $-OCH_2CH_2CH_3$, and $-CH_2OCH_2CH_2CH_3$;

vi) keto; for example, $-COCH_3$, $-CH_2COCH_3$, $-OCH_2CH_3$, $-CH_2COCH_2CH_3$, $-COCH_2CH_2CH_3$, and $-CH_2COCH_2CH_2CH_3$;

vii) alkyl carboxyl; for example, $-CO_2CH_3$, $-CH_2CO_2CH_3$, $-CO_2CH_2CH_3$, $-CH_2CO_2CH_2CH_3$, $-CO_2CH_2CH_2CH_3$, and $-CH_2CO_2CH_2CH_2CH_3$;

viii) alkyl amido; for example, $-CONH_2$, $-CH_2CONH_2$, $-CONHCH_3$, $-CH_2CONHCH_3$, $-CON(CH_3)_2$, and $-CH_2CON(CH_3)_2$;

ix) alkyl carbamate; for example, $-OC(O)NH_2$, $-CH_2OC(O)NH_2$, $-OC(O)NHCH_3$, $-CH_2OC(O)NHCH_3$, $-OC(O)N(CH_3)_2$, and $-CH_2OC(O)N(CH_3)_2$;

x) alkylamino; for example, $-NH_2$, $-CH_2NH_2$, $-NHCH_3$, $-N(CH_3)_2$, $-NH(CH_2CH_3)$, $-CH_2NHCH_3$, $-CH_2N(CH_3)_2$, and $-CH_2NH(CH_2CH_3)$;

xi) halogen: $-F$, $-Cl$, $-Br$, and $-I$;

xii) $-CH_mX_n$; wherein X is halogen, m is from 0 to 2, m+n=3; for example, $-CH_2F$, $-CHF_2$, $-CF_3$, $-CCl_3$, or $-CBr_3$;

xiii) alkyl-cyano; for example; $-CN$, $-CH_2CN$, and $-CH_2CH_2CN$;

xiv) alkyl-nitro; for example; $-NO_2$, $-CH_2NO_2$, and $-CH_2CH_2NO_2$;

xv) alkylenesulfonyl alkyl; for example, $-SO_2H$, $-CH_2SO_2H$, $-SO_2CH_3$, $-CH_2SO_2CH_3$, $-SO_2C_6H_5$, and $-CH_2SO_2C_6H_5$; xvi) alkylene sulfonic acid; for example, $-SO_3H$, $-CH_2SO_3H$;

xvii) hydroxyl groups or thiol groups, or xviii) amino groups, monosubstituted amino, or disubstituted amino.

For the purposes of the present disclosure the terms "compound," "analog," and "composition of matter" stand equally well for the HIF-1α prolyl hydroxylase enzyme inhibitors described herein, including all enantiomeric forms, diastereomeric forms, salts, and the like, and the terms "compound," "analog," and "composition of matter" are used interchangeably throughout the present specification.

The compounds disclosed herein include all salt forms, for example, salts of both basic groups, inter alia, amines, as well as salts of acidic groups, inter alia, carboxylic acids. The following are non-limiting examples of anions that can form pharmaceutically acceptable salts with basic groups: chloride, bromide, iodide, sulfate, bisulfate, carbonate, bicarbonate, phosphate, formate, acetate, propionate, butyrate, pyruvate, lactate, oxalate, malonate, maleate, succinate, tartrate, fumarate, citrate, and the like. The following are non-limiting examples of cations that can form pharmaceutically acceptable salts of the anionic form of acidic substituent groups on the compounds described herein: sodium, lithium, potassium, calcium, magnesium, zinc, bismuth, and the like.

FABP4 and FABP5 Inhibitor Compounds

Disclosed herein are FABP4 and FABP5 inhibitor compounds having the general formula:

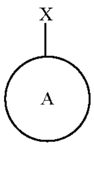

wherein the "ring A" is a substituted or unsubstituted aniline moiety (also referred to herein as "Ring A") and "X" is a moiety that participates in directing the compound into the desired active site at a desired orientation.

In at least one embodiment of the FABP4 and FABP5 inhibitor compounds, the compounds have a structural formula I:

(I)

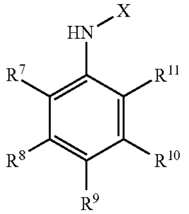

wherein $R^7$, $R^8$, $R^9$, $R^{10}$, and $R^{11}$ is each independently selected from hydrogen or a substitution for hydrogen; and wherein the moiety X has the structural formula:

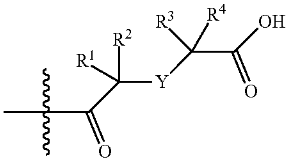

wherein Y is —$CR^5R^6$—, or a heteroatom selected from —S—, —O—, —SO—, and —$SO_2$—; and $R^5$ and $R^6$ are each independently selected from hydrogen, $C_1$-$C_4$ linear or branched alkyl, phenyl, and benzyl; and wherein $R^1$, $R^2$, $R^3$ and $R^4$ is each independently selected from hydrogen, $C_1$-$C_4$ linear or branched alkyl, phenyl, and benzyl, $R^1$ and $R^4$ can be taken together to form a carbocyclic or heterocyclic ring containing from 5 to 6 atoms, or when Y is a carbon atom $R^5$ and $R^6$ can be taken together with the Y unit to form a ring having from 4 to 7 atoms. In at least one embodiment, the compound of structural formula I includes any pharmaceutically acceptable salt thereof.

In at least one embodiment, the FABP4 and FABP5 inhibitor compounds of structural formula I (as described above and elsewhere herein) are subject to the following provisos (i) when Y is —S—, $R^1$, $R^2$, $R^3$, $R^4$, $R^8$, and $R^{11}$ are hydrogen, and $R^7$ and $R^9$ are Cl, $R^{10}$ is not isopropoxy, benzyloxy, prop-2-yn-1-yloxy, methoxy, 2-methoxyethoxy, 2-ethoxy-2-oxoethoxy; and (ii) when Y is —O—, $R^1$, $R^2$, $R^3$, $R^4$, $R^8$, and $R^{11}$ are hydrogen, and $R^7$ and $R^9$ are Cl, $R^{10}$ is not hydrogen, or 2-methoxyethoxy.

In one aspect of the disclosed FABP4 and FABP5 inhibitors the ring A aniline moiety has the formula:

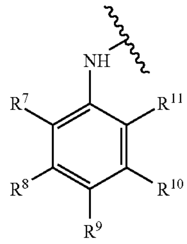

wherein $R^7$, $R^1$, $R^9$, $R^{10}$, and $R^{11}$ is each independently selected from:

b) hydrogen;

ii) halogen, for example, fluorine, chlorine, bromine or iodine;

iii) $C_1$-$C_4$ linear or branched, saturated or unsaturated alkyl, for example, methyl ($C_1$), ethyl ($C_2$), n-propyl ($C_3$), iso-propyl ($C_3$), cyclopropyl ($C_3$), 17vaporate-2-yl ($C_3$), propargyl ($C_3$), n-butyl ($C_4$), iso-butyl ($C_4$), sec-butyl ($C_4$), tert-butyl ($C_4$);

iv) $C_1$-$C_4$ linear or branched, saturated or unsaturated alkoxy, for example, methoxy ($C_1$), ethoxy ($C_2$), n-propoxy ($C_3$), iso-propoxy ($C_3$), cyclopropoxy ($C_3$), propoxyen-2-oxy ($C_3$), propargoxy ($C_3$), n-butoxy ($C_4$), iso-butoxy ($C_4$), sec-butoxy ($C_4$), tert-butoxy ($C_4$);

v) —$(CR^{12a}R^{12b})_qOR^{13}$; for example, —OH, —$CH_2OH$, —$OCH_3$, —$CH_2OCH_3$, —$OCH_2CH_3$, —$CH_2OCH_2CH_3$, —$OCH_2CH_2CH_3$, and —$CH_2OCH_2CH(CH_3)_2$;

vi) —$(CR^{12a}R^{12b})_qC(O)R^{13}$; for example, —$COCH_3$, —$CH_2COCH_3$, —$OCH_2CH_3$, —$CH_2COCH_2CH_3$, —$COCH_2CH_2CH_3$, and —$CH_2COCH_2CH_2CH_3$;

vii) —$(CR^{12a}R^{12b})_qC(O)OR^{13}$; for example, —$CO_2CH_3$, —$CH_2CO_2CH_3$, —$CO_2CH_2CH_3$, —$CH_2CO_2CH_2CH_3$, —$CO_2CH_2CH_2CH_3$, and —$CH_2CO_2CH_2CH_2CH_3$;

viii) —$O(CR^{12a}R^{12b})_qC(O)OR^{13}$; for example, —$OCH_2CO_2CH_3$, —$OCO_2CH_2CH_3$, —$OCH_2CO_2CH_2CH_3$, —$OCO_2CH_2CH_2CH_3$, and —$OCH_2CO_2CH_2CH_2CH_3$;

ix) —$(CR^{12a}R^{12b})_qN(R^{13})_2$; for example, —$NH_2$, —$CH_2NH_2$, —$NHCH_3$, —$N(CH_3)_2$, —NH $(CH_2CH_3)$, —$CH_2NHCH_3$, —$CH_2N(CH_3)_2$, and —$CH_2NH(CH_2CH_3)$;

x) —$CH_mX_n$; wherein X is halogen, m is from 0 to 2, m+n=3; for example, —$CH_2F$, —$CHF_2$, —$CF_3$, —$CCl_3$, or —$CBr_3$;

xi) —$(CR^{12a}R^{12b})_qCN$; for example; —CN, —$CH_2CN$, and —$CH_2CH_2CN$;

xii) —$(CR^{12a}R^{12b})_qNO_2$; for example; —$NO_2$, —$CH_2NO_2$, and —$CH_2CH_2NO_2$;

wherein $R^{13}$ is independently hydrogen, $C_1$-$C_4$ linear or branched alkyl, phenyl, or benzyl; $R^{12a}$ and $R^{12b}$ are each independently hydrogen, methyl ($C_1$), or ethyl ($C_2$) and the index q is an integer from 0 to 4.

In at least one aspect, the moiety X has the formula:

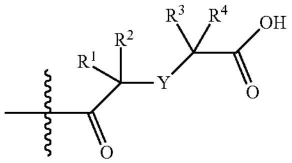

wherein Y is —$CR^5R^6$—, or a heteroatom chosen from —S—, —O—, —SO—, or —$SO_2$—; $R^5$ and $R^6$ are each independently hydrogen, $C_1$-$C_4$ linear or branched alkyl or $R^5$ and $R^6$ can be taken together to form a spirocyclic ring having from 4 to 7 carbon atoms; each $R^1$, $R^2$, $R^3$ and $R^4$ is independently hydrogen, $C_1$-$C_4$ linear or branched alkyl, or $R^1$ and $R^4$ can be taken together to form a carbocyclic or heterocyclic ring containing from 5 to 6 atoms.

In one aspect of the FABP4 and FABP5 inhibitor compounds of the present disclosure, the compounds have a structural formula II:

(II)

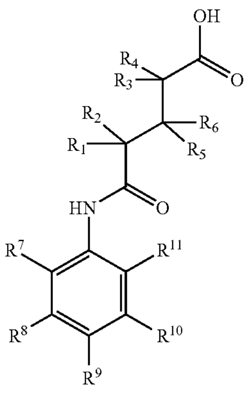

wherein $R^1$, $R^2$, $R^3$, $R^4$, $R^5$, $R^6$, $R^7$, $R^8$, $R^9$, $R^{10}$, and $R^{11}$ are defined herein above. In at least one embodiment, the compound of structural formula II includes any pharmaceutically acceptable salt thereof.

The X Moiety (or "X Unit")

The FABP4 and FABP5 inhibitor compounds of the present disclosure have an X moiety (or "X unit") of the following formula:

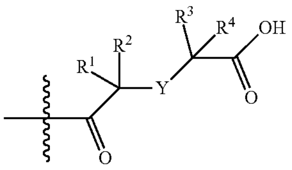

wherein Y is —$CR^5R^6$—, or a heteroatom chosen from —S—, —O—, —SO—, or —$SO_2$—; $R^5$ and $R^6$ are each independently chosen from hydrogen, $C_1$-$C_4$ linear or branched alkyl, phenyl, or benzyl; each $R^1$, $R^2$, $R^3$ and $R^4$ is independently chosen from hydrogen, $C_1$-$C_4$ linear or branched alkyl, phenyl, or benzyl, $R^1$ and $R^4$ can be taken together to form a carbocyclic or heterocyclic ring containing from 5 to 6 atoms or when Y is a carbon atom and $R^5$ and $R^6$ are taken together with the Y unit to form a ring having from 4 to 7 atoms.

In one aspect of the X moiety of the FABP4 and FABP5 inhibitor compounds Y is sulfur. In at least one embodiment of the X moiety of the compound, each of $R^1$, $R^2$, $R^3$ and $R^4$ is a hydrogen. For example, an X moiety having the formula:

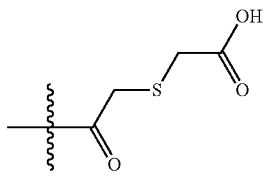 [SMILES: *C(=O)CSCC(=O)O]

Another embodiment of this aspect of the FABP4 and FABP5 inhibitor compounds of the present disclosure relates to a compound with an X moiety wherein $R^1$, $R^2$, $R^3$ and $R^4$ are each independently hydrogen or $C_1$-$C_4$ linear or branched alkyl, such as in an X moiety selected from the following non-limiting examples:

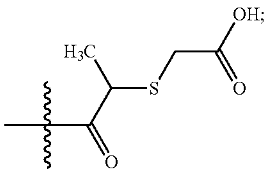

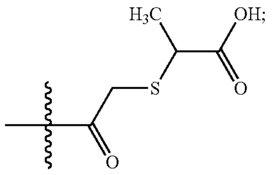

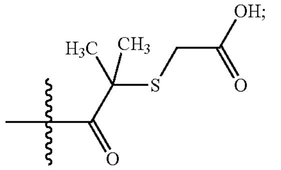

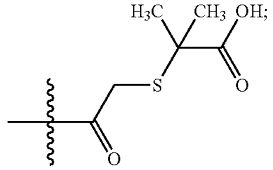

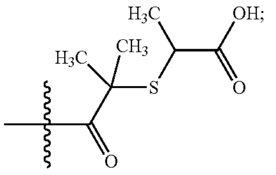

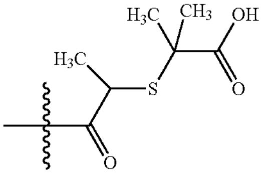

and

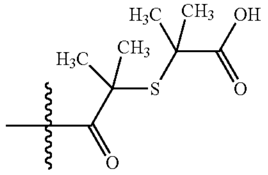

A further embodiment of this aspect of the FABP4 and FABP5 inhibitor compounds of the present disclosure relates to a compound with an X moiety wherein $R^1$, $R^2$, $R^3$ and $R^4$ are each independently hydrogen, phenyl or benzyl, such as an X moiety selected from the following non-limiting examples:

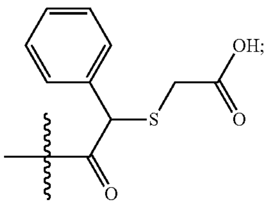

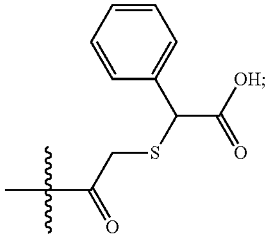

and

-continued

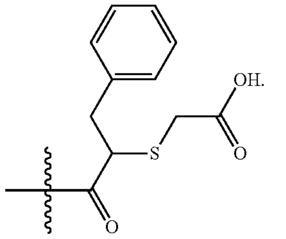

A still further embodiment of this aspect of the FABP4 and FABP5 inhibitor compounds of the present disclosure relates to a compound with an X moiety wherein $R^1$ and $R^4$ are taken together with the Y unit to form a ring having from 5 to 7 atoms; $R^2$ and $R^3$ are hydrogen, such as an X moiety selected from the following non-limiting examples:

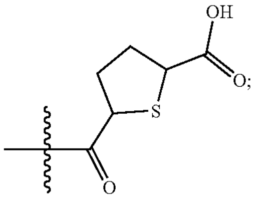

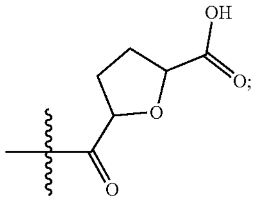

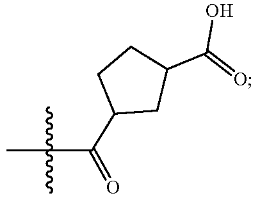

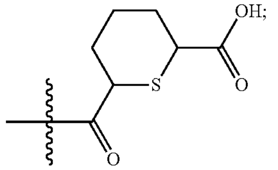

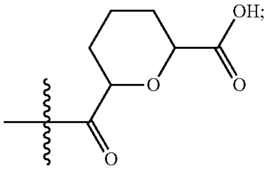

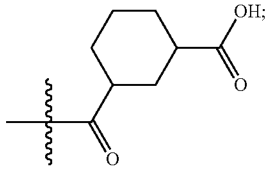

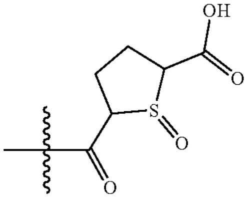

and

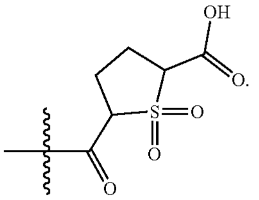

A yet another embodiment of this aspect of the FABP4 and FABP5 inhibitor compounds of the present disclosure relates to a compound with an X moiety wherein Y is a carbon atom and $R^5$ and $R^6$ are taken together with the Y unit to form a ring having from 4 to 7 atoms, such as an X moiety selected from the following non-limiting examples:

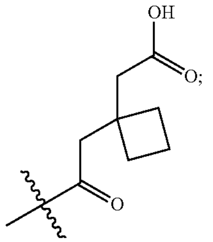

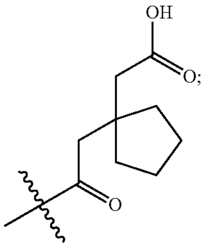

and

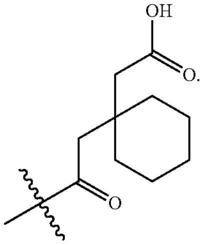

Ring A Substitutions at $R^7$, $R^8$, $R^9$, $R^{10}$, and $R^{11}$

The FABP4 and FABP5 inhibitor compounds of the present disclosure, as illustrated by the compound of structural formula I, include an aniline moiety (or Ring A) that can include substitutions for hydrogen at positions $R^7$, $R^8$, $R^9$, $R^{10}$, and $R^{11}$. In at least one aspect of the disclosed FABP4/5 inhibitor compounds one or more of the positions $R^7$, $R^8$, $R^9$, $R^{10}$, and $R^{11}$ are substituted with a halogen or a $C_1$-$C_4$ linear or branched, saturated or unsaturated alkoxy.

In one embodiment of this aspect the aniline moiety phenyl ring can comprise two halogen substitutions together with a single hydroxy or alkoxy substituent. In one embodiment of this aspect, the phenyl ring comprises a 2,3-dihalo-4-alkoxy substitution. In another embodiment of this aspect, the phenyl ring comprises a 2,4-dihalo-3-alkoxy substitution. In a further embodiment of this aspect, the phenyl ring comprises a 2,3-dihalo-5-alkoxy substitution. In a yet another embodiment of this aspect, the phenyl ring comprises a 2,3-dihalo-6-alkoxy substitution. In a yet further embodiment of this aspect, the phenyl ring comprises a 2,4-dihalo-6-alkoxy substitution. In a still another embodiment of this aspect, the phenyl ring comprises a 2,5-dihalo-4-alkoxy substitution. In a still further embodiment of this aspect, the phenyl ring comprises a 2,5-dihalo-6-alkoxy substitution. In a still yet another embodiment of this aspect, the phenyl ring comprises a 2,6-dihalo-3-alkoxy substitution. In a still yet further embodiment of this aspect, the phenyl ring comprises a 2,6-dihalo-4-alkoxy substitution.

In one non-limiting example of these embodiments of the two halogen substitutions on a the aniline moiety phenyl ring, each halogen is fluorine, for example, 2,3-difluoro-4-alkoxyphenyl, 2,4-difluoro-3-alkoxyphenyl, 2,3-difluoro-5-alkoxyphenyl, 2,3-difluoro-6-alkoxyphenyl, 2,4-difluoro-6-alkoxyphenyl, 2,5-difluoro-4-alkoxyphenyl, 2,5-difluoro-6-alkoxyphenyl, 2,6-difluoro-3-alkoxyphenyl, and 2,6-difluoro-4-alkoxyphenyl. In another non-limiting example of this embodiment each halogen is chlorine, for example, 2,3-dichloro-4-alkoxyphenyl, 2,4-dichloro-3-alkoxyphenyl, 2,3-dichloro-5-alkoxyphenyl, 2,3-dichloro-6-alkoxyphenyl, 2,4-dichloro-6-alkoxyphenyl, 2,5-dichloro-4-alkoxyphenyl, 2,5-dichloro-6-alkoxyphenyl, 2,6-dichloro-3-alkoxyphenyl, and 2,6-dichloro-4-alkoxyphenyl.

In a further non-limiting example of this embodiment each halogen is bromine, for example, 2,3-dibromo-4-alkoxyphenyl, 2,4-dibromo-3-alkoxyphenyl, 2,3-dibromo-5-alkoxyphenyl, 2,3-dibromo-6-alkoxyphenyl, 2,4-dibromo-6-alkoxyphenyl, 2,5-dibromo-4-alkoxyphenyl, 2,5-dibromo-6-alkoxyphenyl, 2,6-dibromo-3-alkoxyphenyl, and 2,6-dibromo-4-alkoxyphenyl.

In a yet another non-limiting example of this embodiment each halogen is iodine, for example, 2,3-diiodo-4-alkoxyphenyl, 2,4-diiodo-3-alkoxyphenyl, 2,3-diiodo-5-alkoxyphenyl, 2,3-diiodo-6-alkoxyphenyl, 2,4-diiodo-6-alkoxyphenyl, 2,5-diiodo-4-alkoxyphenyl, 2,5-diiodo-6-alkoxyphenyl, 2,6-diiodo-3-alkoxyphenyl, and 2,6-diiodo-4-alkoxyphenyl.

In one embodiment of the disclosed di-halo-alkoxyphenyl FABP4/5 inhibitors the alkoxy units are chosen from methoxy, ethoxy, propoxy, iso-propoxy, cyclopropoxy, butoxy, iso-butoxy, sec-butoxy, and propargyloxy.

Non-limiting examples of this embodiment each alkoxy is methoxy, for example, 2,3-dihalo-4-methoxyphenyl, 2,4-dihalo-3-methoxyphenyl, 2,3-dihalo-5-methoxyphenyl, 2,3-dihalo-6-methoxyphenyl, 2,4-dihalo-6-methoxyphenyl, 2,5-dihalo-4-methoxyphenyl, 2,5-dihalo-6-methoxyphenyl, 2,6-dihalo-3-methoxyphenyl, and 2,6-dihalo-4-methoxyphenyl.

In further non-limiting examples of this embodiment each alkoxy is ethoxy, for example, 2,3-dihalo-4-ethoxyphenyl, 2,4-dihalo-3-ethoxyphenyl, 2,3-dihalo-5-ethoxyphenyl, 2,3-dihalo-6-ethoxyphenyl, 2,4-dihalo-6-ethoxyphenyl, 2,5-dihalo-4-ethoxyphenyl, 2,5-dihalo-6-ethoxyphenyl, 2,6-dihalo-3-ethoxyphenyl, and 2,6-dihalo-4-ethoxyphenyl.

In yet further non-limiting examples of this embodiment each alkoxy is propoxy, for example, 2,3-dihalo-4-propoxyphenyl, 2,4-dihalo-3-propoxyphenyl, 2,3-dihalo-5-propoxyphenyl, 2,3-dihalo-6-propoxyphenyl, 2,4-dihalo-6-propoxyphenyl, 2,5-dihalo-4-propoxyphenyl, 2,5-dihalo-6-propoxyphenyl, 2,6-dihalo-3-propoxyphenyl, and 2,6-dihalo-4-propoxyphenyl.

In still yet further non-limiting example of this embodiment each alkoxy is iso-propoxy, for example, 2,3-dihalo-4-iso-propoxyphenyl, 2,4-dihalo-3-iso-propoxyphenyl, 2,3-dihalo-5-iso-propoxyphenyl, 2,3-dihalo-6-iso-propoxyphenyl, 2,4-dihalo-6-iso-propoxyphenyl, 2,5-dihalo-4-iso-propoxyphenyl, 2,5-dihalo-6-iso-propoxyphenyl, 2,6-dihalo-3-iso-propoxyphenyl, and 2,6-dihalo-4-iso-propoxyphenyl.

In yet still further non-limiting example of this embodiment each alkoxy is cyclopropoxy, for example, 2,3-dihalo-4-cyclopropoxyphenyl, 2,4-dihalo-3-cyclopropoxyphenyl, 2,3-dihalo-5-cyclopropoxyphenyl, 2,3-dihalo-6-cyclopropoxyphenyl, 2,4-dihalo-6-cyclopropoxyphenyl, 2,5-dihalo-4-cyclopropoxyphenyl, 2,5-dihalo-6-cyclopropoxyphenyl, 2,6-dihalo-3-cyclopropoxyphenyl, and 2,6-dihalo-4-cyclopropoxyphenyl.

In still yet another non-limiting example of this embodiment each alkoxy is butoxy, for example, 2,3-dihalo-4-butoxyphenyl, 2,4-dihalo-3-butoxyphenyl, 2,3-dihalo-5-butoxyphenyl, 2,3-dihalo-6-butoxyphenyl, 2,4-dihalo-6-butoxyphenyl, 2,5-dihalo-4-butoxyphenyl, 2,5-dihalo-6-butoxyphenyl, 2,6-dihalo-3-butoxyphenyl, and 2,6-dihalo-4-butoxyphenyl.

In a yet further non-limiting example of this embodiment each alkoxy is iso-butoxy, for example, 2,3-dihalo-4-iso-butoxyphenyl, 2,4-dihalo-3-iso-butoxyphenyl, 2,3-dihalo-5-iso-butoxyphenyl, 2,3-dihalo-6-iso-butoxyphenyl, 2,4-dihalo-6-iso-butoxyphenyl, 2,5-dihalo-4-iso-butoxyphenyl, 2,5-dihalo-6-iso-butoxyphenyl, 2,6-dihalo-3-iso-butoxyphenyl, and 2,6-dihalo-4-iso-butoxyphenyl.

In a further non-limiting example of this embodiment each alkoxy is sec-butoxy, for example, 2,3-dihalo-4-sec-butoxyphenyl, 2,4-dihalo-3-sec-butoxyphenyl, 2,3-dihalo-5-sec-butoxyphenyl, 2,3-dihalo-6-sec-butoxyphenyl, 2,4-dihalo-6-sec-butoxyphenyl, 2,5-dihalo-4-sec-butoxyphenyl, 2,5-dihalo-6-sec-butoxyphenyl, 2,6-dihalo-3-sec-butoxyphenyl, and 2,6-dihalo-4-sec-butoxyphenyl.

In one non-limiting example of this embodiment each alkoxy is tert-butoxy, for example, 2,3-dihalo-4-tert-butoxyphenyl, 2,4-dihalo-3-tert-butoxyphenyl, 2,3-dihalo-5-tert-butoxyphenyl, 2,3-dihalo-6-tert-butoxyphenyl, 2,4-dihalo-6-tert-butoxyphenyl, 2,5-dihalo-4-tert-butoxyphenyl, 2,5-dihalo-6-tert-butoxyphenyl, 2,6-dihalo-3-tert-butoxyphenyl, and 2,6-dihalo-4-tert-butoxyphenyl.

Non-limiting examples of the independent $R^7$, $R^1$, $R^9$, $R^{10}$, and $R^{11}$ phenyl ring position substitutions include: 2,4-dichloro-5-methoxyphenyl, 2,4-dichloro-5-ethoxyphenyl, 2,4-dichloro-5-propoxyphenyl, 2,4-dichloro-5-iso-propoxy-phenyl, 2,4-dichloro-5-cyclopropoxyphenyl, 2,4-dichloro-5-butoxyphenyl, 2,4-dichloro-5-iso-butoxyoxyphenyl, 2,4-dichloro-5-sec-butoxyphenyl, and 2,4-dichloro-5-tert-butoxyphenyl.

A further aspect of the disclosed FABP4 and FABP5 inhibitor compounds relates to the aniline A ring moieties wherein the phenyl ring is di-substituted with halogen, for example, two positions selected from the independent $R^7$, $R^8$, $R^9$, $R^{10}$, and $R^{11}$ are halogen. For example, 2,3-dihalophenyl, 2,4-dihalophenyl, 2,5-dihalophenyl, 2,6-dihalophenyl, 3,4-di-halophenyl and 3,5-dihalophenyl.

One embodiment of the di-halogen substituted phenyl ring moieties include: 2,3-difluorophenyl, 2,4-difluorophenyl, 2,5-difluorophenyl, 2,6-difluorophenyl, 4,4-difluorophenyl, and 3,5-difluorophenyl. In another embodiment the di-halogen substituted phenyl compounds include 2,3-dichlorophenyl, 2,4-dichlorophenyl, 2,5-dichlorophenyl, 2,6-dichlorophenyl, 4,4-dichlorophenyl, and 3,5-dichlorophenyl. In a further embodiment the di-halogen substituted phenyl ring moieties include: 2,3-dibromophenyl, 2,4-dibromophenyl, 2,5-dibromophenyl, 2,6-dibromophenyl, 4,4-dibromophenyl, and 3,5-dibromophenyl. In a still further embodiment, the di-halogen substituted phenyl ring moieties include 2,3-diiodophenyl, 2,4-diiodophenyl, 2,5-diiodophenyl, 2,6-diiodophenyl, 4,4-diiodophenyl, and 3,5-diiodophenyl In addition, the halogen substitutions can be any combination of halogens, for example, 2-chloro-3-bromophenyl, 2-fluoro-4-chlorophenyl, 3-iodo-5-bromophenyl and the like.

In another category of the FABP4 and FABP5 inhibitor compounds of the present disclosure, the $R^7$, $R^8$, $R^9$, $R^{10}$, and $R^{11}$ phenyl ring position substitutions are independently chosen from amino, linear or branched $C_1$-$C_4$ mono- and di-alkylamino or alkyl amino i.e., —$NH_2$, —$CH_2NH_2$, —$CH_2CH_2NH_2$, —$NHCH_3$, —$CH_2N(CH_3)_2$, and the like), carboxy or $C_1$-$C_4$ alkylcarboxy (i.e., —$CO_2H$, —$CH_2CO_2H$, —$CH_2CH_2CO_2H$ and the like), cyano or alkyl cyano (i.e., —CN, —$CH_2CN$, —$CH_2CH_2CN$ and the like), nitro or alkyl nitro (I.e., —$NO_2$, —$CH_2NO_2$, —$CH_2CH_2NO_2$ and the like), or haloalkyl —$CH_2F$, —$CHF_2$, —$CF_3$, —$CCl_3$, —$CBr_3$ and the like.

As noted above, and elsewhere herein, the FABP4 and FABP5 inhibitor compounds of the present disclosure, such as the compound of structural formula I, can further include the pharmaceutically acceptable salts of the compounds. Non-limiting examples of such pharmaceutically acceptable salts of the compounds can include, but are not limited to, mineral or organic acid salts of basic residues such as amines, alkylamines, or dialkylamines; alkali or organic salts of acidic residues such as carboxylic acids; and the like.

In typical embodiments, the salts are conventional nontoxic pharmaceutically acceptable salts including the quaternary ammonium salts of the parent compound formed, and non-toxic inorganic or organic acids. Non-limiting examples of salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

In at least one embodiment, the present disclosure provides FABP4 and FABP5 inhibitor compounds of Category I, which have a structural formula III:

(III)

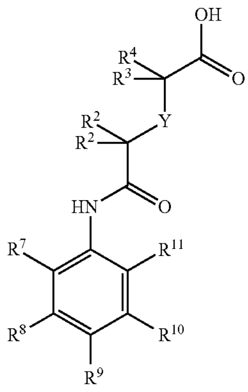

wherein Y is a heteroatom chosen from —S— or —O—, each of $R^1$, $R^2$, $R^3$ and $R^4$ is hydrogen and each of $R^7$, $R^8$, $R^9$, $R^{10}$, and $R^{11}$ is independently hydrogen or a substitution thereof for hydrogen. In at least one embodiment, the compound of structural formula III includes any pharmaceutically acceptable salt thereof.

In at least one embodiment, the FABP4 and FABP5 inhibitor compounds of structural formula III (as described above and elsewhere herein) are subject to the following provisos: (i) when Y is —S—, $R^1$, $R^2$, $R^3$, $R^4$, $R^8$, and $R^{11}$ are hydrogen, and $R^7$ and $R^9$ are Cl, $R^{10}$ is not isopropoxy, benzyloxy, prop-2-yn-1-yloxy, methoxy, 2-methoxyethoxy, 2-ethoxy-2-oxoethoxy; and (ii) when Y is —O—, $R^1$, $R^2$, $R^3$, $R^4$, $R^8$, and $R^{11}$ are hydrogen, and $R^7$ and $R^9$ are Cl, $R^{10}$ is not hydrogen, or 2-methoxyethoxy.

In one aspect, the Category I FABP4/5 inhibitor compound has the structural formula IIIa:

(IIIa)

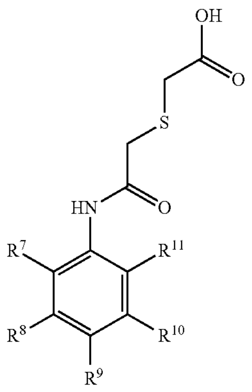

wherein each of $R^7$, $R^8$, $R^9$, $R^{10}$, and $R^{11}$ is independently chosen from hydrogen, halogen, or linear, branched, saturated or unsaturated $C_1$-$C_4$ alkyloxy, phenoxy or benzyloxy. In at least one embodiment, the compound of structural formula IIIa includes any pharmaceutically acceptable salt thereof.

In at least one embodiment, the FABP4 and FABP5 inhibitor compounds of structural formula IIIa (as described above and elsewhere herein) are subject to the proviso that when $R^1$, $R^2$, $R^3$, $R^4$, $R^8$, and $R^{11}$ are hydrogen, and $R^7$ and $R^9$ are Cl, $R^{10}$ is not isopropoxy, benzyloxy, prop-2-yn-1-yloxy, methoxy, 2-methoxyethoxy, 2-ethoxy-2-oxoethoxy.

Specific non-limiting examples of Category I compounds of structural formula IIIa defined by different phenyl ring A moiety position substitutions for hydrogen include the compounds (1)-(112) as described in Table 1 (below).

TABLE 1

| Cmpd. No. | Ring A moiety |
|---|---|
| 1 | 2-chlorophenyl |
| 2 | 3-chlorophenyl |
| 3 | 4-chlorophenyl |
| 4 | 2,3-dichlorophenyl |
| 5 | 2,4-dichlorophenyl |
| 6 | 2,5-dichlorophenyl |
| 7 | 2,6-dichlorophenyl |
| 8 | 3,4-dichlorophenyl |
| 9 | 3,5-dichlorophenyl |
| 10 | 2,3,4-trichlorophenyl |
| 11 | 2,3,5-trichlorophenyl |
| 12 | 2,3,6-trichlorophenyl |
| 13 | 3,4,5-trichlorophenyl |
| 14 | 2-chloro-3-methoxyphenyl |
| 15 | 2-chloro-4-methoxyphenyl |
| 16 | 2-chloro-5-methoxyphenyl |
| 17 | 2-chloro-6-methoxyphenyl |
| 18 | 3-chloro-2-methoxyphenyl |
| 19 | 3-chloro-4-methoxyphenyl |
| 20 | 3-chloro-5-methoxyphenyl |
| 21 | 4-chloro-2-methoxyphenyl |
| 22 | 4-chloro-3-methoxyphenyl |
| 23 | 2,3-dichloro-4-methoxyphenyl |
| 24 | 2,4-dichloro-3-methoxyphenyl |
| 25 | 2,4-dichloro-5-methoxyphenyl |
| 26 | 2,4-dichloro-6-methoxyphenyl |
| 27 | 2,5-dichloro-3-methoxyphenyl |
| 28 | 2,5-dichloro-4-methoxyphenyl |
| 29 | 2-chloro-3-ethoxyphenyl |
| 30 | 2-chloro-4-ethoxyphenyl |

TABLE 1-continued

| Cmpd. No. | Ring A moiety |
|---|---|
| 31 | 2-chloro-5-ethoxyphenyl |
| 32 | 2-chloro-6-ethoxyphenyl |
| 33 | 3-chloro-2-ethoxyphenyl |
| 34 | 3-chloro-4-ethoxyphenyl |
| 34 | 3-chloro-5-ethoxyphenyl |
| 36 | 4-chloro-2-ethoxyphenyl |
| 37 | 4-chloro-3-ethoxyphenyl |
| 38 | 2,3-dichloro-4-ethoxyphenyl |
| 39 | 2,4-dichloro-3-ethoxyphenyl |
| 40 | 2,4-dichloro-5-ethoxyphenyl |
| 41 | 2,4-dichloro-6-ethoxyphenyl |
| 42 | 2,5-dichloro-3-ethoxyphenyl |
| 43 | 2,5-dichloro-4-ethoxyphenyl |
| 44 | 2-chloro-3-ethoxyphenyl |
| 45 | 2-chloro-4-ethoxyphenyl |
| 46 | 2-chloro-5-ethoxyphenyl |
| 47 | 2-chloro-6-ethoxyphenyl |
| 48 | 3-chloro-2-ethoxyphenyl |
| 49 | 3-chloro-4-ethoxyphenyl |
| 50 | 3-chloro-5-ethoxyphenyl |
| 51 | 4-chloro-2-ethoxyphenyl |
| 52 | 4-chloro-3-ethoxyphenyl |
| 53 | 2,3-dichloro-4-ethoxyphenyl |
| 54 | 2,4-dichloro-3-ethoxyphenyl |
| 55 | 2,4-dichloro-5-ethoxyphenyl |
| 56 | 2,4-dichloro-6-ethoxyphenyl |
| 57 | 2,5-dichloro-3-ethoxyphenyl |
| 58 | 2,5-dichloro-4-ethoxyphenyl |
| 59 | 2-chloro-3-propoxyphenyl |
| 60 | 2-chloro-4-propoxyphenyl |
| 61 | 2-chloro-5-propoxyphenyl |
| 62 | 2-chloro-6-propoxyphenyl |
| 63 | 3-chloro-2-propoxyphenyl |
| 64 | 3-chloro-4-propoxyphenyl |
| 65 | 3-chloro-5-propoxyphenyl |
| 66 | 4-chloro-2-propoxyphenyl |
| 67 | 4-chloro-3-propoxyphenyl |
| 68 | 2,3-dichloro-4-propoxyphenyl |
| 69 | 2,4-dichloro-3-propoxyphenyl |
| 70 | 2,4-dichloro-5-propoxyphenyl |
| 71 | 2,4-dichloro-6-propoxyphenyl |
| 72 | 2,5-dichloro-3-propoxyphenyl |
| 73 | 2,5-dichloro-4-propoxyphenyl |
| 74 | 2-chloro-3-iso-propoxyphenyl |
| 75 | 2-chloro-4-iso-propoxyphenyl |
| 76 | 2-chloro-5-iso-propoxyphenyl |
| 77 | 2-chloro-6-iso-propoxyphenyl |
| 78 | 3-chloro-2-iso-propoxyphenyl |
| 79 | 3-chloro-4-iso-propoxyphenyl |
| 80 | 3-chloro-5-iso-propoxyphenyl |
| 81 | 4-chloro-2-iso-propoxyphenyl |
| 82 | 4-chloro-3-iso-propoxyphenyl |
| 83 | 2,3-dichloro-4-iso-propoxyphenyl |
| 84 | 2,4-dichloro-3-iso-propoxyphenyl |
| 85 | 2,4-dichloro-5-iso-propoxyphenyl |
| 86 | 2,4-dichloro-6-iso-propoxyphenyl |
| 87 | 2,5-dichloro-3-iso-propoxyphenyl |
| 88 | 2,5-dichloro-4-iso-propoxyphenyl |
| 89 | 2-chloro-3-tert-butoxyphenyl |
| 90 | 2-chloro-4-tert-butoxyphenyl |
| 91 | 2-chloro-5-tert-butoxyphenyl |
| 92 | 2-chloro-6-tert-butoxyphenyl |
| 93 | 3-chloro-2-tert-butoxyphenyl |
| 94 | 3-chloro-4-tert-butoxyphenyl |
| 95 | 3-chloro-5-tert-butoxyphenyl |
| 96 | 4-chloro-2-tert-butoxyphenyl |
| 97 | 4-chloro-3-tert-butoxyphenyl |
| 98 | 2,3-dichloro-4-tert-butoxyphenyl |
| 99 | 2,4-dichloro-3-tert-butoxyphenyl |
| 100 | 2,4-dichloro-5-tert-butoxyphenyl |
| 101 | 2,4-dichloro-6-tert-butoxyphenyl |
| 102 | 2,5-dichloro-3-tert-butoxyphenyl |
| 103 | 2,5-dichloro-4-tert-butoxyphenyl |
| 104 | 2,3-dichloro-4-propargyloxyphenyl |
| 105 | 2,4-dichloro-3-propargyloxyphenyl |
| 106 | 2,4-dichloro-5-propargyloxyphenyl |
| 107 | 2,4-dichloro-6-propargyloxyphenyl |

TABLE 1-continued

| Cmpd. No. | Ring A moiety |
|---|---|
| 108 | 2,5-dichloro-3-propargyloxyphenyl |
| 109 | 2,5-dichloro-4-propargyloxyphenyl |
| 110 | 2,3-dichloro-4-propargyloxyphenyl |
| 111 | 2,4-dichloro-3-propargyloxyphenyl |
| 112 | 2,4-dichloro-5-propargyloxyphenyl |

The following are non-limiting examples of compounds of structural formula IIIa according to this aspect of Category I of the disclosed FABP4/5 inhibitors:

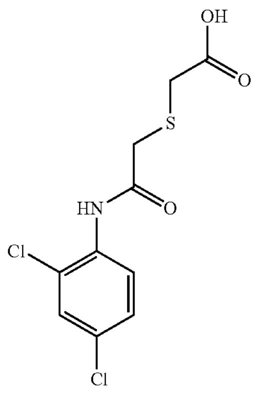 [SMILES: O=C(O)CSCC(=O)Nc1ccc(Cl)cc1Cl]

2-((2-((2,4-dichlorophenyl)amino)-2-oxoethyl)thio)acetic acid;

B7

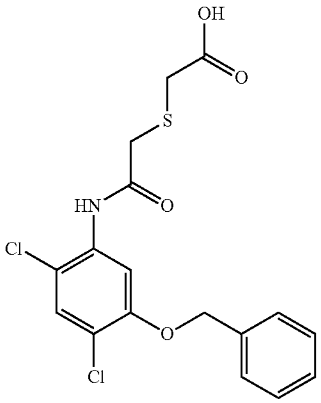

2-((2-((5-(benzyloxy)-2,4-dichlorophenyl)amino)-2-oxoethyl)thio)acetic acid CAS number (339014-97-0);

B9

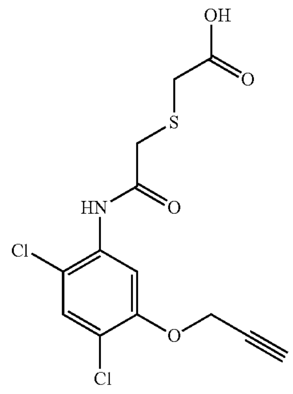

2-((2-((2,4-dichloro-5-(prop-2-yn-1-yloxy)phenyl)amino)-2-oxoethyl)thio)acetic acid CAS number (339099-42-2);

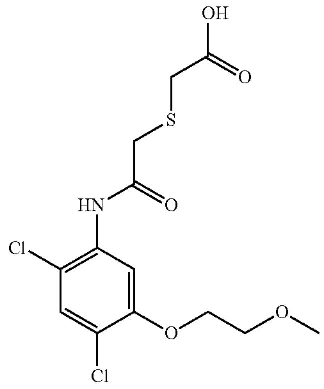 [SMILES: COCCOc1cc(NC(=O)CSCC(=O)O)c(Cl)cc1Cl]

2-((2-((2,4-dichloro-5-(2-methoxyethoxy)phenyl)amino)-2-oxoethyl)thio)acetic acid CAS number (339014-95-8);

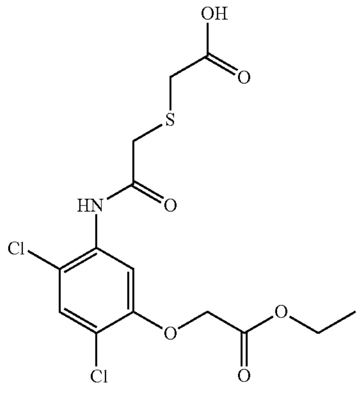 [SMILES: CCOC(=O)COc1cc(NC(=O)CSCC(=O)O)c(Cl)cc1Cl]

2-((2-((2,4-dichloro-5-(2-ethoxy-2-oxoethoxy)phenyl)amino)-2-oxoethyl)thio)acetic acid CAS number (339014-99-2);

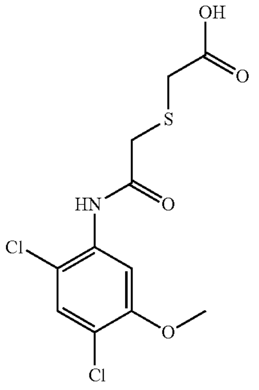 [SMILES: COc1cc(NC(=O)CSCC(=O)O)c(Cl)cc1Cl]

2-((2-((2,4-dichloro-5-methoxyphenyl)amino)-2-oxoethyl)thio)acetic acid;

B4

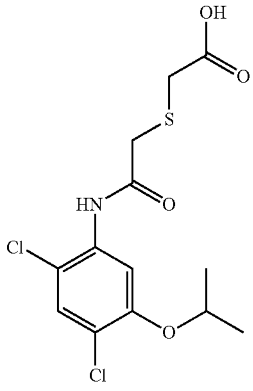

2-((2-((2,4-dichloro-5-isopropoxyphenyl)amino)-2-oxoethyl)thio)acetic acid;

B120

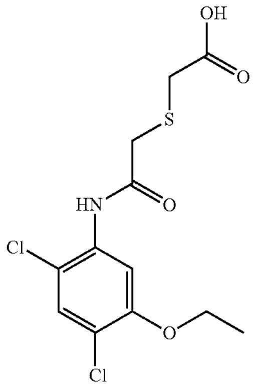

2-((2-((2,4-dichloro-5-ethoxyphenyl)amino)-2-oxoethyl)thio)acetic acid;

B121

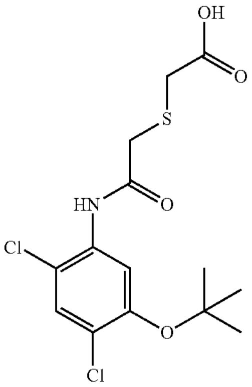

2-((2-((5-(tert-butoxy)-2,4-dichlorophenyl)amino)-2-oxoethyl)thio)acetic acid;

B122

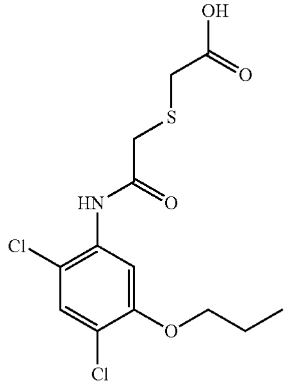

2-((2-((2,4-dichloro-5-propoxyphenyl)amino)-2-oxoethyl)thio)acetic acid;

B123

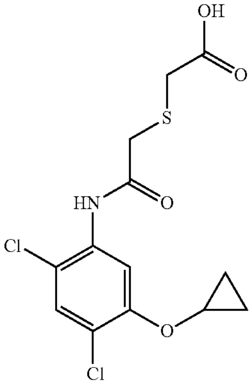

2-((2-((2,4-dichloro-5-cyclopropoxyphenyl)amino)-2-oxoethyl)thio)acetic acid; and

B124

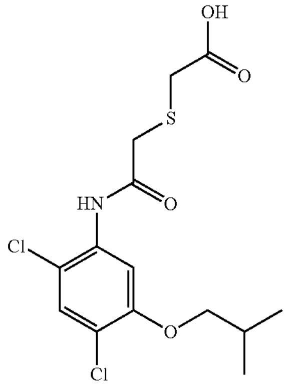

2-((2-((2,4-dichloro-5-isobutoxyphenyl)amino)-2-oxoethyl)thio)acetic acid.

In at least one embodiment, the FABP4 and FABP5 inhibitor compounds of structural formula IIIa (as described above and elsewhere herein) are subject to the proviso that the compound is not a compound selected from: 2-((2-((2,4-dichloro-5-isopropoxyphenyl)amino)-2-oxoethyl)thio)acetic acid; 2-((2-((5-(benzyloxy)-2,4-dichlorophenyl)amino)-2-oxoethyl)thio)acetic acid; 2-((2-((2,4-dichloro-5-(prop-2-yn-1-yloxy)phenyl)amino)-2-oxoethyl)thio)acetic acid; 2-((2-((2,4-dichloro-5-(2-methoxyethoxy)phenyl)amino)-2-oxoethyl)thio)acetic acid; 2-((2-((2,4-dichloro-5-(2-ethoxy-2-oxoethoxy)phenyl)amino)-2-oxoethyl)thio)acetic acid; and 2-((2-((2,4-dichloro-5-methoxyphenyl)amino)-2-oxoethyl)thio)acetic acid.

In another aspect, the Category I FABP4/5 inhibitor compounds of the present disclosure are compounds of structural formula IIIb:

(IIIb)

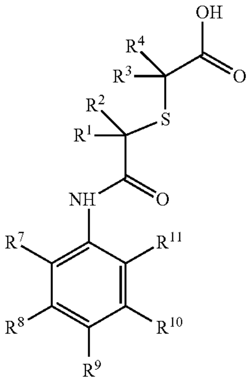

wherein each of $R^1$, $R^2$, $R^3$, and $R^4$ are chosen from hydrogen or linear or branched $C_1$-$C_4$ alkyl, at least one of $R^1$, $R^2$, $R^3$, and $R^4$ is not hydrogen; and wherein each of $R^7$, $R^8$, $R^9$, $R^{10}$, and $R^{11}$ is independently chosen from hydrogen, halogen, or linear, branched, saturated or unsaturated $C_1$-$C_4$ alkyloxy, phenoxy, and benzyloxy. In at least one embodiment, the compound of structural formula IIIb includes any pharmaceutically acceptable salt thereof.

Specific non-limiting examples of Category I compounds of structural formula IIIb as defined by ring A moiety position substitutions for hydrogen and specific substitutions at $R^1$, $R^2$, $R^3$, and $R^4$ include the compounds (113)-(184) as described in Table 2 (below).

TABLE 2

| Cmpd. No. | Ring A moiety | $R^1$ | $R^2$ | $R^3$ | $R^4$ |
|---|---|---|---|---|---|
| 113 | 2,4-dichloro-5-methoxyphenyl | H | $CH_3$ | H | H |
| 114 | 2,5-dichloro-3-methoxyphenyl | H | $CH_3$ | H | H |
| 115 | 2,5-dichloro-4-methoxyphenyl | H | $CH_3$ | H | H |
| 116 | 2,4-dichloro-5-ethoxyphenyl | H | $CH_3$ | H | H |
| 117 | 2,5-dichloro-3-ethoxyphenyl | H | $CH_3$ | H | H |
| 118 | 2,5-dichloro-4-ethoxyphenyl | H | $CH_3$ | H | H |
| 119 | 2,4-dichloro-5-propoxyphenyl | H | $CH_3$ | H | H |
| 120 | 2,5-dichloro-3-propoxyphenyl | H | $CH_3$ | H | H |
| 121 | 2,5-dichloro-4-propoxyphenyl | H | $CH_3$ | H | H |
| 122 | 2,4-dichloro-5-iso-propoxyphenyl | H | $CH_3$ | H | H |
| 123 | 2,5-dichloro-3-iso-propoxyphenyl | H | $CH_3$ | H | H |
| 124 | 2,5-dichloro-4-iso-propoxyphenyl | H | $CH_3$ | H | H |
| 125 | 2,4-dichloro-5-butoxyphenyl | H | $CH_3$ | H | H |
| 126 | 2,5-dichloro-3-butoxyphenyl | H | $CH_3$ | H | H |
| 127 | 2,5-dichloro-4-butoxyphenyl | H | $CH_3$ | H | H |
| 128 | 2,4-dichloro-5-iso-butoxyphenyl | H | $CH_3$ | H | H |
| 129 | 2,5-dichloro-3-iso-butoxyphenyl | H | $CH_3$ | H | H |
| 130 | 2,5-dichloro-4-iso-butoxyphenyl | H | $CH_3$ | H | H |
| 131 | 2,4-dichloro-5-tert-butoxyphenyl | H | $CH_3$ | H | H |
| 132 | 2,5-dichloro-3-tert-butoxyphenyl | H | $CH_3$ | H | H |
| 133 | 2,5-dichloro-4-tert-butoxyphenyl | H | $CH_3$ | H | H |
| 134 | 2,4-dichloro-5-propargyloxyphenyl | H | $CH_3$ | H | H |
| 135 | 2,5-dichloro-3-propargyloxyphenyl | H | $CH_3$ | H | H |
| 136 | 2,5-dichloro-4-propargyloxyphenyl | H | $CH_3$ | H | H |
| 137 | 2,4-dichloro-5-methoxyphenyl | H | H | H | $CH_3$ |
| 138 | 2,5-dichloro-3-methoxyphenyl | H | H | H | $CH_3$ |
| 139 | 2,5-dichloro-4-methoxyphenyl | H | H | H | $CH_3$ |
| 140 | 2,4-dichloro-5-ethoxyphenyl | H | H | H | $CH_3$ |
| 141 | 2,5-dichloro-3-ethoxyphenyl | H | H | H | $CH_3$ |
| 142 | 2,5-dichloro-4-ethoxyphenyl | H | H | H | $CH_3$ |
| 143 | 2,4-dichloro-5-propoxyphenyl | H | H | H | $CH_3$ |
| 144 | 2,5-dichloro-3-propoxyphenyl | H | H | H | $CH_3$ |
| 145 | 2,5-dichloro-4-propoxyphenyl | H | H | H | $CH_3$ |
| 146 | 2,4-dichloro-5-iso-propoxyphenyl | H | H | H | $CH_3$ |
| 147 | 2,5-dichloro-3-iso-propoxyphenyl | H | H | H | $CH_3$ |
| 148 | 2,5-dichloro-4-iso-propoxyphenyl | H | H | H | $CH_3$ |
| 149 | 2,4-dichloro-5-butoxyphenyl | H | H | H | $CH_3$ |
| 150 | 2,5-dichloro-3-butoxyphenyl | H | H | H | $CH_3$ |
| 151 | 2,5-dichloro-4-butoxyphenyl | H | H | H | $CH_3$ |
| 152 | 2,4-dichloro-5-iso-butoxyphenyl | H | H | H | $CH_3$ |
| 153 | 2,5-dichloro-3-iso-butoxyphenyl | H | H | H | $CH_3$ |
| 154 | 2,5-dichloro-4-iso-butoxyphenyl | H | H | H | $CH_3$ |
| 155 | 2,4-dichloro-5-tert-butoxyphenyl | H | H | H | $CH_3$ |
| 156 | 2,5-dichloro-3-tert-butoxyphenyl | H | H | H | $CH_3$ |
| 157 | 2,5-dichloro-4-tert-butoxyphenyl | H | H | H | $CH_3$ |
| 158 | 2,4-dichloro-5-propargyloxyphenyl | H | H | H | $CH_3$ |
| 159 | 2,5-dichloro-3-propargyloxyphenyl | H | H | H | $CH_3$ |
| 160 | 2,5-dichloro-4-propargyloxyphenyl | H | H | H | $CH_3$ |
| 161 | 2,4-dichloro-5-methoxyphenyl | H | $CH_3$ | H | $CH_3$ |
| 162 | 2,5-dichloro-3-methoxyphenyl | H | $CH_3$ | H | $CH_3$ |
| 163 | 2,5-dichloro-4-methoxyphenyl | H | $CH_3$ | H | $CH_3$ |
| 164 | 2,4-dichloro-5-ethoxyphenyl | H | $CH_3$ | H | $CH_3$ |
| 165 | 2,5-dichloro-3-ethoxyphenyl | H | $CH_3$ | H | $CH_3$ |
| 166 | 2,5-dichloro-4-ethoxyphenyl | H | $CH_3$ | H | $CH_3$ |
| 167 | 2,4-dichloro-5-propoxyphenyl | H | $CH_3$ | H | $CH_3$ |
| 168 | 2,5-dichloro-3-propoxyphenyl | H | $CH_3$ | H | $CH_3$ |
| 169 | 2,5-dichloro-4-propoxyphenyl | H | $CH_3$ | H | $CH_3$ |
| 170 | 2,4-dichloro-5-iso-propoxyphenyl | H | $CH_3$ | H | $CH_3$ |
| 171 | 2,5-dichloro-3-iso-propoxyphenyl | H | $CH_3$ | H | $CH_3$ |
| 172 | 2,5-dichloro-4-iso-propoxyphenyl | H | $CH_3$ | H | $CH_3$ |
| 173 | 2,4-dichloro-5-butoxyphenyl | H | $CH_3$ | H | $CH_3$ |
| 174 | 2,5-dichloro-3-butoxyphenyl | H | $CH_3$ | H | $CH_3$ |
| 175 | 2,5-dichloro-4-butoxyphenyl | H | $CH_3$ | H | $CH_3$ |
| 176 | 2,4-dichloro-5-iso-butoxyphenyl | H | $CH_3$ | H | $CH_3$ |
| 177 | 2,5-dichloro-3-iso-butoxyphenyl | H | $CH_3$ | H | $CH_3$ |
| 178 | 2,5-dichloro-4-iso-butoxyphenyl | H | $CH_3$ | H | $CH_3$ |
| 179 | 2,4-dichloro-5-tert-butoxyphenyl | H | $CH_3$ | H | $CH_3$ |
| 180 | 2,5-dichloro-3-tert-butoxyphenyl | H | $CH_3$ | H | $CH_3$ |
| 181 | 2,5-dichloro-4-tert-butoxyphenyl | H | $CH_3$ | H | $CH_3$ |
| 182 | 2,4-dichloro-5-propargyloxyphenyl | H | $CH_3$ | H | $CH_3$ |
| 183 | 2,5-dichloro-3-propargyloxyphenyl | H | $CH_3$ | H | $CH_3$ |
| 184 | 2,5-dichloro-4-propargyloxyphenyl | H | $CH_3$ | H | $CH_3$ |

The following are non-limiting examples of compounds of structural formula IIIb according to this aspect of Category I of the disclosed FABP4/5 inhibitors:

B102

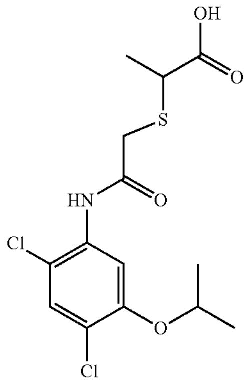

2-((2-((2,4-dichloro-5-isopropoxyphenyl)amino)-2-oxoethyl)thio)propanoic acid;

B104

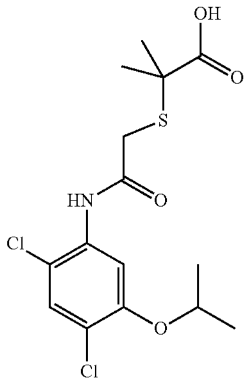

2-((2-((2,4-dichloro-5-isopropoxyphenyl)amino)-2-oxoethyl)thio)-2-methylpropanoic acid; and

B106

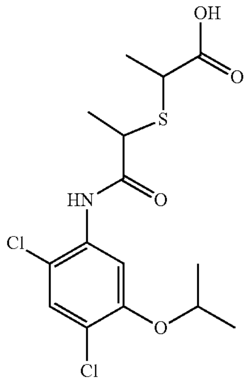

2-((1-((2,4-dichloro-5-isopropoxyphenyl)amino)-1-oxopropan-2-yl)thio)propanoic acid.

Another aspect of Category I relates to FABP4/5 inhibitors of structural formula IIIc:

(IIIc)

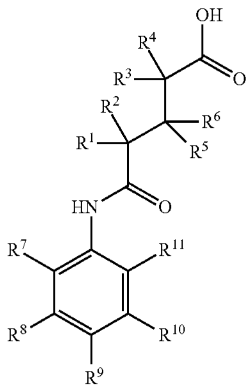

wherein each of $R^1$, $R^2$, $R^3$, $R^4$, $R^5$, and $R^6$ are chosen from hydrogen or linear or branched $C_1$-$C_4$ alkyl, $R^5$ and $R^6$ can be taken together to form a ring having from 4 to 7 carbon atoms; each of $R^7$, $R^8$, $R^9$, $R^{10}$, and $R^{11}$ is independently chosen from hydrogen, halogen, or linear, branched, saturated or unsaturated $C_1$-$C_4$ alkyloxy, phenoxy or benzyloxy. In at least one embodiment, the compound of structural formula IIIc includes any pharmaceutically acceptable salt thereof.

Specific non-limiting examples of compounds of formula IIIc according to this aspect of Category I include the compounds (185)-(256) as described in Table 3 (below).

TABLE 3

| Cmpd. No. | A Ring moiety | $R^1$ | $R^2$ | $R^3$ | $R^4$ | $R^5$ | $R^6$ |
|---|---|---|---|---|---|---|---|
| 185 | 2,4-dichloro-5-methoxyphenyl | H | H | H | H | $CH_3$ | H |
| 186 | 2,5-dichloro-3-methoxyphenyl | H | H | H | H | $CH_3$ | H |
| 187 | 2,5-dichloro-4-methoxyphenyl | H | H | H | H | $CH_3$ | H |
| 188 | 2,4-dichloro-5-ethoxyphenyl | H | H | H | H | $CH_3$ | H |
| 189 | 2,5-dichloro-3-ethoxyphenyl | H | H | H | H | $CH_3$ | H |
| 190 | 2,5-dichloro-4-ethoxyphenyl | H | H | H | H | $CH_3$ | H |
| 191 | 2,4-dichloro-5-propoxyphenyl | H | H | H | H | $CH_3$ | H |
| 192 | 2,5-dichloro-3-propoxyphenyl | H | H | H | H | $CH_3$ | H |
| 193 | 2,5-dichloro-4-propoxyphenyl | H | H | H | H | $CH_3$ | H |
| 194 | 2,4-dichloro-5-iso-propoxyphenyl | H | H | H | H | $CH_3$ | H |
| 195 | 2,5-dichloro-3-iso-propoxyphenyl | H | H | H | H | $CH_3$ | H |
| 196 | 2,5-dichloro-4-iso-propoxyphenyl | H | H | H | H | $CH_3$ | H |
| 197 | 2,4-dichloro-5-butoxyphenyl | H | H | H | H | $CH_3$ | H |
| 198 | 2,5-dichloro-3-butoxyphenyl | H | H | H | H | $CH_3$ | H |
| 199 | 2,5-dichloro-4-butoxyphenyl | H | H | H | H | $CH_3$ | H |
| 200 | 2,4-dichloro-5-iso-butoxyphenyl | H | H | H | H | $CH_3$ | H |
| 201 | 2,5-dichloro-3-iso-butoxyphenyl | H | H | H | H | $CH_3$ | H |
| 202 | 2,5-dichloro-4-iso-butoxyphenyl | H | H | H | H | $CH_3$ | H |
| 203 | 2,4-dichloro-5-tert-butoxyphenyl | H | H | H | H | $CH_3$ | H |
| 204 | 2,5-dichloro-3-tert-butoxyphenyl | H | H | H | H | $CH_3$ | H |
| 205 | 2,5-dichloro-4-tert-butoxyphenyl | H | H | H | H | $CH_3$ | H |
| 206 | 2,4-dichloro-5-propargyloxyphenyl | H | H | H | H | $CH_3$ | H |
| 207 | 2,5-dichloro-3-propargyloxyphenyl | H | H | H | H | $CH_3$ | H |
| 208 | 2,5-dichloro-4-propargyloxyphenyl | H | H | H | H | $CH_3$ | H |
| 209 | 2,4-dichloro-5-methoxyphenyl | H | H | H | H | $CH_3$ | $CH_3$ |
| 210 | 2,5-dichloro-3-methoxyphenyl | H | H | H | H | $CH_3$ | $CH_3$ |
| 211 | 2,5-dichloro-4-methoxyphenyl | H | H | H | H | $CH_3$ | $CH_3$ |
| 212 | 2,4-dichloro-5-ethoxyphenyl | H | H | H | H | $CH_3$ | $CH_3$ |
| 213 | 2,5-dichloro-3-ethoxyphenyl | H | H | H | H | $CH_3$ | $CH_3$ |
| 214 | 2,5-dichloro-4-ethoxyphenyl | H | H | H | H | $CH_3$ | $CH_3$ |
| 215 | 2,4-dichloro-5-propoxyphenyl | H | H | H | H | $CH_3$ | $CH_3$ |
| 216 | 2,5-dichloro-3-propoxyphenyl | H | H | H | H | $CH_3$ | $CH_3$ |
| 217 | 2,5-dichloro-4-propoxyphenyl | H | H | H | H | $CH_3$ | $CH_3$ |
| 218 | 2,4-dichloro-5-iso-propoxyphenyl | H | H | H | H | $CH_3$ | $CH_3$ |
| 219 | 2,5-dichloro-3-iso-propoxyphenyl | H | H | H | H | $CH_3$ | $CH_3$ |
| 220 | 2,5-dichloro-4-iso-propoxyphenyl | H | H | H | H | $CH_3$ | $CH_3$ |
| 221 | 2,4-dichloro-5-butoxyphenyl | H | H | H | H | $CH_3$ | $CH_3$ |
| 222 | 2,5-dichloro-3-butoxyphenyl | H | H | H | H | $CH_3$ | $CH_3$ |
| 223 | 2,5-dichloro-4-butoxyphenyl | H | H | H | H | $CH_3$ | $CH_3$ |
| 224 | 2,4-dichloro-5-iso-butoxyphenyl | H | H | H | H | $CH_3$ | $CH_3$ |
| 225 | 2,5-dichloro-3-iso-butoxyphenyl | H | H | H | H | $CH_3$ | $CH_3$ |
| 226 | 2,5-dichloro-4-iso-butoxyphenyl | H | H | H | H | $CH_3$ | $CH_3$ |
| 227 | 2,4-dichloro-5-tert-butoxyphenyl | H | H | H | H | $CH_3$ | $CH_3$ |
| 228 | 2,5-dichloro-3-tert-butoxyphenyl | H | H | H | H | $CH_3$ | $CH_3$ |
| 229 | 2,5-dichloro-4-tert-butoxyphenyl | H | H | H | H | $CH_3$ | $CH_3$ |
| 230 | 2,4-dichloro-5-propargyloxyphenyl | H | H | H | H | $CH_3$ | $CH_3$ |
| 231 | 2,5-dichloro-3-propargyloxyphenyl | H | H | H | H | $CH_3$ | $CH_3$ |
| 232 | 2,5-dichloro-4-propargyloxyphenyl | H | H | H | H | $CH_3$ | $CH_3$ |
| 233 | 2,4-dichloro-5-methoxyphenyl | $CH_3$ | H | H | H | $CH_3$ | H |
| 234 | 2,5-dichloro-3-methoxyphenyl | $CH_3$ | H | H | H | $CH_3$ | H |
| 235 | 2,5-dichloro-4-methoxyphenyl | $CH_3$ | H | H | H | $CH_3$ | H |

TABLE 3-continued

| Cmpd. No. | A Ring moiety | $R^1$ | $R^2$ | $R^3$ | $R^4$ | $R^5$ | $R^6$ |
|---|---|---|---|---|---|---|---|
| 236 | 2,4-dichloro-5-ethoxyphenyl | $CH_3$ | H | H | H | $CH_3$ | H |
| 237 | 2,5-dichloro-3-ethoxyphenyl | $CH_3$ | H | H | H | $CH_3$ | H |
| 238 | 2,5-dichloro-4-ethoxyphenyl | $CH_3$ | H | H | H | $CH_3$ | H |
| 239 | 2,4-dichloro-5-propoxyphenyl | $CH_3$ | H | H | H | $CH_3$ | H |
| 240 | 2,5-dichloro-3-propoxyphenyl | $CH_3$ | H | H | H | $CH_3$ | H |
| 241 | 2,5-dichloro-4-propoxyphenyl | $CH_3$ | H | H | H | $CH_3$ | H |
| 242 | 2,4-dichloro-5-iso-propoxyphenyl | $CH_3$ | H | H | H | $CH_3$ | H |
| 243 | 2,5-dichloro-3-iso-propoxyphenyl | $CH_3$ | H | H | H | $CH_3$ | H |
| 244 | 2,5-dichloro-4-iso-propoxyphenyl | $CH_3$ | H | H | H | $CH_3$ | H |
| 245 | 2,4-dichloro-5-butoxyphenyl | $CH_3$ | H | H | H | $CH_3$ | H |
| 246 | 2,5-dichloro-3-butoxyphenyl | $CH_3$ | H | H | H | $CH_3$ | H |
| 247 | 2,5-dichloro-4-butoxyphenyl | $CH_3$ | H | H | H | $CH_3$ | H |
| 248 | 2,4-dichloro-5-iso-butoxyphenyl | $CH_3$ | H | H | H | $CH_3$ | H |
| 249 | 2,5-dichloro-3-iso-butoxyphenyl | $CH_3$ | H | H | H | $CH_3$ | H |
| 250 | 2,5-dichloro-4-iso-butoxyphenyl | $CH_3$ | H | H | H | $CH_3$ | H |
| 251 | 2,4-dichloro-5-tert-butoxyphenyl | $CH_3$ | H | H | H | $CH_3$ | H |
| 252 | 2,5-dichloro-3-tert-butoxyphenyl | $CH_3$ | H | H | H | $CH_3$ | H |
| 253 | 2,5-dichloro-4-tert-butoxyphenyl | $CH_3$ | H | H | H | $CH_3$ | H |
| 254 | 2,4-dichloro-5-propargyloxyphenyl | $CH_3$ | H | H | H | $CH_3$ | H |
| 255 | 2,5-dichloro-3-propargyloxyphenyl | $CH_3$ | H | H | H | $CH_3$ | H |
| 256 | 2,5-dichloro-4-propargyloxyphenyl | $CH_3$ | H | H | H | $CH_3$ | H |

The following are non-limiting examples of compounds of structural formula IIIc according to this aspect of Category I of the disclosed FABP4/5 inhibitors:

B116

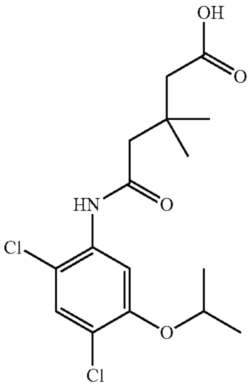

5-((2,4-dichloro-5-isopropoxyphenyl)amino)-3,3-dimethyl-5-oxopentanoic acid;

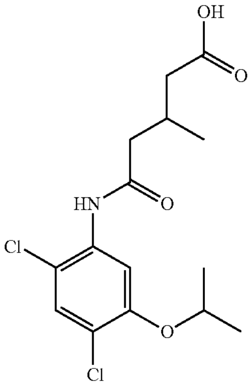

5-((2,4-dichloro-5-isopropoxyphenyl)amino)-3-methyl-5-oxopentanoic acid;

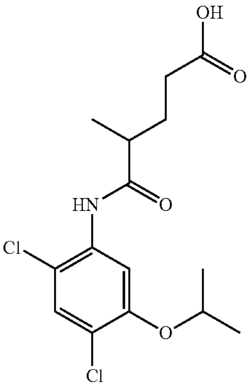

5-((2,4-dichloro-5-isopropoxyphenyl)amino)-4-methyl-5-oxopentanoic acid;

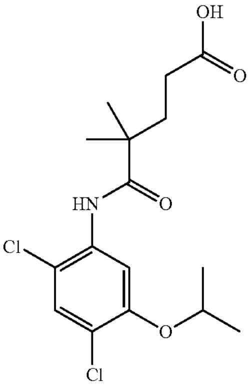 [SMILES: CC(C)Oc1cc(NC(=O)C(C)(C)CCC(=O)O)c(Cl)cc1Cl]

5-((2,4-dichloro-5-isopropoxyphenyl)amino)-4,4-dimethyl-5-oxopentanoic acid;

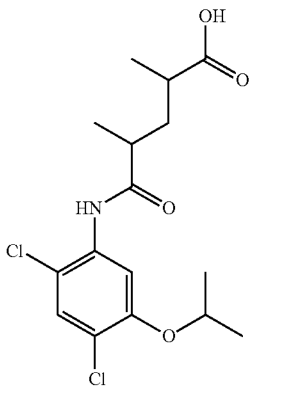 [SMILES: CC(C)Oc1cc(NC(=O)C(C)CC(C)C(=O)O)c(Cl)cc1Cl]

5-((2,4-dichloro-5-isopropoxyphenyl)amino)-2,4-dimethyl-5-oxopentanoic acid;

B114

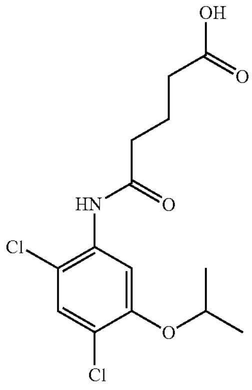

5-((2,4-dichloro-5-isopropoxyphenyl)amino)-5-oxopentanoic acid; and

B118

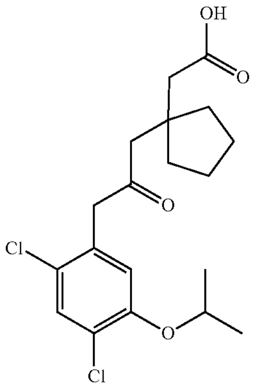

2-(1-(2-((2,4-dichloro-5-isopropoxyphenyl)amino)-2-oxoethyl)cyclopentyl)acetic acid.

In a further aspect of the FABP4/5 inhibitor compounds of Category I (e.g., compound of structural formula III), the present disclosure also provides compounds of structural formula IIId:

(IIId)

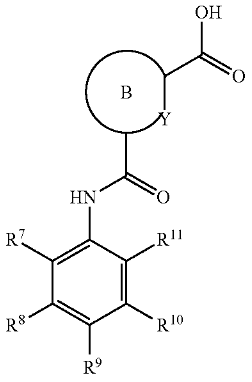

wherein $R^1$ and $R^4$ (as shown in compound of formula III) are taken together with the Y unit to form a B ring having from 5 to 7 atoms; Y is —$CR^5R^6$—, or a heteroatom chosen from —S— or —O—; $R^5$ and $R^6$ are hydrogen; $R^2$ and $R^3$ are hydrogen; each of $R^7$, $R^1$, $R^9$, $R^{10}$, and $R^{11}$ is independently chosen from hydrogen, halogen, or linear, branched, saturated or unsaturated $C_1$-$C_4$ alkyloxy, phenoxy or benzyloxy. In at least one embodiment, the compound of structural formula IIId includes any pharmaceutically acceptable salt thereof.

Specific non-limiting examples of compounds of structural formula IIId according to this aspect of Category I include the compounds (257)-(328) as further described in Table 4 (below).

TABLE 4

| Cmpd. No. | Aryl A Ring | Heteroaryl B Ring |
|---|---|---|
| 257 | 2,4-dichloro-5-methoxyphenyl | 2,5-tetrahydrothiophenyl |
| 258 | 2,5-dichloro-3-methoxyphenyl | 2,5-tetrahydrothiophenyl |
| 259 | 2,5-dichloro-4-methoxyphenyl | 2,5-tetrahydrothiophenyl |
| 260 | 2,4-dichloro-5-ethoxyphenyl | 2,5-tetrahydrothiophenyl |
| 261 | 2,5-dichloro-3-ethoxyphenyl | 2,5-tetrahydrothiophenyl |
| 262 | 2,5-dichloro-4-ethoxyphenyl | 2,5-tetrahydrothiophenyl |
| 263 | 2,4-dichloro-5-propoxyphenyl | 2,5-tetrahydrothiophenyl |
| 264 | 2,5-dichloro-3-propoxyphenyl | 2,5-tetrahydrothiophenyl |
| 265 | 2,5-dichloro-4-propoxyphenyl | 2,5-tetrahydrothiophenyl |
| 266 | 2,4-dichloro-5-iso-propoxyphenyl | 2,5-tetrahydrothiophenyl |
| 267 | 2,5-dichloro-3-iso-propoxyphenyl | 2,5-tetrahydrothiophenyl |
| 268 | 2,5-dichloro-4-iso-propoxyphenyl | 2,5-tetrahydrothiophenyl |
| 269 | 2,4-dichloro-5-butoxyphenyl | 2,5-tetrahydrothiophenyl |
| 270 | 2,5-dichloro-3-butoxyphenyl | 2,5-tetrahydrothiophenyl |
| 271 | 2,5-dichloro-4-butoxyphenyl | 2,5-tetrahydrothiophenyl |
| 272 | 2,4-dichloro-5-iso-butoxyphenyl | 2,5-tetrahydrothiophenyl |
| 273 | 2,5-dichloro-3-iso-butoxyphenyl | 2,5-tetrahydrothiophenyl |
| 274 | 2,5-dichloro-4-iso-butoxyphenyl | 2,5-tetrahydrothiophenyl |
| 275 | 2,4-dichloro-5-tert-butoxyphenyl | 2,5-tetrahydrothiophenyl |
| 276 | 2,5-dichloro-3-tert-butoxyphenyl | 2,5-tetrahydrothiophenyl |
| 277 | 2,5-dichloro-4-tert-butoxyphenyl | 2,5-tetrahydrothiophenyl |
| 278 | 2,4-dichloro-5-propargyloxyphenyl | 2,5-tetrahydrothiophenyl |
| 279 | 2,5-dichloro-3-propargyloxyphenyl | 2,5-tetrahydrothiophenyl |
| 280 | 2,5-dichloro-4-propargyloxyphenyl | 2,5-tetrahydrothiophenyl |
| 281 | 2,4-dichloro-5-methoxyphenyl | 2,5-tetrahydrofuranyl |
| 282 | 2,5-dichloro-3-methoxyphenyl | 2,5-tetrahydrofuranyl |
| 283 | 2,5-dichloro-4-methoxyphenyl | 2,5-tetrahydrofuranyl |
| 284 | 2,4-dichloro-5-ethoxyphenyl | 2,5-tetrahydrofuranyl |
| 285 | 2,5-dichloro-3-ethoxyphenyl | 2,5-tetrahydrofuranyl |
| 286 | 2,5-dichloro-4-ethoxyphenyl | 2,5-tetrahydrofuranyl |
| 287 | 2,4-dichloro-5-propoxyphenyl | 2,5-tetrahydrofuranyl |
| 288 | 2,5-dichloro-3-propoxyphenyl | 2,5-tetrahydrofuranyl |
| 289 | 2,5-dichloro-4-propoxyphenyl | 2,5-tetrahydrofuranyl |
| 290 | 2,4-dichloro-5-iso-propoxyphenyl | 2,5-tetrahydrofuranyl |
| 291 | 2,5-dichloro-3-iso-propoxyphenyl | 2,5-tetrahydrofuranyl |

TABLE 4-continued

| Cmpd. No. | Aryl A Ring | Heteroaryl B Ring |
|---|---|---|
| 292 | 2,5-dichloro-4-iso-propoxyphenyl | 2,5-tetrahydrofuranyl |
| 293 | 2,4-dichloro-5-butoxyphenyl | 2,5-tetrahydrofuranyl |
| 294 | 2,5-dichloro-3-butoxyphenyl | 2,5-tetrahydrofuranyl |
| 295 | 2,5-dichloro-4-butoxyphenyl | 2,5-tetrahydrofuranyl |
| 296 | 2,4-dichloro-5-iso-butoxyphenyl | 2,5-tetrahydrofuranyl |
| 297 | 2,5-dichloro-3-iso-butoxyphenyl | 2,5-tetrahydrofuranyl |
| 298 | 2,5-dichloro-4-iso-butoxyphenyl | 2,5-tetrahydrofuranyl |
| 299 | 2,4-dichloro-5-tert-butoxyphenyl | 2,5-tetrahydrofuranyl |
| 300 | 2,5-dichloro-3-tert-butoxyphenyl | 2,5-tetrahydrofuranyl |
| 301 | 2,5-dichloro-4-tert-butoxyphenyl | 2,5-tetrahydrofuranyl |
| 302 | 2,4-dichloro-5-propareyloxyphenyl | 2,5-tetrahydrofuranyl |
| 303 | 2,5-dichloro-3-propareyloxyphenyl | 2,5-tetrahydrofuranyl |
| 304 | 2,5-dichloro-4-propareyloxyphenyl | 2,5-tetrahydrofuranyl |
| 305 | 2,4-dichloro-5-methoxyphenyl | 2,5-cyclopentyl |
| 306 | 2,5-dichloro-3-methoxyphenyl | 2,5-cyclopentyl |
| 307 | 2,5-dichloro-4-methoxyphenyl | 2,5-cyclopentyl |
| 308 | 2,4-dichloro-5-ethoxyphenyl | 2,5-cyclopentyl |
| 309 | 2,5-dichloro-3-ethoxyphenyl | 2,5-cyclopentyl |
| 310 | 2,5-dichloro-4-ethoxyphenyl | 2,5-cyclopentyl |
| 311 | 2,4-dichloro-5-propoxyphenyl | 2,5-cyclopentyl |
| 312 | 2,5-dichloro-3-propoxyphenyl | 2,5-cyclopentyl |
| 313 | 2,5-dichloro-4-propoxyphenyl | 2,5-cyclopentyl |
| 314 | 2,4-dichloro-5-iso-propoxyphenyl | 2,5-cyclopentyl |
| 315 | 2,5-dichloro-3-iso-propoxyphenyl | 2,5-cyclopentyl |
| 316 | 2,5-dichloro-4-iso-propoxyphenyl | 2,5-cyclopentyl |
| 317 | 2,4-dichloro-5-butoxyphenyl | 2,5-cyclopentyl |
| 318 | 2,5-dichloro-3-butoxyphenyl | 2,5-cyclopentyl |
| 319 | 2,5-dichloro-4-butoxyphenyl | 2,5-cyclopentyl |
| 320 | 2,4-dichloro-5-iso-butoxyphenyl | 2,5-cyclopentyl |
| 321 | 2,5-dichloro-3-iso-butoxyphenyl | 2,5-cyclopentyl |
| 322 | 2,5-dichloro-4-iso-butoxyphenyl | 2,5-cyclopentyl |
| 323 | 2,4-dichloro-5-tert-butoxyphenyl | 2,5-cyclopentyl |
| 324 | 2,5-dichloro-3-tert-butoxyphenyl | 2,5-cyclopentyl |
| 325 | 2,5-dichloro-4-tert-butoxyphenyl | 2,5-cyclopentyl |
| 326 | 2,4-dichloro-5-propareyloxyphenyl | 2,5-cyclopentyl |
| 327 | 2,5-dichloro-3-propareyloxyphenyl | 2,5-cyclopentyl |
| 328 | 2,5-dichloro-4-propareyloxyphenyl | 2,5-cyclopentyl |

The following are non-limiting examples of compounds of structural formula IIId according to this aspect of Category I of the disclosed FABP4/5 inhibitors:

B108

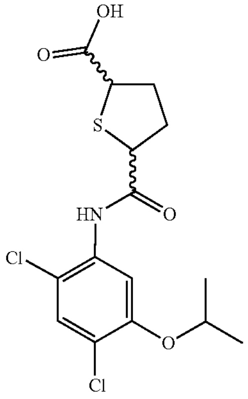

5-((2,4-dichloro-5-isopropoxyphenyl)carbamoyl)tetrahydrothiophene-2-carboxylic acid;

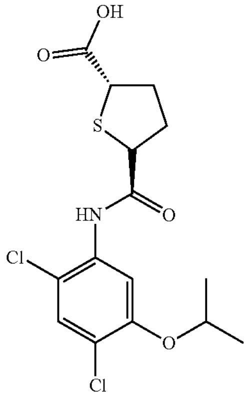

(2S,5R)-5-((2,4-dichloro-5-isopropoxyphenyl)carbamoyl)tetrahydrothiophene-2-carboxylic acid;

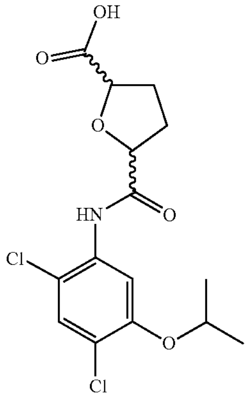 [SMILES: CC(C)Oc1cc(NC(=O)C2CCC(C(=O)O)O2)c(Cl)cc1Cl]

5-((2,4-dichloro-5-isopropoxyphenyl)carbamoyl)tetrahydrofuran-2-carboxylic acid;

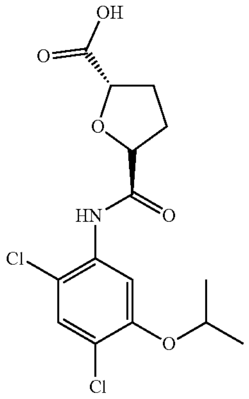

(2S,5R)-5-((2,4-dichloro-5-isopropoxyphenyl)carbamoyl)tetrahydrofuran-2-carboxylic acid;

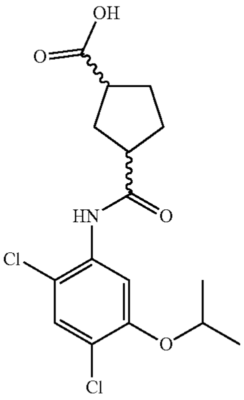 [SMILES: CC(C)Oc1cc(NC(=O)C2CCC(C(=O)O)C2)c(Cl)cc1Cl]

3-((2,4-dichloro-5-isopropoxyphenyl)carbamoyl)cyclopentanecarboxylic acid; and

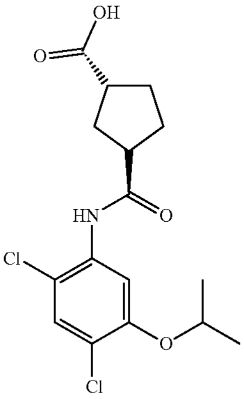

(1R,3S)-3-((2,4-dichloro-5-isopropoxyphenyl)carbamoyl)cyclopentane-1-carboxylic acid.

A further aspect of Category I of the disclosed FABP4/5 inhibitors according to this aspect, have structural formula IIIe:

(IIIe)

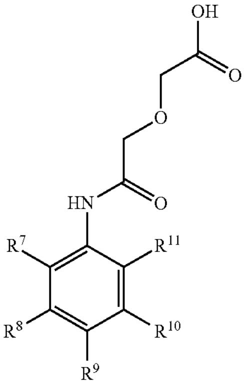

wherein each of $R^1$, $R^2$, $R^3$, and $R^4$ are chosen from hydrogen or linear or branched $C_1$-$C_4$ alkyl; each of $R^7$, $R^8$, $R^9$, $R^{10}$, and $R^{11}$ is independently chosen from hydrogen, halogen, or linear, branched, saturated or unsaturated $C_1$-$C_4$ alkyloxy, phenoxy or benzyloxy. In at least one embodiment, the compound of structural formula IIIe includes any pharmaceutically acceptable salt thereof.

In at least one embodiment, the FABP4 and FABP5 inhibitor compounds of structural formula IIIe (as described above and elsewhere herein) are subject to the proviso that when Y is —O—, $R^1$, $R^2$, $R^3$, $R^4$, $R^8$, and $R^{11}$ are hydrogen, and $R^7$ and $R^9$ are Cl, $R^{10}$ is not hydrogen, or 2-methoxyethoxy.

Specific non-limiting examples of compounds of structural formula ile according to this aspect of Category I include the compounds (329)-(440) as further described in Table 5 (below).

TABLE 5

| Cmpd. No. | Ring A |
|---|---|
| 329 | 2-chlorophenyl |
| 330 | 3-chlorophenyl |
| 331 | 4-chlorophenyl |
| 332 | 2,3-dichlorophenyl |
| 333 | 2,4-dichlorophenyl |
| 334 | 2,5-dichlorophenyl |
| 335 | 2,6-dichlorophenyl |
| 336 | 3,4-dichlorophenyl |
| 337 | 3,5-dichlorophenyl |
| 338 | 2,3,4-trichlorophenyl |
| 339 | 2,3,5-trichlorophenyl |
| 340 | 2,3,6-trichlorophenyl |
| 341 | 3,4,5-trichlorophenyl |
| 342 | 2-chloro-3-methoxyphenyl |
| 343 | 2-chloro-4-methoxyphenyl |
| 344 | 2-chloro-5-methoxyphenyl |
| 345 | 2-chloro-6-methoxyphenyl |
| 346 | 3-chloro-2-methoxyphenyl |
| 347 | 3-chloro-4-methoxyphenyl |
| 348 | 3-chloro-5-methoxyphenyl |
| 349 | 4-chloro-2-methoxyphenyl |
| 350 | 4-chloro-3-methoxyphenyl |
| 351 | 2,3-dichloro-4-methoxyphenyl |
| 352 | 2,4-dichloro-3-methoxyphenyl |
| 353 | 2,4-dichloro-5-methoxyphenyl |
| 354 | 2,4-dichloro-6-methoxyphenyl |
| 355 | 2,5-dichloro-3-methoxyphenyl |
| 356 | 2,5-dichloro-4-methoxyphenyl |
| 357 | 2-chloro-3-ethoxyphenyl |
| 358 | 2-chloro-4-ethoxyphenyl |
| 359 | 2-chloro-5-ethoxyphenyl |
| 360 | 2-chloro-6-ethoxyphenyl |
| 361 | 3-chloro-2-ethoxyphenyl |
| 362 | 3-chloro-4-ethoxyphenyl |
| 363 | 3-chloro-5-ethoxyphenyl |
| 364 | 4-chloro-2-ethoxyphenyl |
| 365 | 4-chloro-3-ethoxyphenyl |
| 366 | 2,3-dichloro-4-ethoxyphenyl |
| 367 | 2,4-dichloro-3-ethoxyphenyl |
| 368 | 2,4-dichloro-5-ethoxyphenyl |
| 369 | 2,4-dichloro-6-ethoxyphenyl |
| 370 | 2,5-dichloro-3-ethoxyphenyl |
| 371 | 2,5-dichloro-4-ethoxyphenyl |
| 372 | 2-chloro-3-ethoxyphenyl |
| 373 | 2-chloro-4-ethoxyphenyl |
| 374 | 2-chloro-5-ethoxyphenyl |
| 375 | 2-chloro-6-ethoxyphenyl |
| 376 | 3-chloro-2-ethoxyphenyl |
| 377 | 3-chloro-4-ethoxyphenyl |
| 378 | 3-chloro-5-ethoxyphenyl |
| 379 | 4-chloro-2-ethoxyphenyl |
| 380 | 4-chloro-3-ethoxyphenyl |
| 381 | 2,3-dichloro-4-ethoxyphenyl |
| 382 | 2,4-dichloro-3-ethoxyphenyl |
| 383 | 2,4-dichloro-5-ethoxyphenyl |
| 384 | 2,4-dichloro-6-ethoxyphenyl |
| 385 | 2,5-dichloro-3-ethoxyphenyl |
| 386 | 2,5-dichloro-4-ethoxyphenyl |
| 387 | 2-chloro-3-propoxyphenyl |

TABLE 5-continued

| Cmpd. No. | Ring A |
|---|---|
| 388 | 2-chloro-4-propoxyphenyl |
| 389 | 2-chloro-5-propoxyphenyl |
| 390 | 2-chloro-6-propoxyphenyl |
| 391 | 3-chloro-2-propoxyphenyl |
| 392 | 3-chloro-4-propoxyphenyl |
| 393 | 3-chloro-5-propoxyphenyl |
| 394 | 4-chloro-2-propoxyphenyl |
| 395 | 4-chloro-3-propoxyphenyl |
| 396 | 2,3-dichloro-4-propoxyphenyl |
| 397 | 2,4-dichloro-3-propoxyphenyl |
| 398 | 2,4-dichloro-5-propoxyphenyl |
| 399 | 2,4-dichloro-6-propoxyphenyl |
| 400 | 2,5-dichloro-3-propoxyphenyl |
| 401 | 2,5-dichloro-4-propoxyphenyl |
| 402 | 2-chloro-3-iso-propoxyphenyl |
| 403 | 2-chloro-4-iso-propoxyphenyl |
| 404 | 2-chloro-5-iso-propoxyphenyl |
| 405 | 2-chloro-6-iso-propoxyphenyl |
| 406 | 3-chloro-2-iso-propoxyphenyl |
| 407 | 3-chloro-4-iso-propoxyphenyl |
| 408 | 3-chloro-5-iso-propoxyphenyl |
| 409 | 4-chloro-2-iso-propoxyphenyl |
| 410 | 4-chloro-3-iso-propoxyphenyl |
| 411 | 2,3-dichloro-4-iso-propoxyphenyl |
| 412 | 2,4-dichloro-3-iso-propoxyphenyl |
| 413 | 2,4-dichloro-5-iso-propoxyphenyl |
| 414 | 2,4-dichloro-6-iso-propoxyphenyl |
| 415 | 2,5-dichloro-3-iso-propoxyphenyl |
| 416 | 2,5-dichloro-4-iso-propoxyphenyl |
| 417 | 2-chloro-3-tert-butoxyphenyl |
| 418 | 2-chloro-4-tert-butoxyphenyl |
| 419 | 2-chloro-5-tert-butoxyphenyl |
| 420 | 2-chloro-6-tert-butoxyphenyl |
| 421 | 3-chloro-2-tert-butoxyphenyl |
| 422 | 3-chloro-4-tert-butoxyphenyl |
| 423 | 3-chloro-5-tert-butoxyphenyl |
| 424 | 4-chloro-2-tert-butoxyphenyl |
| 425 | 4-chloro-3-tert-butoxyphenyl |
| 426 | 2,3-dichloro-4-tert-butoxyphenyl |
| 427 | 2,4-dichloro-3-tert-butoxyphenyl |
| 428 | 2,4-dichloro-5-tert-butoxyphenyl |
| 429 | 2,4-dichloro-6-tert-butoxyphenyl |
| 430 | 2,5-dichloro-3-tert-butoxyphenyl |
| 431 | 2,5-dichloro-4-tert-butoxyphenyl |
| 432 | 2,3-dichloro-4-propargyloxyphenyl |
| 433 | 2,4-dichloro-3-propargyloxyphenyl |
| 434 | 2,4-dichloro-5-propargyloxyphenyl |
| 435 | 2,4-dichloro-6-propargyloxyphenyl |
| 436 | 2,5-dichloro-3-propargyloxyphenyl |
| 437 | 2,5-dichloro-4-propargyloxyphenyl |
| 438 | 2,3-dichloro-4-propargyloxyphenyl |
| 439 | 2,4-dichloro-3-propargyloxyphenyl |
| 440 | 2,4-dichloro-5-propargyloxyphenyl |

The following are non-limiting examples of compounds of structural formula IIIe according to this aspect of Category I of the disclosed FABP4/5 inhibitors:

B110

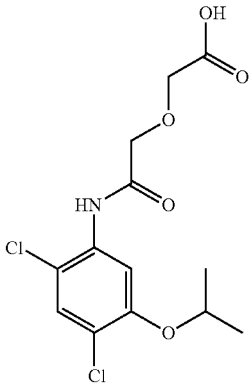

2-(2-((2,4-dichloro-5-isopropoxyphenyl)amino)-2-oxoethoxy)acetic acid;

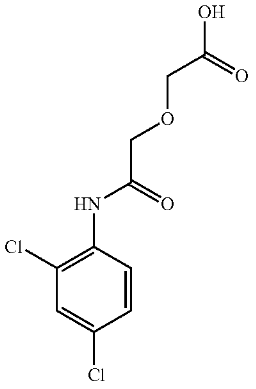 [SMILES: O=C(O)COCC(=O)Nc1ccc(Cl)cc1Cl]

2-(2-((2,4-dichlorophenyl)amino)-2-oxoethoxy)acetic acid;

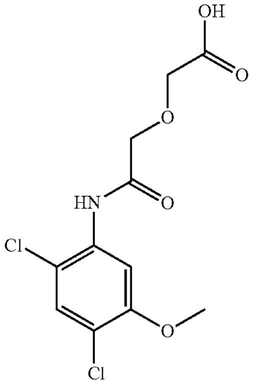 [SMILES: COc1cc(NC(=O)COCC(=O)O)c(Cl)cc1Cl]

2-(2-((2,4-dichloro-5-methoxyphenyl)amino)-2-oxoethoxy) acetic acid;

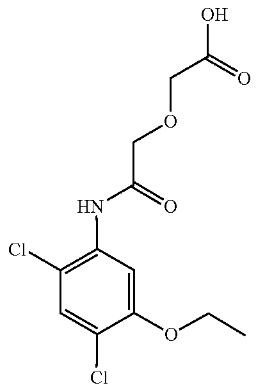 [SMILES: CCOc1cc(NC(=O)COCC(=O)O)c(Cl)cc1Cl]
2-(2-((2,4-dichloro-5-ethoxyphenyl)amino)-2-oxoethoxy) acetic acid;
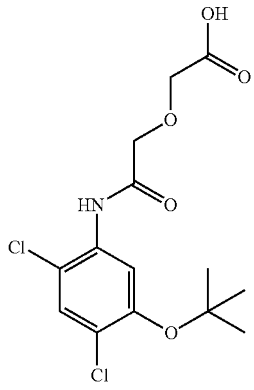
2-(2-((5-(tert-butoxy)-2,4-dichlorophenyl)amino)-2-oxoethoxy)acetic acid;
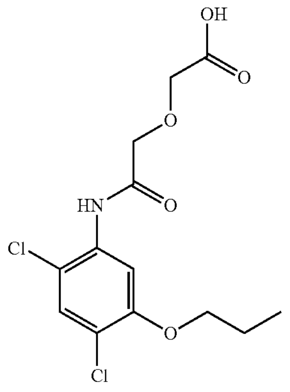 [SMILES: CCCOc1cc(NC(=O)COCC(=O)O)c(Cl)cc1Cl]
2-(2-((2,4-dichloro-5-propoxyphenyl)amino)-2-oxoethoxy) acetic acid;
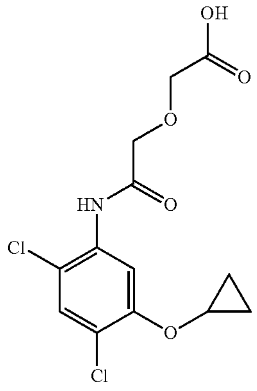
2-(2-((2,4-dichloro-5-cyclopropoxyphenyl)amino)-2-oxoethoxy)acetic acid;
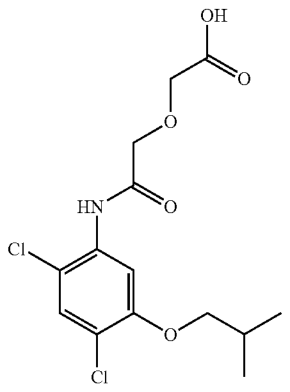 [SMILES: CC(C)COc1cc(NC(=O)COCC(=O)O)c(Cl)cc1Cl]
2-(2-((2,4-dichloro-5-isobutoxyphenyl)amino)-2-oxoethoxy)acetic acid;
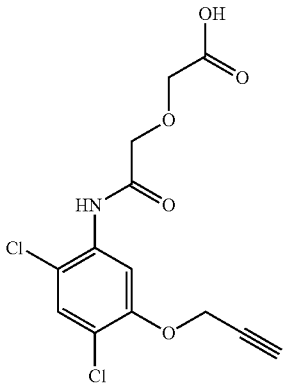 [SMILES: C#CCOc1cc(NC(=O)COCC(=O)O)c(Cl)cc1Cl]
2-(2-((2,4-dichloro-5-(prop-2-yn-1-yloxy)phenyl)amino)-2-oxoethoxy)acetic acid; and

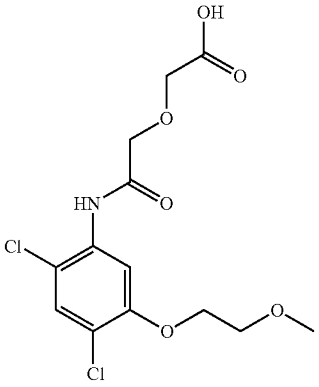

2-(2-((2,4-dichloro-5-(2-methoxyethoxy)phenyl)amino)-2-oxoethoxy)acetic acid.

In at least one embodiment, the FABP4 and FABP5 inhibitor compounds of structural formula IIIe (as described above and elsewhere herein) are subject to the proviso that the compound is not a compound selected from: 2-(2-((2,4-dichloro-5-(2-methoxyethoxy)phenyl)amino)-2-oxoethoxy) acetic acid; and 2-(2-((2,4-dichlorophenyl)amino)-2-oxoethoxy)acetic acid.

A still further aspect of Category I of the disclosed FABP4/5 inhibitors have the structural formula IIIf:

(IIIf)

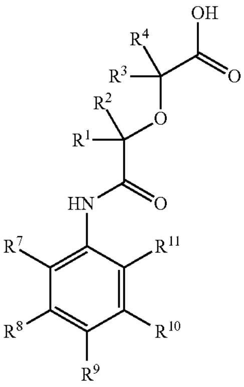

wherein each of $R^1$, $R^2$, $R^3$, and $R^4$ are chosen from hydrogen or linear or branched $C_1$-$C_4$ alkyl, and at least one of $R^1$, $R^2$, $R^3$, and $R^4$ is not hydrogen; each of $R^7$, $R^8$, $R^9$, $R^{10}$, and $R^{11}$ is independently chosen from hydrogen, halogen, or linear, branched, saturated or unsaturated $C_1$-$C_4$ alkyloxy, phenoxy or benzyloxy.

Specific non-limiting examples of compounds of structural formula IIIf according to this aspect of Category I include the compounds (441)-(512) as further described in Table 6 (below).

TABLE 6

| Cmpd. No. | Ring A | $R^1$ | $R^2$ | $R^3$ | $R^4$ |
|---|---|---|---|---|---|
| 441 | 2,4-dichloro-5-methoxyphenyl | H | $CH_3$ | H | H |
| 442 | 2,5-dichloro-3-methoxyphenyl | H | $CH_3$ | H | H |
| 443 | 2,5-dichloro-4-methoxyphenyl | H | $CH_3$ | H | H |
| 444 | 2,4-dichloro-5-ethoxyphenyl | H | $CH_3$ | H | H |
| 445 | 2,5-dichloro-3-ethoxyphenyl | H | $CH_3$ | H | H |
| 446 | 2,5-dichloro-4-ethoxyphenyl | H | $CH_3$ | H | H |
| 447 | 2,4-dichloro-5-propoxyphenyl | H | $CH_3$ | H | H |
| 448 | 2,5-dichloro-3-propoxyphenyl | H | $CH_3$ | H | H |
| 449 | 2,5-dichloro-4-propoxyphenyl | H | $CH_3$ | H | H |
| 450 | 2,4-dichloro-5-iso-propoxyphenyl | H | $CH_3$ | H | H |
| 451 | 2,5-dichloro-3-iso-propoxyphenyl | H | $CH_3$ | H | H |
| 452 | 2,5-dichloro-4-iso-propoxyphenyl | H | $CH_3$ | H | H |
| 453 | 2,4-dichloro-5-butoxyphenyl | H | $CH_3$ | H | H |
| 454 | 2,5-dichloro-3-butoxyphenyl | H | $CH_3$ | H | H |
| 455 | 2,5-dichloro-4-butoxyphenyl | H | $CH_3$ | H | H |
| 456 | 2,4-dichloro-5-iso-butoxyphenyl | H | $CH_3$ | H | H |
| 457 | 2,5-dichloro-3-iso-butoxyphenyl | H | $CH_3$ | H | H |
| 458 | 2,5-dichloro-4-iso-butoxyphenyl | H | $CH_3$ | H | H |
| 459 | 2,4-dichloro-5-tert-butoxyphenyl | H | $CH_3$ | H | H |
| 460 | 2,5-dichloro-3-tert-butoxyphenyl | H | $CH_3$ | H | H |
| 461 | 2,5-dichloro-4-tert-butoxyphenyl | H | $CH_3$ | H | H |
| 462 | 2,4-dichloro-5-propargyloxyphenyl | H | $CH_3$ | H | H |
| 463 | 2,5-dichloro-3-propargyloxyphenyl | H | $CH_3$ | H | H |
| 464 | 2,5-dichloro-4-propargyloxyphenyl | H | $CH_3$ | H | $CH_3$ |
| 465 | 2,4-dichloro-5-methoxyphenyl | H | H | H | $CH_3$ |
| 466 | 2,5-dichloro-3-methoxyphenyl | H | H | H | $CH_3$ |
| 467 | 2,5-dichloro-4-methoxyphenyl | H | H | H | $CH_3$ |
| 468 | 2,4-dichloro-5-ethoxyphenyl | H | H | H | $CH_3$ |
| 469 | 2,5-dichloro-3-ethoxyphenyl | H | H | H | $CH_3$ |
| 470 | 2,5-dichloro-4-ethoxyphenyl | H | H | H | $CH_3$ |
| 471 | 2,4-dichloro-5-propoxyphenyl | H | H | H | $CH_3$ |
| 472 | 2,5-dichloro-3-propoxyphenyl | H | H | H | $CH_3$ |
| 473 | 2,5-dichloro-4-propoxyphenyl | H | H | H | $CH_3$ |
| 474 | 2,4-dichloro-5-iso-propoxyphenyl | H | H | H | $CH_3$ |
| 475 | 2,5-dichloro-3-iso-propoxyphenyl | H | H | H | $CH_3$ |
| 476 | 2,5-dichloro-4-iso-propoxyphenyl | H | H | H | $CH_3$ |
| 477 | 2,4-dichloro-5-butoxyphenyl | H | H | H | $CH_3$ |
| 478 | 2,5-dichloro-3-butoxyphenyl | H | H | H | $CH_3$ |
| 479 | 2,5-dichloro-4-butoxyphenyl | H | H | H | $CH_3$ |
| 480 | 2,4-dichloro-5-iso-butoxyphenyl | H | H | H | $CH_3$ |
| 481 | 2,5-dichloro-3-iso-butoxyphenyl | H | H | H | $CH_3$ |
| 482 | 2,5-dichloro-4-iso-butoxyphenyl | H | H | H | $CH_3$ |
| 483 | 2,4-dichloro-5-tert-butoxyphenyl | H | H | H | $CH_3$ |
| 484 | 2,5-dichloro-3-tert-butoxyphenyl | H | H | H | $CH_3$ |
| 485 | 2,5-dichloro-4-tert-butoxyphenyl | H | H | H | $CH_3$ |
| 486 | 2,4-dichloro-5-propargyloxyphenyl | H | H | H | $CH_3$ |
| 487 | 2,5-dichloro-3-propargyloxyphenyl | H | H | H | $CH_3$ |
| 488 | 2,5-dichloro-4-propargyloxyphenyl | H | H | H | $CH_3$ |
| 489 | 2,4-dichloro-5-methoxyphenyl | H | $CH_3$ | H | $CH_3$ |
| 490 | 2,5-dichloro-3-methoxyphenyl | H | $CH_3$ | H | $CH_3$ |
| 491 | 2,5-dichloro-4-methoxyphenyl | H | $CH_3$ | H | $CH_3$ |
| 492 | 2,4-dichloro-5-ethoxyphenyl | H | $CH_3$ | H | $CH_3$ |
| 493 | 2,5-dichloro-3-ethoxyphenyl | H | $CH_3$ | H | $CH_3$ |
| 494 | 2,5-dichloro-4-ethoxyphenyl | H | $CH_3$ | H | $CH_3$ |
| 495 | 2,4-dichloro-5-propoxyphenyl | H | $CH_3$ | H | $CH_3$ |
| 496 | 2,5-dichloro-3-propoxyphenyl | H | $CH_3$ | H | $CH_3$ |
| 497 | 2,5-dichloro-4-propoxyphenyl | H | $CH_3$ | H | $CH_3$ |
| 498 | 2,4-dichloro-5-iso-propoxyphenyl | H | $CH_3$ | H | $CH_3$ |
| 499 | 2,5-dichloro-3-iso-propoxyphenyl | H | $CH_3$ | H | $CH_3$ |
| 500 | 2,5-dichloro-4-iso-propoxyphenyl | H | $CH_3$ | H | $CH_3$ |
| 501 | 2,4-dichloro-5-butoxyphenyl | H | $CH_3$ | H | $CH_3$ |
| 502 | 2,5-dichloro-3-butoxyphenyl | H | $CH_3$ | H | $CH_3$ |
| 503 | 2,5-dichloro-4-butoxyphenyl | H | $CH_3$ | H | $CH_3$ |
| 504 | 2,4-dichloro-5-iso-butoxyphenyl | H | $CH_3$ | H | $CH_3$ |
| 505 | 2,5-dichloro-3-iso-butoxyphenyl | H | $CH_3$ | H | $CH_3$ |
| 506 | 2,5-dichloro-4-iso-butoxyphenyl | H | $CH_3$ | H | $CH_3$ |
| 507 | 2,4-dichloro-5-tert-butoxyphenyl | H | $CH_3$ | H | $CH_3$ |
| 508 | 2,5-dichloro-3-tert-butoxyphenyl | H | $CH_3$ | H | $CH_3$ |
| 509 | 2,5-dichloro-4-tert-butoxyphenyl | H | $CH_3$ | H | $CH_3$ |
| 510 | 2,4-dichloro-5-propargyloxyphenyl | H | $CH_3$ | H | $CH_3$ |
| 511 | 2,5-dichloro-3-propargyloxyphenyl | H | $CH_3$ | H | $CH_3$ |
| 512 | 2,5-dichloro-4-propargyloxyphenyl | H | $CH_3$ | H | $CH_3$ |

The following are non-limiting examples of compounds of structural formula IIIf according to this aspect of Category I of the disclosed FABP4/5 inhibitors:

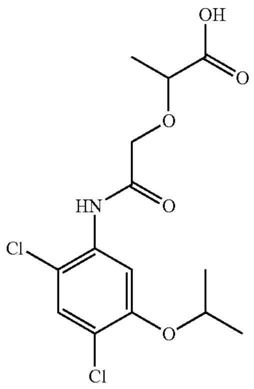 [SMILES: CC(C)Oc1cc(NC(=O)COC(C)C(=O)O)c(Cl)cc1Cl]

2-(2-((2,4-dichloro-5-isopropoxyphenyl)amino)-2-oxoethoxy)propanoic acid;

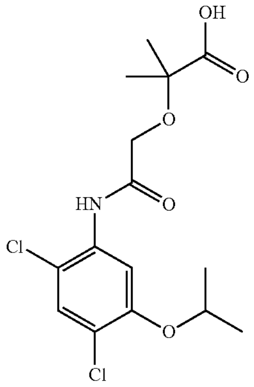 [SMILES: CC(C)Oc1cc(NC(=O)COC(C)(C)C(=O)O)c(Cl)cc1Cl]

2-(2-((2,4-dichloro-5-isopropoxyphenyl)amino)-2-oxoethoxy)-2-methylpropanoic acid; and

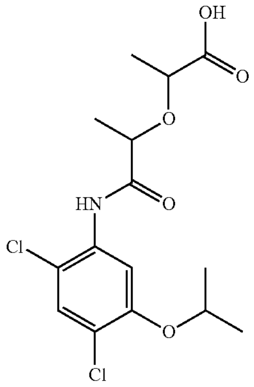 [SMILES: CC(C)Oc1cc(NC(=O)C(C)OC(C)C(=O)O)c(Cl)cc1Cl]

2-((1-((2,4-dichloro-5-isopropoxyphenyl)amino)-1-oxopropan-2-yl)oxy)propanoic acid.

A still further aspect of Category I of the disclosed FABP4/5 inhibitors have the structural formula IIIg:

(IIIg)

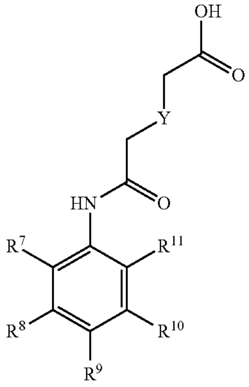

Y is —SO— or —$SO_2$—; each of $R^7$, $R^8$, $R^9$, $R^{10}$, and $R^{11}$ is independently chosen from hydrogen, halogen, or linear, branched, saturated or unsaturated $C_1$-$C_4$ alkyloxy, phenoxy or benzyloxy.

Specific non-limiting examples of compounds of structural formula IIIg according to this aspect of Category I includes compounds (513)-(560) as further described in Table 7 (below).

TAB:E 7

| Cmpd. No. | Ring A | Y |
|---|---|---|
| 513 | 2,4-dichloro-5-methoxyphenyl | —SO— |
| 514 | 2,5-dichloro-3-methoxyphenyl | —SO— |
| 515 | 2,5-dichloro-4-methoxyphenyl | —SO— |
| 516 | 2,4-dichloro-5-ethoxyphenyl | —SO— |
| 517 | 2,5-dichloro-3-ethoxyphenyl | —SO— |
| 518 | 2,5-dichloro-4-ethoxyphenyl | —SO— |
| 519 | 2,4-dichloro-5-propoxyphenyl | —SO— |
| 520 | 2,5-dichloro-3-propoxyphenyl | —SO— |
| 521 | 2,5-dichloro-4-propoxyphenyl | —SO— |
| 522 | 2,4-dichloro-5-isopropoxyphenyl | —SO— |
| 523 | 2,5-dichloro-3-isopropoxyphenyl | —SO— |
| 524 | 2,5-dichloro-4-isopropoxyphenyl | —SO— |
| 525 | 2,4-dichloro-5-butoxyphenyl | —SO— |
| 526 | 2,5-dichloro-3-butoxyphenyl | —SO— |
| 527 | 2,5-dichloro-4-butoxyphenyl | —SO— |
| 528 | 2,4-dichloro-5-isobutoxyphenyl | —SO— |
| 529 | 2,5-dichloro-3-isobutoxyphenyl | —SO— |
| 530 | 2,5-dichloro-4-isobutoxyphenyl | —SO— |
| 531 | 2,4-dichloro-5-tert-butoxyphenyl | —SO— |
| 532 | 2,5-dichloro-3-tert-butoxyphenyl | —SO— |

TAB:E 7-continued

| Cmpd. No. | Ring A | Y |
|---|---|---|
| 533 | 2,5-dichloro-4-tert-butoxyphenyl | —SO— |
| 534 | 2,4-dichloro-5-propargyloxyphenyl | —SO— |
| 535 | 2,5-dichloro-3-propargyloxyphenyl | —SO— |
| 536 | 2,5-dichloro-4-propargyloxyphenyl | —SO— |
| 537 | 2,4-dichloro-5-methoxyphenyl | —$SO_2$— |
| 538 | 2,5-dichloro-3-methoxyphenyl | —$SO_2$— |
| 539 | 2,5-dichloro-4-methoxyphenyl | —$SO_2$— |
| 540 | 2,4-dichloro-5-ethoxyphenyl | —$SO_2$— |
| 541 | 2,5-dichloro-3-ethoxyphenyl | —$SO_2$— |
| 542 | 2,5-dichloro-4-ethoxyphenyl | —$SO_2$— |
| 543 | 2,4-dichloro-5-propoxyphenyl | —$SO_2$— |
| 544 | 2,5-dichloro-3-propoxyphenyl | —$SO_2$— |
| 545 | 2,5-dichloro-4-propoxyphenyl | —$SO_2$— |
| 546 | 2,4-dichloro-5-iso-propoxyphenyl | —$SO_2$— |
| 547 | 2,5-dichloro-3-iso-propoxyphenyl | —$SO_2$— |
| 548 | 2,5-dichloro-4-iso-propoxyphenyl | —$SO_2$— |
| 549 | 2,4-dichloro-5-butoxyphenyl | —$SO_2$— |
| 550 | 2,5-dichloro-3-butoxyphenyl | —$SO_2$— |
| 551 | 2,5-dichloro-4-butoxyphenyl | —$SO_2$— |
| 552 | 2,4-dichloro-5-iso-butoxyphenyl | —$SO_2$— |
| 553 | 2,5-dichloro-3-iso-butoxyphenyl | —$SO_2$— |
| 554 | 2,5-dichloro-4-iso-butoxyphenyl | —$SO_2$— |
| 555 | 2,4-dichloro-5-tert-butoxyphenyl | —$SO_2$— |
| 556 | 2,5-dichloro-3-tert-butoxyphenyl | —$SO_2$— |
| 557 | 2,5-dichloro-4-tert-butoxyphenyl | —$SO_2$— |
| 558 | 2,4-dichloro-5-propargyloxyphenyl | —$SO_2$— |
| 559 | 2,5-dichloro-3-propargyloxyphenyl | —$SO_2$— |
| 560 | 2,5-dichloro-4-propargyloxyphenyl | —$SO_2$— |

The following are non-limiting examples of compounds of structural formula IIIg according to this aspect of Category I of the disclosed FABP4/5 inhibitors:

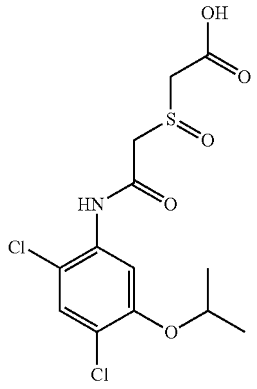 [SMILES: CC(C)Oc1cc(NC(=O)CS(=O)CC(=O)O)c(Cl)cc1Cl]

2-((2-((2,4-dichloro-5-isopropoxyphenyl)amino)-2-oxoethyl)sulfinyl)acetic acid;

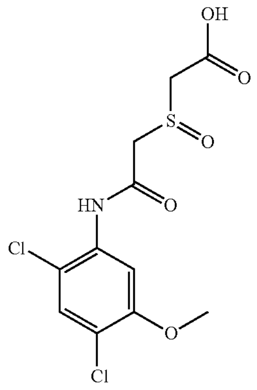 [SMILES: COc1cc(NC(=O)CS(=O)CC(=O)O)c(Cl)cc1Cl]

2-((2-((2,4-dichloro-5-methoxyphenyl)amino)-2-oxoethyl)sulfinyl)acetic acid;

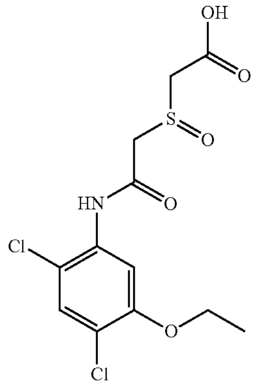 [SMILES: CCOc1cc(NC(=O)CS(=O)CC(=O)O)c(Cl)cc1Cl]

2-((2-((2,4-dichloro-5-ethoxyphenyl)amino)-2-oxoethyl)sulfinyl)acetic acid;

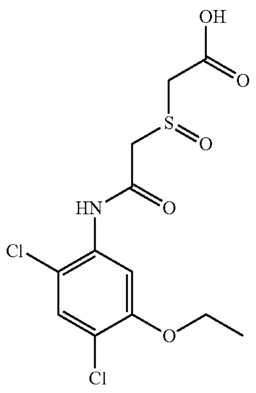 [SMILES: CCOc1cc(NC(=O)CS(=O)CC(=O)O)c(Cl)cc1Cl]

2-((2-((2,4-dichloro-5-propoxyphenyl)amino)-2-oxoethyl)sulfinyl)acetic acid;

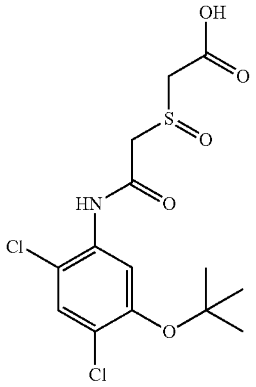 [SMILES: CC(C)(C)Oc1cc(NC(=O)CS(=O)CC(=O)O)c(Cl)cc1Cl]

2-((2-((5-(tert-butoxy)-2,4-dichlorophenyl)amino)-2-oxoethyl)sulfinyl)acetic acid; and

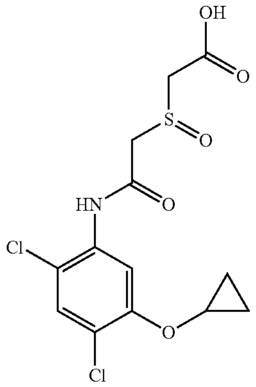 [SMILES: O=C(O)CS(=O)CC(=O)Nc1cc(OC2CC2)c(Cl)cc1Cl]

2-((2-((2,4-dichloro-5-cyclopropoxyphenyl)amino)-2-oxoethyl)sulfinyl)acetic acid.

Category II of the disclosed FABP4/5 inhibitors has the general structural formula IV:

(IV)

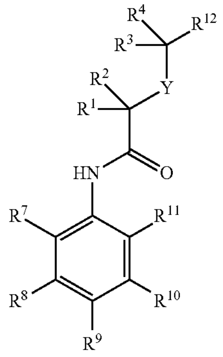

Y is a heteroatom chosen from —S— or —O—, each $R^1$, $R^2$, $R^3$ and $R^4$ is hydrogen and each of $R^7$, $R^8$, $R^9$, $R^{10}$, and $R^{11}$ is hydrogen or one or more substitutions thereof for hydrogen; $R^{12}$ is a carboxylate isostere chosen from:

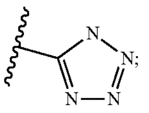
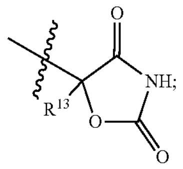
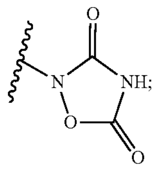

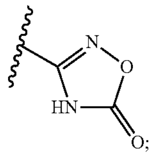
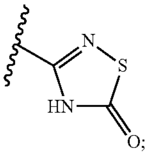
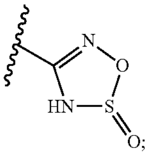

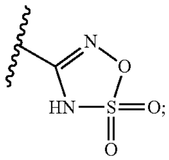
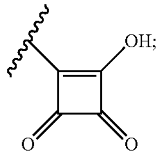

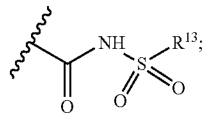
or
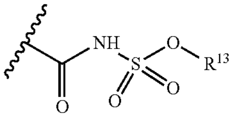

$R^{13}$ is hydrogen or a $C_1$-$C_4$ linear alkyl.

The following are non-limiting examples of compounds of structural formula IV according to Category II:

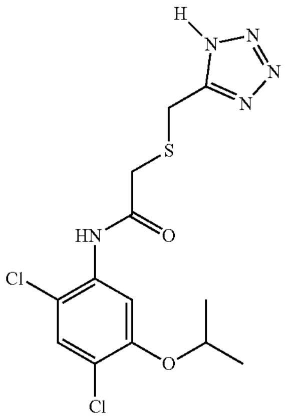 [SMILES: CC(C)Oc1cc(NC(=O)CSCc2nnn[nH]2)c(Cl)cc1Cl]

2-(((1H-tetrazol-5-yl)methyl)thio)-N-(2,4-dichloro-5-isopropoxyphenyl)acetamide;

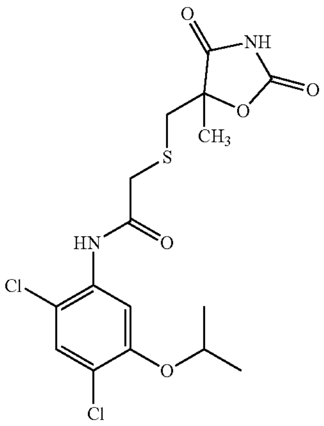 [SMILES: CC(C)Oc1cc(NC(=O)CSCC2(C)OC(=O)NC2=O)c(Cl)cc1Cl]

N-(2,4-dichloro-5-isopropoxyphenyl)-2-(((5-methyl-2,4-dioxooxazolidin-5-yl)methyl)thio)acetamide;

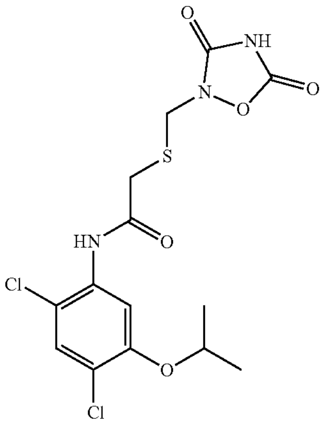 [SMILES: CC(C)Oc1cc(NC(=O)CSCn2oc(=O)[nH]c2=O)c(Cl)cc1Cl]

N-(2,4-dichloro-5-isopropoxyphenyl)-2-(((3,5-dioxo-1,2,4-oxadiazolidin-2-yl)methyl)thio)acetamide;

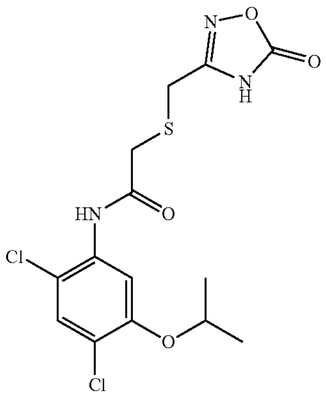 [SMILES: CC(C)Oc1cc(NC(=O)CSCc2noc(=O)[nH]2)c(Cl)cc1Cl]

N-(2,4-dichloro-5-isopropoxyphenyl)-2-(((5-oxo-4,5-dihydro-1,2,4-oxadiazol-3-yl)methyl)thio)acetamide;

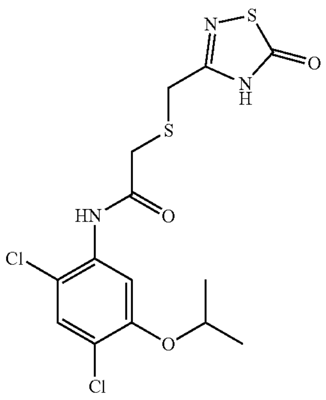 [SMILES: CC(C)Oc1cc(NC(=O)CSCc2nsc(=O)[nH]2)c(Cl)cc1Cl]

N-(2,4-dichloro-5-isopropoxyphenyl)-2-(((5-oxo-4,5-dihydro-1,2,4-thiadiazol-3-yl)methyl)thio)acetamide;

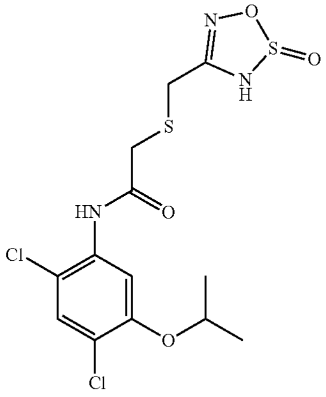 [SMILES: CC(C)Oc1cc(NC(=O)CSCC2=NOS(=O)N2)c(Cl)cc1Cl]

N-(2,4-dichloro-5-isopropoxyphenyl)-2-(((2-oxido-3H-1,2,3,5-oxathiadiazol-4-yl)methyl)thio)acetamide;

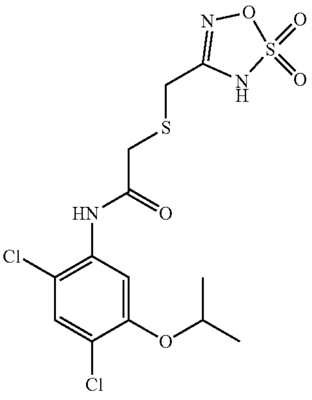 [SMILES: CC(C)Oc1cc(NC(=O)CSCC2=NOS(=O)(=O)N2)c(Cl)cc1Cl]

N-(2,4-dichloro-5-isopropoxyphenyl)-2-(((2,2-dioxido-3H-1,2,3,5-oxathiadiazol-4-yl)methyl)thio)acetamide;

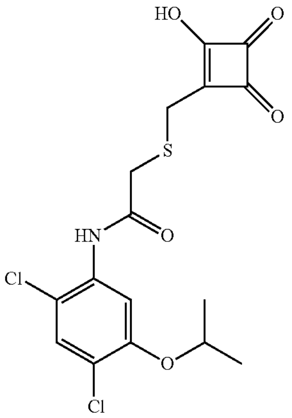 [SMILES: CC(C)Oc1cc(NC(=O)CSCc2c(O)c(=O)c2=O)c(Cl)cc1Cl]

N-(2,4-dichloro-5-isopropoxyphenyl)-2-(((2-hydroxy-3,4-dioxocyclobut-1-en-1-yl)methyl)thio)acetamide;

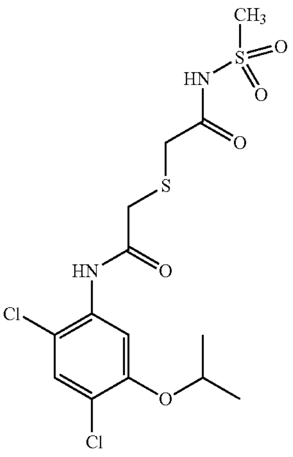 [SMILES: CC(C)Oc1cc(NC(=O)CSCC(=O)NS(C)(=O)=O)c(Cl)cc1Cl]

N-(2,4-dichloro-5-isopropoxyphenyl)-2-((2-(methylsulfonamido)-2-oxoethyl)thio)acetamide; and

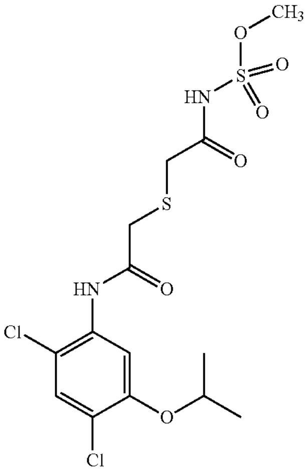 [SMILES: COS(=O)(=O)NC(=O)CSCC(=O)Nc1cc(OC(C)C)c(Cl)cc1Cl]

Methyl (2-((2-((2,4-dichloro-5-isopropoxyphenyl)amino)-2-oxoethyl)thio)acetyl)sulfamate.

As described elsewhere herein, one of ordinary skill will understand that the FABP4/5 inhibitor compounds provided herein can exist in various well-known closely-related and/or equivalent forms not explicitly described by the chemical structures and formulae. It is intended that the FABP4/5 inhibitor compounds of structural formula I of the present disclosure (including compounds of Tables 1-8, and the Examples) includes these closely-related forms of the compounds defined by the chemical structures and formulae including, but not limited to, pharmaceutically acceptable salts of the compounds, mixture of stereoisomers of the compounds, single stereoisomers of the compounds, tautomeric forms of the compounds, and/or prodrug forms of the compounds.

Preparation of FABP4 and FABP5 Inhibitor Compounds

The present disclosure also provides processes for preparing the disclosed FABP4/5 inhibitor compounds described herein, including the compounds of structural formula III (as defined elsewhere herein), which is outlined generally in Scheme I, and described in greater detail below.

Scheme I

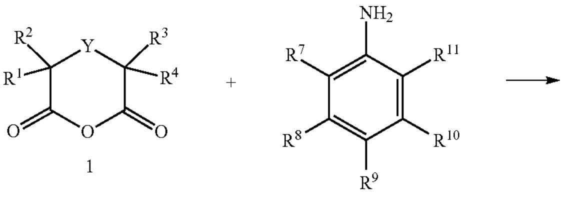

1 2

-continued

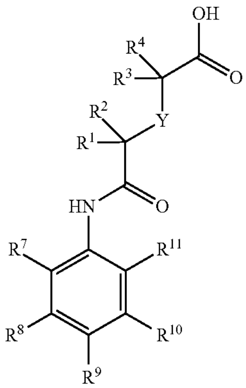

(III)

A mixture of anhydride, 1, and aniline, 2, (1:0.75 molar ratio) is purged with argon then dissolved in a dry solvent. The reaction mixture is then stirred at a temperature from room temperature to the reflux temperature of the chosen solvent. The progress of the reaction can be followed by one or more analytical methods, for example, thin layer chromatography (TLC), gas chromatography, and the like. After the starting material aniline, 2, or anhydride, 1, is deemed to be consumed, the solvent is removed in vacuo to afford the desired FABP4/5 inhibitor of structural formula III.

In at least one embodiment, the process for preparing the disclosed FABP4/5 inhibitor compounds of structural formula III, comprising:

(a) combining in a solvent an anhydride having the formula:

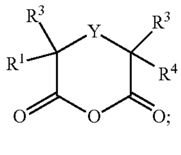

wherein Y is —$CR^5R^6$—, or a heteroatom chosen from —S—, —O—, —SO—, or —$SO_2$—; $R^5$ and $R^6$ are each independently chosen from hydrogen, $C_1$-$C_4$ linear or branched alkyl, phenyl, or benzyl; each $R^1$, $R^2$, $R^3$ and $R^4$ is independently chosen from hydrogen, $C_1$-$C_4$ linear or branched alkyl, phenyl, or benzyl, $R^1$ and $R^4$ can be taken together to form a carbocyclic or heterocyclic ring containing from 5 to 6 atoms or when Y is a carbon atom and $R^5$ and $R^6$ are taken together with the Y unit to form a ring having from 4 to 7 atoms;

with an aniline having the formula:

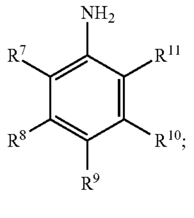

wherein each of $R^7$, $R^8$, $R^9$, $R^{10}$, and $R^{11}$ is independently chosen from:

i) hydrogen;

ii) halogen, for example, fluorine, chlorine, bromine, or iodine;

iii) $C_1$-$C_4$ linear or branched, saturated or unsaturated alkyl;

iv) $C_1$-$C_4$ linear or branched, saturated or unsaturated alkoxy;

v) —$(CR^{12a}R^{12b})_qOR^{13}$;

vi) —$(CR^{12a}R^{12b})_qC(O)R^{13}$;

vii) —$(CR^{12a}R^{12b})_qC(O)OR^{13}$;

viii) —$O(CR^{12a}R^{12b})_qC(O)OR^{13}$;

ix) —$(CR^{12a}R^{12b})_qN(R^{13})_2$;

x) —$CH_mX_n$; wherein X is halogen, m is from 0 to 2, m+n=3;

xi) —$(CR^{12a}R^{12b})_qCN$; and xii) —$(CR^{12a}R^{12b})_qNO_2$;

wherein each $R^{13}$ is independently hydrogen, $C_1$-$C_4$ linear or branched alkyl, phenyl, or benzyl; wherein $R^{12a}$ and $R^{12b}$ are each independently hydrogen, methyl or ethyl, and the index q is an integer from 0 to 4; and (b) removing the solvent to obtain a compound having the structural formula III:

(III)

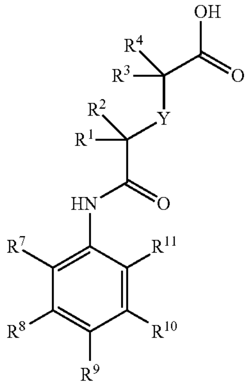

wherein $R^1$, $R^2$, $R^3$, $R^4$ $R^5$, $R^6$, $R^7$, $R^8$, $R^9$, $R^{10}$, and $R^{11}$ are as defined above.

In one embodiment of the anhydride Y is sulfur. In another embodiment of the anhydride Y is oxygen. In a further embodiment Y is —$CR^5R^6$— wherein $R^5$ and $R^6$ are each independently chosen from hydrogen, $C_1$-$C_4$ linear or branched alkyl. In a still further embodiment when Y is $R^5$ and $R^6$ are each independently chosen from $C_1$-$C_4$ linear alkyl, $R^5$ and $R^6$ can be taken together to form a spirocyclic ring having from 4 to 7 atoms. In a still further embodiment when Y is sulfur or oxygen $R^1$ and $R^4$ can be taken together to form a heterocyclic ring having from 4 to 6 carbon atoms.

In one embodiment of the aniline each of $R^7$, $R^8$, $R^9$, $R^{10}$, and $R^{11}$ is independently chosen from hydrogen, chlorine, or saturated or unsaturated $C_1$-$C_4$ linear, branched, or cyclic alkoxy. Non-limiting examples include 2,3-dichloro-4-alkoxyaniline, 2,4-dichloro-3-alkoxyaniline, 2,3-dichloro-5-alkoxyaniline, 2,3-dichloro-6-alkoxyaniline, 2,4-dichloro-6-alkoxyaniline, 2,5-dichloro-4-alkoxyaniline, 2,5-dichloro-6-alkoxyaniline, 2,6-dichloro-3-alkoxyaniline, and 2,6-dichloro-4-alkoxyaniline. Further non-limiting examples include 2,4-dichloro-5-methoxyaniline, 2,4-dichloro-5-ethoxyaniline, 2,4-dichloro-5-propoxyaniline, 2,4-dichloro- 5-isopropoxy-aniline, 2,4-dichloro-5-t-butoxyaniline, 2,4-dichloro-5-cyclopropoxyaniline, and 2,4-dichloro-5-sec-butoxyaniline.

A non-limiting example of the solvent is dichloromethane. A further example of a solvent is diethyl ether.

The following is a non-limiting example of the general procedure for preparing the disclosed FABP4/5 inhibitors. A mixture of anhydride and aniline (1:0.75 molar ratio) is purged with argon then dissolved in dry dichloromethane. The reaction mixture is stirred for 24 h at room temperature. The solvent is removed using a rotary evaporator. The residue is then dissolved in 5 mL of ice-cold dichloromethane and transferred to a glass dram vial. The vial is then cooled on dry ice until visible crystals form. The resulting crystals are isolated via vacuum filtration and rinsed with ice cold dichloromethane. The crystals are allowed to air dry via vacuum filtration for 30 minutes. A small sample of isolated crystal is dissolved in acetone and purity is verified with silica thin-layer chromatography using a solvent system of 40% ethyl acetate in hexanes with 0.1% acetic acid. Plates are stained with PMA as a general stain and the formation of the carboxylic acid is verified with bromocresol green stain. Structure of the purified crystals is verified via $^1$H NNR. The crystals are transferred to a clean, pre-weighed glass dram vial and yield is calculated.

Uses and Methods of Treatment

As noted elsewhere herein, FABP4/5 inhibitor compounds have been proposed or shown to provide potentially therapeutic effects, based on in vitro studies, pre-clinical, or clinical studies in a number of conditions, and diseases. These previously identified FABP4/5 affected conditions and diseases include, but are not limited to, conditions affected by free fatty acid serum levels, metabolic disorders, atherosclerosis, Type-2 diabetes, and cancer (e.g., breast cancer, prostate cancer, ovarian cancer, hepatocellular cancer, multiple myeloma, neuroblastoma, lung adenocarcinoma, and/or gastric carcinoma).

For example, Triple-Negative Breast Cancer (TNBC) accounts for about 10-20% of all breast cancers. The term triple-negative breast cancer refers to the fact that the cancer cells do not produce sufficient estrogen or progesterone receptors or make sufficient amounts of the protein Human Epidermal Growth Factor Receptor 2 (HEGR-2). Because tumors of TNBC lack definitive prognostic markers and selective targets for therapy, the treatment and management of this disease is a significant clinical problem and warrants an urgent need for a direct approach to inhibiting the biological processes which regulate development and metastasis of tumors. As noted elsewhere herein, inhibition of FABP5 provides a method of inhibiting the metastasis of cancer cells in humans. For example, without wishing to be limited by theory, data disclosed herein indicate that the disclosed compounds provide inhibition of FABP5 and can thereby modulate the level of TNBC.

Additionally, FABP4 and FABP5 are members of a family of small, soluble proteins which contribute to the trafficking of fatty acids within the cytosolic compartments of cells. These proteins have no catalytic function but transport hydrophobic fatty acids within the aqueous environment of the cytosol to the various destinations enabling fatty acid oxidation, membrane homeostasis or nuclear signaling. In addition, they are involved in signaling processes which are so far poorly understood. FABP4 is highly expressed in adipose tissue, macrophages, and endothelial cells. FABP5 is also expressed in macrophages, adipocytes and endothelial cells, as well as in skin and several other tissues.

A. Fatty Acid Control

One aspect of the disclosed uses and methods relates to methods for inhibiting FABP4 or FABP5 in a subject, comprising administering to a subject in need a composition, comprising: (a) an effective amount of one or more of the disclosed FABP4/5 inhibitors or a pharmaceutically acceptable salt thereof; and (b) a pharmaceutically acceptable carrier or other adjunct ingredients.

A further aspect of the disclosed uses methods relates to methods for controlling the free fatty acid serum levels in a subject, comprising administering to a subject in need a composition, comprising: (a) an effective amount of one or more of the disclosed FABP4/5 inhibitors or a pharmaceutically acceptable salt thereof; and (b) a pharmaceutically acceptable carrier or other adjunct ingredients.

In at least one embodiment, the present disclosure also provides the use of a FABP4/5 inhibitor compound of the present disclosure, or a pharmaceutical composition comprising a FABP4/5 inhibitor compound of the present disclosure, for the manufacture of a medicament for treating a disease or condition affected by FABP4/5 in a subject. In at least one embodiment, the disease or condition relates to control of the free fatty acid serum levels in a subject.

B. Cancer Treatment

A still further aspect of the disclosed methods relates to methods treating cancer in a subject, comprising administering to a subject in need thereof a composition, comprising: (a) an effective amount of one or more of the disclosed FABP4/5 inhibitors or a pharmaceutically acceptable salt thereof; and (b) a pharmaceutically acceptable carrier or other adjunct ingredients.

In one embodiment of the disclosed cancer treatment method relates to breast cancer. In another embodiment of the disclose methods relate to preventing the metastasis of TNBC cells in a subject diagnosed with cancer.

Another still further aspect of the disclosed methods relates to methods treating cancer in a subject, comprising administering to a subject in need a composition, comprising: (a) an effective amount of one or more of the disclosed FABP4/5 inhibitors or a pharmaceutically acceptable salt thereof; and (b) a pharmaceutically acceptable carrier or other adjunct ingredients. In at least one embodiment of the method of treating cancer, the cancer is chosen from breast cancer, prostate cancer, ovarian cancer, hepatocellular cancer, multiple myeloma, neuroblastoma, lung adenocarcinoma or gastric carcinoma. In one example, the cancer is breast cancer. In a further example the cancer is prostate cancer. In another example the cancer is ovarian cancer. In a yet another example the cancer is hepatocellular cancer. In a still further example, the cancer is multiple myeloma. In another yet example the cancer is neuroblastoma. In a yet still further example, the cancer is lung adenocarcinoma. In a still yet another further example the cancer is gastric carcinoma.

Yet further disclosed herein is a method of sensitizing cancer cells to additional treatment comprising contacting the cancer cells with one or more of the disclosed FABP4/5 inhibitors. One example is to contact the cancer cells with a chemical, for example, doxorubicin, gemcitabine, cisplatin, or paclitaxel.

In at least one embodiment, the present disclosure also provides the use of a FABP4/5 inhibitor compound of the present disclosure, or a pharmaceutical composition comprising a FABP4/5 inhibitor compound of the present disclosure, for the manufacture of a medicament for treating a cancer in a subject. In at least one embodiment, the cancer treated by the use or medicament is chosen from breast cancer, prostate cancer, ovarian cancer, hepatocellular cancer, multiple myeloma, neuroblastoma, lung adenocarcinoma or gastric carcinoma.

C. Metabolic Disorders Treatment

Without wishing to be limited by theory, in humans, plasma levels of FABP4 are increased in patients with metabolic syndrome and atherosclerosis. In addition, there is evidence for involvement of FABP4 in angiogenesis. More than a quarter of the population suffers from an aggregation of co-morbidities, including obesity, atherosclerosis, insulin resistance, dyslipidemias, coagulopathies, hypertension, and a pro-inflammatory state known as the metabolic syndrome. Patients with metabolic syndrome have high risk of atherosclerosis as well as type 2 diabetes and other health problems. Like obesity, atherosclerosis has very limited therapeutic options.

A yet further aspect of the disclosed methods relates to methods for regulating insulin sensitivity in a subject, comprising administering to a subject in need a composition, comprising: (a) an effective amount of one or more of the disclosed FABP4/5 inhibitors or a pharmaceutically acceptable salt thereof; and (b) a pharmaceutically acceptable carrier or other adjunct ingredients.

A yet still further aspect of the disclosed methods relates to methods for treating Type-2 diabetes in a subject, comprising administering to a subject in need thereof a composition, comprising: (a) an effective amount of one or more of the disclosed FABP4/5 inhibitors or a pharmaceutically acceptable salt thereof; and (b) a pharmaceutically acceptable carrier or other adjunct ingredients.

A still yet further aspect of the disclosed methods relates to methods for the glucose plasma level in a subject, comprising administering to a subject in need thereof a composition, comprising: (a) an effective amount of one or more of the disclosed FABP4/5 inhibitors or a pharmaceutically acceptable salt thereof; and (b) a pharmaceutically acceptable carrier or other adjunct ingredients.

A yet still further aspect of the disclosed methods relates to methods for treating atherosclerosis in a subject, comprising administering to a subject in need thereof a composition, comprising: (a) an effective amount of one or more of the disclosed FABP4/5 inhibitors or a pharmaceutically acceptable salt thereof; and (b) a pharmaceutically acceptable carrier or other adjunct ingredients.

A yet further aspect of the disclosed methods relates to methods for treating liver steatosis in a subject, comprising administering to a subject in need thereof a composition, comprising: (a) an effective amount of one or more of the disclosed FABP4/5 inhibitors or a pharmaceutically acceptable salt thereof; and (b) a pharmaceutically acceptable carrier or other adjunct ingredients.

In at least one embodiment, the present disclosure also provides the use of a FABP4/5 inhibitor compound of the present disclosure, or a pharmaceutical composition comprising a FABP4/5 inhibitor compound of the present disclosure, for the manufacture of a medicament for treating a metabolic disorder in a subject.

Pharmaceutical Compositions

The present disclosure also provides uses and methods in which a FABP4/5 inhibitor compound, such as a compound of structural formula I, is administered to a subject in the form of a pharmaceutical composition. In such embodiments, the pharmaceutical composition includes a therapeutically effective amount of the FABP4/5 inhibitor compound (e.g., compound of Tables 1-8), or a pharmaceutically acceptable salt or ester of such a compound and one or more pharmaceutically acceptable carriers. Such pharmaceutical compositions can be prepared using methods well known in the pharmaceutical art (see, e.g., *Remington's Pharmaceutical Sciences*, Mace Publishing Co., Philadelphia, PA 17th Ed. (1985) and *Modern Pharmaceutics*, Marcel Dekker, Inc. 3rd Ed. (G. S. Banker & C. T. Rhodes, Eds.). Methods of preparing pharmaceutical compositions of FABP4/5 inhibitor compounds are described in the present disclosure, including the Examples disclosed herein.

In at least one embodiment, the present disclosure provides a pharmaceutical composition comprising: an effective amount of one or more of the disclosed FABP4/5 inhibitors, such as a compound of structural formula I; and one or more adjunct ingredients, such as a pharmaceutically acceptable carrier. The disclosed compositions can comprise from about 10% to about 95% by weight of one or more of the disclosed FABP4/5 inhibitors. In another embodiment, the compositions comprise from about 10% to about 80% by weight of one or more of the disclosed FABP4/5 inhibitors. In a further embodiment the compositions comprise from about 20% to about 50% by weight of one or more of the disclosed FABP4/5 inhibitors. In a still further embodiment, the compositions comprise from about 50% to about 90% by weight of one or more of the disclosed FABP4/5 inhibitors. In a yet another embodiment the compositions comprise from about 70% to about 90% by weight of one or more of the disclosed FABP4/5 inhibitors. In a yet further embodiment, the compositions comprise from about 80% to about 95% by weight of one or more of the disclosed FABP4/5 inhibitors. In a still yet further embodiment, the compositions comprise from about 90% to about 95% by weight of one or more of the disclosed FABP4/5 inhibitors.

Generally, the pharmaceutical compositions can be prepared by diluting the active ingredient(s) with an excipient and/or enclosing it within a carrier in the form of a capsule, sachet, paper or other container. When the excipient serves as a diluent, it can be a solid, semi-solid, or liquid material (as above), which acts as a vehicle, carrier or medium for the active ingredient. Thus, the pharmaceutical composition(s) suitable for administering in the methods of the disclosure can be in the dosage form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, sterile injectable solutions, and sterile packaged powders.

The carriers used in the preparation of the pharmaceutical compositions can include excipients such as inert solid diluents and fillers, diluents, including sterile aqueous solution and various organic solvents, permeation enhancers, solubilizers and adjuvants. Suitable excipients for use in the pharmaceutical compositions comprising a celastrol derivative of the present disclosure are well known in the art and include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The pharmaceutical compositions can additionally include: lubricating agents such as talc, magnesium stearate, and mineral oil; wetting agents; emulsifying and suspending agents; preserving agents such as methyl- and propyl hydroxy-benzoates; sweetening agents; and flavoring agents.

In the uses and methods of treatment, it is contemplated that the pharmaceutical composition comprising the FABP4/5 inhibitor compounds, such as a compound of structural formula I, can be administered either as single or multiple doses, and by any of the accepted modes of administration of active ingredients having similar utility. For example, a pharmaceutical composition comprising an celastrol derivative can be administered using a variety of different modes including oral administration, intravenous administration, topical administration, parenteral administration, intraperitoneal administration, intramuscular administration, intrathecal administration, intralesional administration, intracranial administration, intranasal administration, intraocular administration, intracardiac administration, intravitreal administration, intraosseous administration, intracerebral administration, intraarterial administration, intraarticular administration, intradermal administration, transdermal administration, transmucosal administration, sublingual administration, enteral administration, sublabial administration, insufflation administration, suppository administration, inhaled administration, or subcutaneous administration.

The pharmaceutical compositions including the FABP4/5 inhibitor compounds of the present disclosure can be used in a range of therapeutic methods of treatment and a range of dosages are contemplated for administration of a pharmaceutically effective amount. The dosage and frequency (single or multiple doses) of administration of the pharmaceutical composition to a subject can vary depending upon a range of factors, such as, the route of administration; the subject's size, age, sex, health, body mass, and/or diet; the state of the disease being treated; whether the subject is suffering from any other diseases, and any concurrent treatment being received. One of ordinary skill will understand that adjustment of established dosages (e.g., frequency and duration) to obtain the therapeutically effective amount may be required depending on the subject. Typically, the amount of a pharmaceutical composition containing a FABP4/5 inhibitor compound to be administered to a subject in a therapeutic method of treatment will be determined by a physician, in view of relevant circumstances of the subject being so treated, the chosen route of administration, and of course, the age, the weight, the severity of symptoms, the response of the individual subject to the treatment, and the like.

Generally, a therapeutically effective amount is the amount sufficient for the administered composition to accomplish a desired therapeutic purpose relative to the absence of the compound. For example, the therapeutically effective amount can be the amount determined to be sufficient to contribute to the treatment, prevention, or reduction of a symptom or symptoms of a disease. Methods for determining the dosage providing a therapeutically effective amount of a compound are well-known to those of ordinary skill in the art, and typically are based on analysis of amounts determined in cellular assays and/or animal models. For example, a dosage for administration to humans can be formulated to achieve a concentration that has been observed as therapeutically effective in an animal model. The dosage in the pharmaceutical composition for humans can further be adjusted by monitoring the effectiveness and adjusting upwards or downwards. One of ordinary skill can use methods well known in the art to adjust the dosage in a pharmaceutical composition of the present disclosure to achieve maximal therapeutic efficacy for humans.

Generally, methods for therapeutic treatment are developed by starting with a pharmaceutical composition containing less than the optimal dose of the FABP4/5 inhibitor compound. Thereafter, the dosage of the compound is increased incrementally until optimal efficacy is attained. A key factor considered in developing the optimal dose is the ratio between the toxicity and the therapeutic efficacy of the active ingredient. This ratio, referred to as the compound's therapeutic index, is typically described as the ratio of the active ingredient's $LD_{50}$ (the amount of compound lethal in 50% of the population) to its $ED_{50}$ (the amount of compound effective in 50% of the population). Typically, a higher therapeutic index for a compound is preferred. Therapeutic index data can be obtained from cell culture assays and/or animal model studies and then used to determine a safe range of dosages of the active ingredient in a pharmaceutical composition for administration to humans. Ideally the dosage determined provides the active ingredient at its $ED_{50}$ level in the subject with little or no toxicity.

Solid form preparations of pharmaceutical compositions can include, for example, powders, tablets, dispersible granules, capsules, cachets, and suppositories. A solid carrier can be one or more substances that can also act as diluents, flavoring agents, solubilizers, lubricants, suspending agents, binders, or tablet disintegrating agents; it can also be an encapsulating material.

In powders, generally the carrier is a finely divided solid that is in an admixture with the finely divided active component, e.g., a disclosed FABP4/5 inhibitor. In tablets, the active ingredient is mixed with the carrier having the necessary binding properties in suitable proportions and compacted in the shape and size desired. The solid form preparation of a pharmaceutical composition of the present disclosure can comprise from about 0.5% to about 10% by weight of a binding agent. Non-limiting examples of binding agents suitable for use in the disclosed compositions are chosen from polyethylene glycol 1500, polyethylene glycol 2000, polyethylene glycol 3000, polyethylene glycol 4000, polyethylene glycol 6000, polyethylene glycol 8000, polyethylene glycol 10000, methylcellulose, ethylcellulose, hydroxymethyl cellulose, hydroxyethylcellulose, hydroxypropyl methylcellulose, polyoxyethylene, copolymers of polyoxyethylene-polyoxypropylene and mixtures thereof. In one embodiment the binding agent is methylcellulose, ethylcellulose, hydroxymethyl cellulose, or hydroxyethylcellulose. In one non-limiting example the binding agent is ethylcellulose.

In some embodiments, the solid compositions can comprise from about 0.5% to about 10% by weight of a carrier. Non-limiting examples of solid carriers include: starch such as tapioca starch, corn starch, potato starch, gelatin, dextrin, inulin, cyclodextrin, oxidized starch, starch ester, starch ether, crosslinked starch, alpha starch, octenyl-succinate ester, and processed starch obtained by treating a starch by an acid, heat, or enzyme, or an emulsifier such as gum arabic, modified starch, pectin, xanthan gum, gum ghatti, gum tragacanth, fenugreek gum, mesquite gum, monoglycerides and di-glycerides of long chain fatty acids, sucrose monoesters, sorbitan esters, polyethoxylated glycerols, stearic acid, palmitic acid, mono-glycerides, di-glycerides, propylene glycol esters, lecithin, lactylated mono- and di-glycerides, propylene glycol monoesters, polyglycerol esters, diacetylated tartaric acid esters of mono- and di-glycerides, citric acid esters of monoglycerides, stearoyl-2-lactylates, polysorbates, succinylated monoglycerides, acetylated monoglycerides, ethoxylated monoglycerides, quillaia, whey protein isolate, casein, soy protein, vegetable protein, pullulan, sodium alginate, guar gum, locust bean gum, tragacanth gum, tamarind gum, carrageenan, furcellaran, Gellan gum, psyllium, curdlan, konjac mannan, agar, and cellulose derivatives, and combinations thereof, or a sugar alcohol that can optionally have humectant properties such as ethylene glycol, glycerol, erythritol, threitol, arabitol, xylitol, ribitol, mannitol, sorbitol, galactitol, frucitol, iditol, sucrose, fructose, isomalt, maltitol, lactitol, sorbitol, dextrose or inositol, and combinations thereof.

The disclosed compositions can comprise from about 25 mg to about 1200 mg of one or more of the disclosed FABP4/5. In one aspect the disclosed single dose compositions of a disclosed FABP4/5 inhibitor can comprise any amount from about 25 mg to about 500 mg.

In a further aspect the disclosed single dose compositions of a disclosed FABP4/5 inhibitor can comprise any amount from about 100 mg to about 500 mg. In a yet further aspect, the disclosed single dose compositions of a disclosed FABP4/5 inhibitor can comprise any amount from about 500 mg to about 1000 mg.

The single dose compositions can comprise any amount of FABP4/5 inhibitor from about 25 mg to about 250 mg. For example, the disclosed compositions can comprise 25 mg, 26 mg, 27 mg, 28 mg, 29 mg, 30 mg 31 mg, 32 mg, 33 mg, 34 mg, 35 mg, 36 mg, 37 mg, 38 mg, 39 mg, 40 mg, 41 mg, 42 mg, 43 mg, 44 mg, 45 mg, 46 mg, 47 mg, 48 mg, 49 mg, 50 mg, 51 mg, 52 mg, 53 mg, 54 mg, 55 mg, 56 mg, 57 mg, 58 mg, 59 mg, 60 mg, 61 mg, 62 mg, 63 mg, 64 mg, 65 mg, 66 mg, 67 mg, 68 mg, 69 mg, 70 mg, 71 mg, 72 mg, 73 mg, 74 mg, 75 mg, 76 mg, 77 mg, 78 mg, 79 mg, 80 mg, 81 mg, 82 mg, 83 mg, 84 mg, 85 mg, 86 mg, 87 mg, 88 mg, 89 mg, 90 mg, 90 mg, 91 mg, 92 mg, 93 mg, 94 mg, 95 mg, 96 mg, 97 mg, 98 mg, 99 mg, 100 mg, 101 mg, 102, mg, 103, mg, 104 mg, 105 mg, 106 mg, 107 mg, 108 mg, 109 mg, 120 mg, 121 mg, 122 mg, 123 mg, 124 mg, 125 mg, 126 mg, 127 mg, 128 mg, 129 mg, 120 mg, 121 mg, 122 mg, 123 mg, 124 mg, 125 mg, 126 mg, 127 mg, 128 mg, 129 mg, 130 mg 31 mg, 132 mg, 133 mg, 134 mg, 135 mg, 136 mg, 137 mg, 138 mg, 139 mg, 140 mg, 141 mg, 142 mg, 143 mg, 144 mg, 145 mg, 146 mg, 147 mg, 148 mg, 149 mg, 150 mg, 151 mg, 152 mg, 153 mg, 154 mg, 155 mg, 156 mg, 157 mg, 158 mg, 159 mg, 160 mg, 161 mg, 162 mg, 163 mg, 164 mg, 165 mg, 166 mg, 167 mg, 168 mg, 169 mg, 170 mg, 171 mg, 172 mg, 173 mg, 174 mg, 175 mg, 176 mg, 177 mg, 178 mg, 179 mg, 180 mg, 181 mg, 182 mg, 183 mg, 184 mg, 185 mg, 186 mg, 187 mg, 188 mg, 189 mg, 190 mg, 190 mg, 191 mg, 192 mg, 193 mg, 194 mg, 195 mg, 196 mg, 197 mg, 198 mg, 199 mg, 200 mg, 201 mg, 202, mg, 203, mg, 204 mg, 205 mg, 206 mg, 207 mg, 208 mg, 209 mg, 210 mg, 212 mg, 212 mg, 213 mg, 214 mg, 215 mg, 216 mg, 217 mg, 218 mg, 219 mg, 220 mg, 221 mg, 222 mg, 223 mg, 224 mg, 225 mg, 226 mg, 227 mg, 228 mg, 229 mg, 230 mg, 231 mg, 232 mg, 233 mg, 234 mg, 235 mg, 236 mg, 237 mg, 238 mg, 239 mg, 240 mg, 241 mg, 242 mg, 243 mg, 244 mg, 245 mg, 246 mg, 247 mg, 248 mg, 249 mg, or 250 mg of one or more of the disclosed FABP4/5 inhibitors.

Liquid forms of the pharmaceutical compositions can include, for example, solutions suitable for oral or parenteral administration, suspensions, and emulsions suitable for oral administration. Sterile water solutions of the active component or sterile solutions of the active component in solvents comprising water, buffered water, saline, PBS, ethanol, or propylene glycol are examples of liquid compositions suitable for parenteral administration. The compositions may contain pharmaceutically acceptable auxiliary substances as required to approximate physiological conditions, such as pH adjusting and buffering agents, tonicity adjusting agents, wetting agents, detergents, and the like. In at least one embodiment, the disclosed liquid compositions can comprise from about 5% to about 25% by weight of a liquid carrier.

For liquid embodiments of the present compositions, the targeted cells, for example, cancer cells or tumor cells can be contacted with an aqueous solution comprising from about 0.5 μg/mL to about 250 μg/mL. In one embodiment the compositions can comprise from about 1 μg/mL to about 100 μg/mL. In another embodiment the compositions can comprise from about 10 μg/mL to about 100 μg/mL. In a further embodiment the compositions can comprise from about 5 μg/mL to about 20 μg/mL. In a yet further embodiment, the compositions can comprise from about 1 μg/mL to about 50 μg/mL. In a yet another embodiment the compositions can comprise from about 1 μg/mL to about 10 μg/mL. In a still further embodiment, the compositions can comprise from about 15 μg/mL to about 50 μg/mL. In still another embodiment the compositions can comprise from about 20 μg/mL to about 200 μg/mL.

The disclosed compositions can provide a single dose of a disclosed FABP4/5 inhibitor based upon the body mass of the subject being treated. Therefore, a single dose of a disclosed FABP4/5 inhibitor can range from about 0.35 mg/kg to about 20 mg/kg of the subject's body mass. In one embodiment, the amount of a disclosed FABP4/5 inhibitor in a single dose is from about 1 mg/kg to about 8 mg/kg of the subject's body mass. In another embodiment, the amount of a disclosed FABP4/5 inhibitor in a single dose is from about 2 mg/kg to about 5 mg/kg of the subject's body mass. In a further embodiment, the amount of a disclosed FABP4/5 inhibitor in a single dose is from about 1.5 mg/kg to about 4 mg/kg of the subject's body mass. In a yet further embodiment, the amount of a disclosed FABP4/5 inhibitor in a single dose is from about 4 mg/kg to about 10 mg/kg of the subject's body mass. In a still further embodiment, the amount of a disclosed FABP4/5 inhibitor in a single dose is from about 5 mg/kg to about 8 mg/kg of the subject's body mass.

For example, the dose can comprise any amount from about 0.5 mg/kg to about 10 mg/kg on the body mass of the subject being treated. For example, 0.5 mg/kg, 0.6 mg/kg, 0.7 mg/kg, 0.8 mg/kg, 0.9 mg/kg, 1 mg/kg, 1.1 mg/kg, 1.2 mg/kg, 1.3 mg/kg, 1.4 mg/kg, 1.5 mg/kg, 1.6 mg/kg, 1.7 mg/kg, 1.8 mg/kg, 1.9 mg/kg, 2.0 mg/kg, 2.1 mg/kg, 2.2 mg/kg, 2.3 mg/kg, 2.4 mg/kg, 2.5 mg/kg, 2.6 mg/kg, 2.7 mg/kg, 2.8 mg/kg, 2.9 mg/kg, 3.0 mg/kg, 3.1 mg/kg, 3.2 mg/kg, 3.3 mg/kg, 3.4 mg/kg, 3.5 mg/kg, 3.6 mg/kg, 3.7 mg/kg, 3.8 mg/kg, 3.9 mg/kg, 4.0 mg/kg, 4.1 mg/kg, 4.2 mg/kg, 4.3 mg/kg, 4.4 mg/kg, 4.5 mg/kg, 4.6 mg/kg, 4.7 mg/kg, 4.8 mg/kg, 4.9 mg/kg, or 50 mg/kg, 5.1 mg/kg, 5.2 mg/kg, 5.3 mg/kg, 5.4 mg/kg, 5.5 mg/kg, 5.6 mg/kg, 5.7 mg/kg, 5.8 mg/kg, 5.9 mg/kg, 6.0 mg/kg, 6.1 mg/kg, 6.2 mg/kg, 6.3 mg/kg, 6.4 mg/kg, 6.5 mg/kg, 6.6 mg/kg, 6.7 mg/kg, 6.8 mg/kg, 6.9 mg/kg, 7.0 mg/kg, 7.1 mg/kg, 7.2 mg/kg, 7.3 mg/kg, 7.4 mg/kg, 7.5 mg/kg, 7.6 mg/kg, 7.7 mg/kg, 7.8 mg/kg, 7.9 mg/kg, 8.0 mg/kg, 8.1 mg/kg, 8.2 mg/kg, 8.3 mg/kg, 8.4 mg/kg, 8.5 mg/kg, 8.6 mg/kg, 8.7 mg/kg, 8.8 mg/kg, 8.9 mg/kg, 90 mg/kg, 9.1 mg/kg, 9.2 mg/kg, 9.3 mg/kg, 9.4 mg/kg, 9.5 mg/kg, 9.6 mg/kg, 9.7 mg/kg, 9.8 mg/kg, 9.9 mg/kg, or 10.0 mg/kg of body mass.

EXAMPLES

Various features and embodiments of the disclosure are illustrated in the following representative examples, which are intended to be illustrative, and not limiting. Those skilled in the art will readily appreciate that the specific examples are only illustrative of the invention as described more fully in the claims which follow thereafter. Every embodiment and feature described in the application should be understood to be interchangeable and combinable with every embodiment contained within.

Example 1: Preparation of 2-((2-((2,4-dichloro-5-isopropoxyphenyl)amino)-2-oxoethyl)thio)acetic acid (Compound B4)

B4

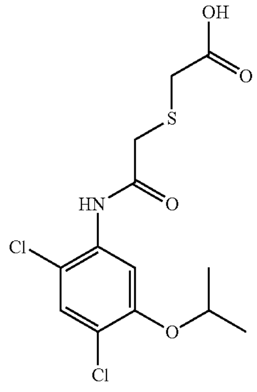 [SMILES: CC(C)Oc1cc(NC(=O)CSCC(=O)O)c(Cl)cc1Cl]

This example illustrates the preparation of the FABP4/5 inhibitor compound B4 via the synthetic method of Scheme 1 as shown below.

Scheme 1

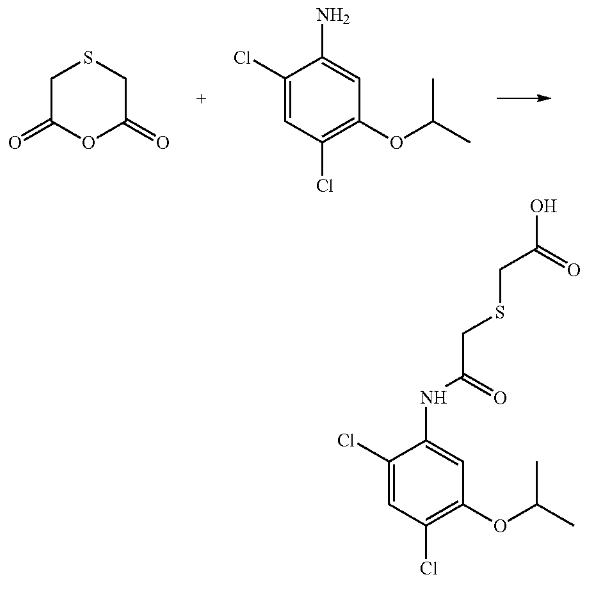

B4

Materials and Methods

To a 25 mL round bottom flask is charged 1,4-oxathiane-2,6-dione (0.821 mmol) and 2,4-dichloro-5-isopropoxyaniline (0.620 mmol. 0.75 eq.). The contents of the flask are dissolved in dry $CH_2Cl_2$ (15 mL) and allowed to stir for 24 hours at room temperature under inert atmosphere. White powder which forms is recovered via rapid cooling recrystallization then isolated via vacuum filtration and washed with cold $CH_2Cl_2$. Residual solvent is removed via rotary evaporation to yield 2-((2-((2,4-dichloro-5-isopropoxyphenyl)-amino)-2-oxoethyl)thio)acetic acid, B4, as a white powder (42 mg, 19.2%).

NMR and HRMS analysis confirmed preparation of the desired product compound. $^1H$ NMR (400 MHz, DMSO-d6) δ: 1.31 ppm (6H, d, J=6.1 Hz), 3.45 (2H, s), 3.54 (2H, s), 4.58 ppm (1H, septet, J=6.1 Hz), 7.62 (1H, s), 7.66 (1H, s), 9.72 (1H, s), 12.68 (1H, s); HRMS (ESI) m/z: 352.01 (63.9), 354.01 (14.1), 353.01 (10.2), 355 (9), 356 (4.5).

Example 2: Preparation of 2-((2-((2,4-dichloro-5-isopropoxyphenyl)amino)-2-oxoethyl)thio)propanoic acid (Compound B102)

B102

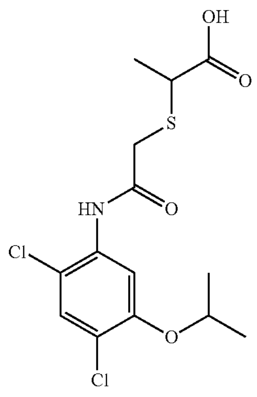 [SMILES: CC(C)Oc1cc(NC(=O)CSC(C)C(=O)O)c(Cl)cc1Cl]

This example illustrates the preparation of the FABP4/5 inhibitor compound B102 via the synthetic method of Scheme 2 as shown below.

Scheme 2

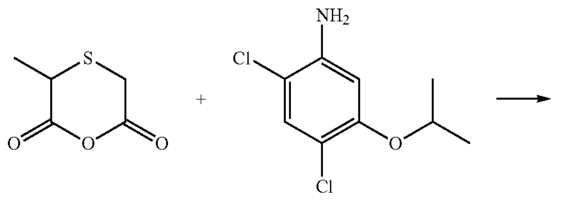

-continued

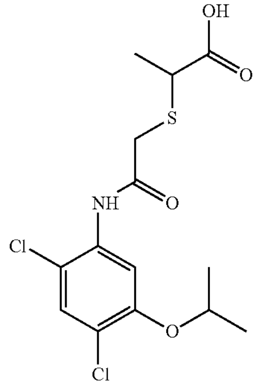

B102

Materials and Methods

To a 25 mL round bottom flask is charged 3-methyl-1,4-oxathiane-2,6-dione (0.486 mmol) and 2,4-dichloro-5-isopropoxyaniline (0.369 mmol, 0.75 eq.). The contents of the flask are dissolved in dry $CH_2Cl_2$ (10 mL) and allowed to stir for 24 hours at room temperature under inert atmosphere. The reaction mixture is stirred for 24 hours at room temperature. The solvent is removed via rotary evaporation. The residue is dissolved in a minimal amount of ethyl acetate and then purified via silica column using a 40-100% gradient of ethyl acetate in hexanes. Fractions containing purified product are identified with silica TLC using a solvent system of 40% ethyl acetate in hexanes with 0.1% acetic acid. Product presence on TLC plate is first identified with PMA stain and then formation of the carboxylic acid is verified with bromocresol green stain. Fractions containing pure B102 are combined, and the product is recovered as a white powder after rotary evaporation (28.4 mg, 21% yield).

NMR analysis confirmed preparation of the desired product compound. $^1H$ NMR (400 MHz): DMSO-$d_6$ δ 1.31 (dd, 6H, J=6.0 Hz), 1.38 (dd, 3H, J=6.11 Hz), 3.45 (m, 1H), 3.59 (m, 2H), 4.58 (septet, 1H, J=12.2 Hz), 7.62 (s, 1H), 7.68 (s, 1H), 9.75 (s, 1H), 12.7 (s, 1H).

Example 3: Preparation of 2-((2-((2,4-dichloro-5-isopropoxyphenyl)amino)-2-oxoethyl)thio)-2-methylpropanoic acid (Compound B104)

B104

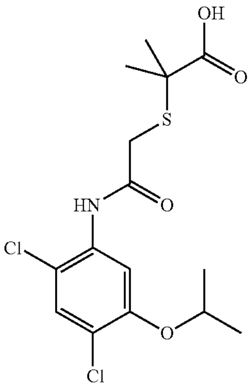 [SMILES: CC(C)Oc1cc(NC(=O)CSC(C)(C)C(=O)O)c(Cl)cc1Cl]

This example illustrates the preparation of the FABP4/5 inhibitor compound B104 via the synthetic method of Scheme 3 as shown below.

Scheme 3

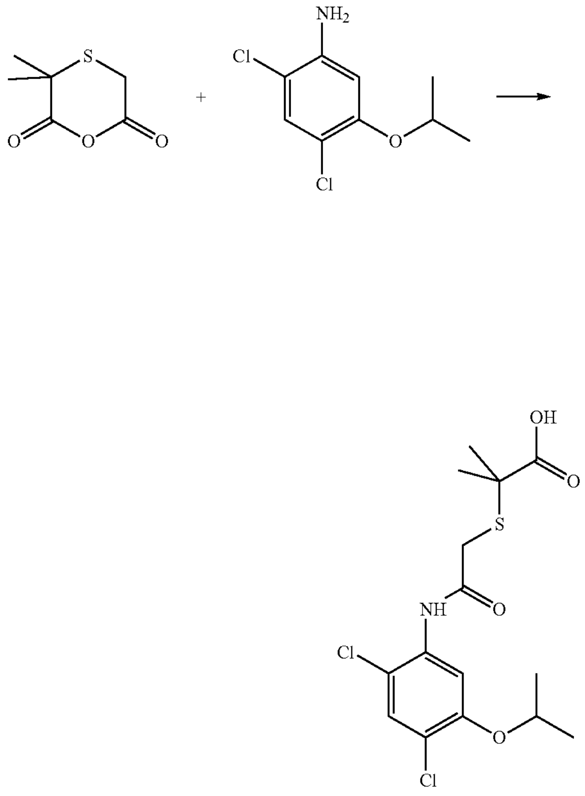

B104

Compound was prepared according to the general method described in Example 1 for the preparation of compound B4. Briefly, to a 25 mL round bottom flask is charged 3,3-dimethyl-1,4-oxathiane-2,6-dione (0.486 mmol) and 2,4-dichloro-5-isopropoxyaniline (0.369 mmol, 0.75 eq.). The content of the flask is dissolved in dry $CH_2Cl_2$ (10 mL) and allowed to stir for 24 hours at room temperature under inert atmosphere. The reaction mixture is stirred for 24 hours at room temperature. The solvent is removed via rotary evaporation. The residue is dissolved in a minimal amount of ethyl acetate and then purified via silica column using a 40-100% gradient of ethyl acetate in hexanes. Fractions containing purified product are identified with silica TLC using a solvent system of 40% ethyl acetate in hexanes with 0.1% acetic acid. Product presence on TLC plate is first identified with PMA stain and then formation of the carboxylic acid is verified with bromocresol green stain. Fractions containing pure B104 are combined, and the product is recovered as a white powder after rotary evaporation (28.4 mg, 21% yield).

NMR analysis confirmed preparation of the desired product compound. $^1H$ NMR (DMSO-$d_6$) 500 Mhz: 12.68 (s, 1H), 9.71 (s, 1H), 7.69 (s, 1H), 7.62 (s, 1H), 4.57 (sept, 1H, J=12.06 Hz), 3.62 (s, 2H), 1.45 (s, 6H), 1.30 (dd, 6H, J=6.02 Hz). $^{13}C$ NMR (DMSO-d $d_6$) 125 Mhz: 174.7, 168.1, 151.7, 134.3, 129.6, 118.6, 116.6, 111.3, 72.1, 47.1, 34.5, 25.4, 21.7

Example 4: Preparation of 2-((1-((2,4-dichloro-5-isopropoxyphenyl)amino)-1-oxopropan-2-yl)thio) propanoic acid (Compound B106)

B106

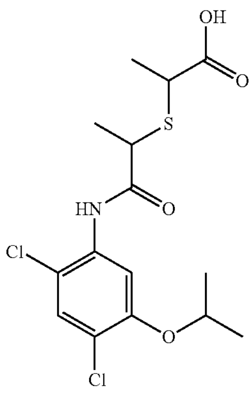 [SMILES: CC(C)Oc1cc(NC(=O)C(C)SC(C)C(=O)O)c(Cl)cc1Cl]

This example illustrates the preparation of the FABP4/5 inhibitor compound B106 via the synthetic method of Scheme 4 as shown below.

Scheme 4

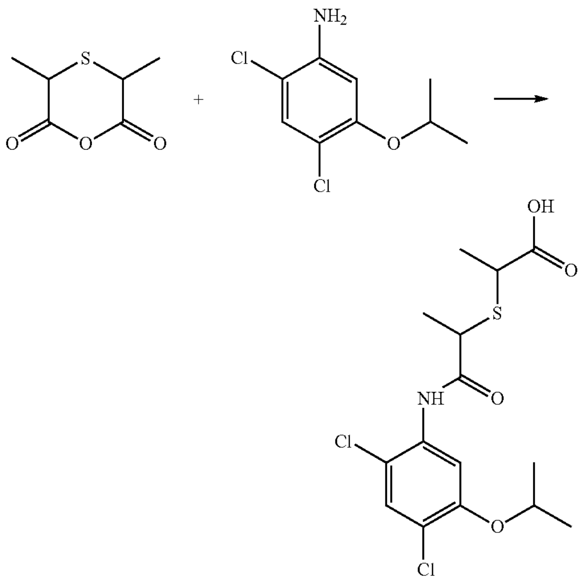

B106

Compound B106 was prepared according to the general method described in Example 2 for the preparation of compound B102. Briefly, to a 25 mL round bottom flask is charged 3,5-dimethyl-1,4-oxathiane-2,6-dione (0.284 mmol) and 2,4-dichloro-5-isopropoxyaniline (0.215 mmol, 0.75 eq.). The contents of the flask are dissolved in dry $CH_2Cl_2$ (10 mL) and allowed to stir for 24 hours at room temperature under inert atmosphere. The reaction mixture is stirred for 24 hours at room temperature. The solvent is removed via rotary evaporation. The residue is dissolved in a minimal amount of ethyl acetate and then purified via silica column using a 40-100% gradient of ethyl acetate in hexanes. Fractions containing purified product are identified with silica TLC using a solvent system of 40% ethyl acetate in hexanes with 0.1% acetic acid. Product presence on TLC plate is first identified with PMA stain and then formation of the carboxylic acid is verified with bromocresol green stain. Fractions containing pure B106 are combined, and the product is recovered as a white powder after rotary evaporation (14.7 mg, 18% yield).

NMR analysis confirmed preparation of the desired product compound. $^1H$ NMR (400 MHz): DMSO-$d_6$ δ 1.31 (dd, 6H, J=5.96), 1.45 (dd, 3H, J=7.01 Hz), 1.54 (dd, 3H, J=6.86 Hz), 3.61 (quartet, 1H, J=7.11 Hz), 3.94 (quartet, 1H, J=7.05 Hz), 4.58 (septet, 1H, J=12.1 Hz), 7.60 (s, 1H), 7.62 (s, 1H), 9.73 (s, 1H), 12.56 (s, 1H).

Example 5: Preparation of 5-((2,4-dichloro-5-isopropoxyphenyl)-carbamoyl)tetrahydrothiophene-2-carboxylic acid (Compound B108)

B108

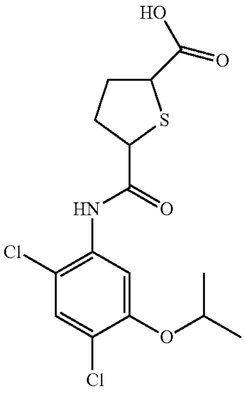

This example illustrates the preparation of the FABP4/5 inhibitor compound B108 via the synthetic method of Scheme 5 as shown below.

Scheme 5

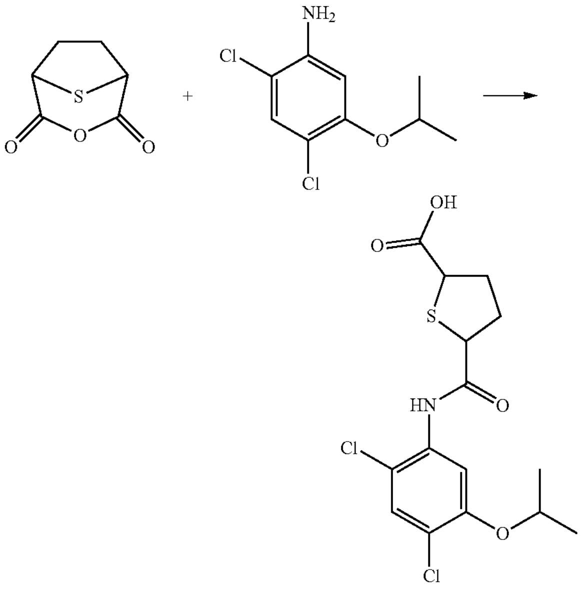

B108

Compound B108 was prepared according to the general method described in Example 2 for the preparation of compound B102. Briefly, to a 25 mL round bottom flask is charged 3-oxa-8-thiabicyclo[3.2.1]octane-2,4-dione (0.331 mmol) and 2,4-dichloro-5-isopropoxyaniline (0.254 mmol, 0.75 eq.). The contents of the flask are dissolved in dry $CH_2Cl_2$ (10 mL) and allowed to stir for 24 hours at room temperature under inert atmosphere. The reaction mixture is stirred for 24 hours at room temperature. The solvent is removed via rotary evaporation. The residue is dissolved in a minimal amount of ethyl acetate and then purified via silica column using a 40-100% gradient of ethyl acetate in hexanes. Fractions containing purified product are identified with silica TLC using a solvent system of 40% ethyl acetate in hexanes with 0.1% acetic acid. Product presence on TLC plate is first identified with PMA stain and then formation of the carboxylic acid is verified with bromocresol green stain. Fractions containing pure B108 are combined, and the product is recovered as a white powder after rotary evaporation (17 mg, 17.6% yield).

NMR analysis confirmed preparation of the desired product compound. $^1H$ NMR (500 MHz), DMSO-$d_6$: 12.64 (s, 1H), 9.69 (s, 1H), 7.68 (s, 1H), 7.61 (s, 1H), 4.58 (septet, 1H, J=12.07 Hz), 4.24 (t, 1H, J=11.97 Hz), 4.04 (t, 1H, J=12.6 Hz), 2.4-1.91 (m, 4H), 1.31 (dd, 6H, J=6.0 Hz); $^{13}C$ NMR (125 MHz), DMSO-$d_6$: 173.8, 171.07, 152.2, 134.8, 130.0, 119.2, 117.3, 111.8, 72.3, 50.8, 49.35, 33.9, 33.17, 22.07.

Example 6: Preparation of 2-(2-((2,4-dichloro-5-isopropoxyphenyl)amino)-2-oxoethoxy)acetic acid (Compound B110)

B110

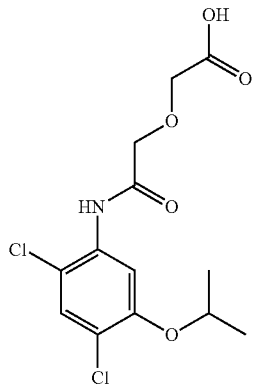

This example illustrates the preparation of the FABP4/5 inhibitor compound B110 via the synthetic method of Scheme 6 as shown below.

Scheme 6

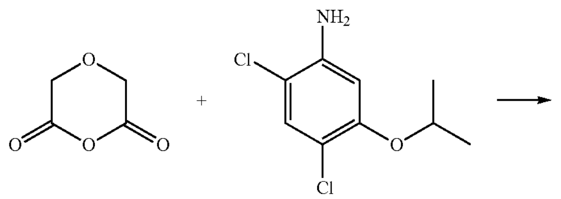

-continued

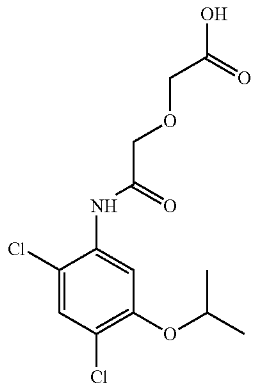

B110

Compound B110 was prepared according to the general method described in Example 1 for the preparation of compound B4. Briefly, to a 25 mL round bottom flask is charged 1,4-dioxane-2.6-dione (0.922 mmol) and 2,4-dichloro-5-isopropoxyaniline (0.922 mmol). The contents of the flask are dissolved in dry $CH_2Cl_2$ (10 mL) and allowed to stir for 24 hours at room temperature under inert atmosphere. Solvent is removed via rotary evaporation and the residual contents are then dissolved in fresh CH2Cl2. A white powder forms upon rapid cooling recrystallization and is recovered via filtration. Residual solvent is removed via rotary evaporation to yield 2-(2-((2,4-dichloro-5-isopropoxyphenyl)amino)-2-oxoethoxy)acetic acid, B110, as a white powder (56 mg, 16.8%).

NMR analysis confirmed preparation of the desired product compound. $^1H$ NMR (500 MHz), DMSO-$d_6$: 12.91 (s, 1H), 9.46 (s, 1H), 7.88 (s, 1H), 7.65 (s, 1H), 4.58 (septet, 1H, J=12.09 Hz), 4.25 (s, 2H), 4.23 (s, 2H), 1.31 (dd, 6H, J=6.03 Hz).

Example 7: Preparation of 5-((2,4-dichloro-5-isopropoxyphenyl)carbamoyl)tetrahydrofuran-2-carboxylic acid (Compound B112)

B112

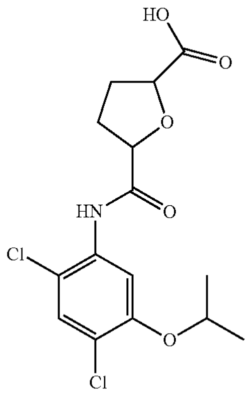

This example illustrates the preparation of the FABP4/5 inhibitor compound B112 via the synthetic method of Scheme 7 as shown below.

Scheme 7

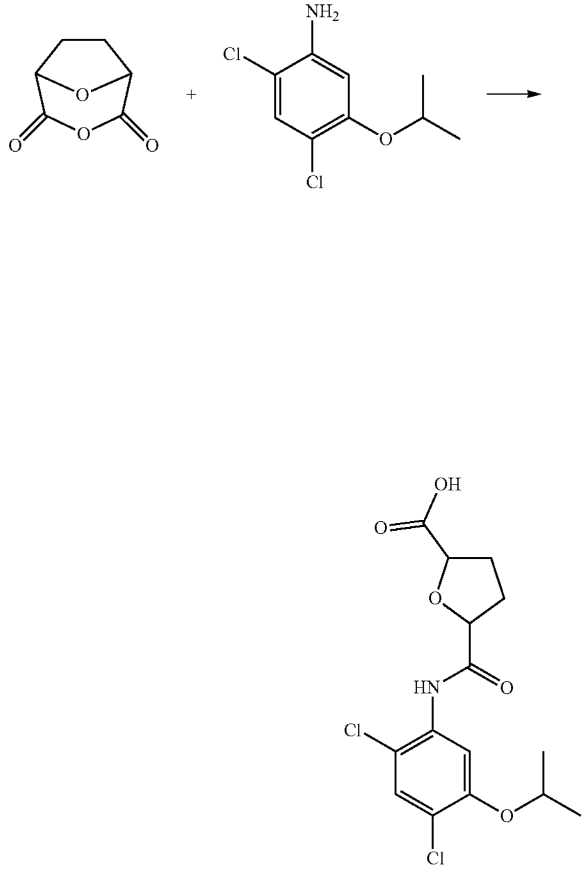

B112

Compound B112 was prepared according to the general method described in Example 1 for the preparation of compound B4. Briefly, to a 25 mL round bottom flask is charged 3,8-dioxabicyclo[3.2.1]octane-2,4-dione (0.180 mmol) and 2,4-dichloro-5-isopropoxyaniline (0.150 mmol). The contents of the flask are dissolved in dry $CH_2Cl_2$ (10 mL) and allowed to stir for 24 hours at room temperature under inert atmosphere. Solvent is removed via rotary evaporation and the residual contents are then dissolved in fresh EtOAc. A white powder forms upon rapid cooling recrystallization and is recovered via filtration. Residual solvent is removed via rotary evaporation to yield 5-((2,4-dichloro-5-isopropoxyphenyl)carbamoyl)tetrahydrofuran-2-carboxylic acid, B112, as a white powder (22 mg, 40.5%).

NMR analysis confirmed preparation of the desired product compound. $^1H$ NMR (500 MHz), DMSO-$d_6$: 13.26 (s, 1H), 9.99 (s, 1H), 8.01 (s, 1H), 7.65 (s, 1H), 4.65 (m, 1H), 4.62-4.54 (m, 2H), 2.39-2.30 (m, 2H), 2.04-2.00 (m, 2H), 1.31 (dd, 6H, J=6.0 Hz).

Example 8: Preparation of 5-((2,4-dichloro-5-isopropoxyphenyl)amino)-5-oxopentanoic acid (Compound B114)

B114

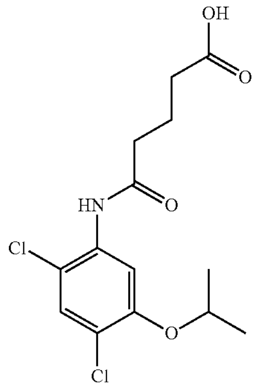

This example illustrates the preparation of the FABP4/5 inhibitor compound B114 via the synthetic method of Scheme 8 as shown below.

Scheme 8

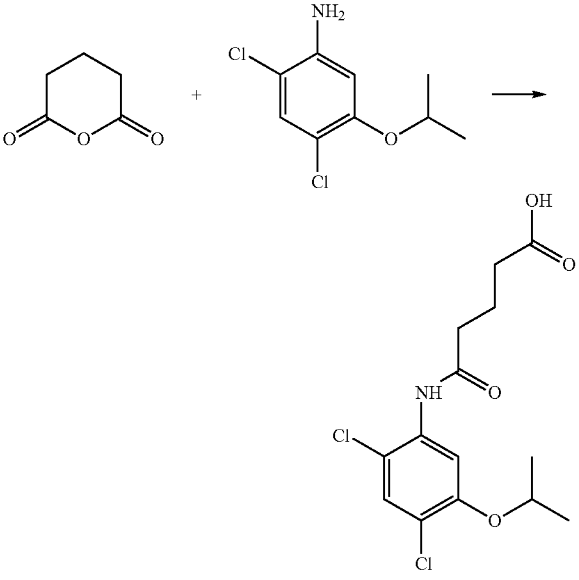

B114

Compound B114 was prepared according to the general method described in 1 for the preparation of compound B4. Briefly, to a 25 mL round bottom flask is charged dihydro-2H-pyran-2,6(3H)-dione (1.05 mmol) and 2,4-dichloro-5-isopropoxyaniline (0.747 mmol, 0.75 eq.). The contents of the flask are dissolved in dry $CH_2Cl_2$ (10 mL) and allowed to stir for 24 hours at room temperature under inert atmosphere. Solvent is removed via rotary evaporation and the residual contents are then dissolved in fresh CH2Cl2. A white powder forms upon rapid cooling recrystallization and is recovered via filtration. Residual solvent is removed via rotary evaporation to yield 5-((2,4-dichloro-5-isopropoxyphenyl)amino)-5-oxopentanoic acid, B114, as a white powder (80 mg, 32%).

NMR analysis confirmed preparation of the desired product compound. $^1$H NMR (400 MHz): DMSO-$d_6$ δ 1.05 (m, 3H), 1.11 (m, 3H), 1.30 (dd, 6H, J=6.0 Hz), 2.29 (m, 2H), 2.33 (m, 2H), 4.58 (septet, 1H, J=12.02 Hz), 7.57 (s, 1H), 7.60 (s, 1H), 9.49 (s, 1H), 12.05 (s, 1H).

Example 9: Preparation of 5-((2,4-dichloro-5-isopropoxyphenyl)amino)-3,3-dimethyl-5-oxopentanoic acid (Compound B116)

B116

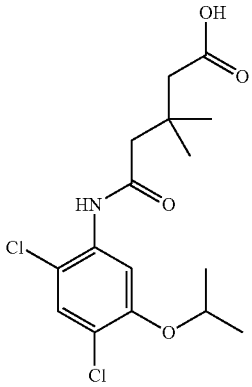

This example illustrates the preparation of the FABP4/5 inhibitor compound B116 via the synthetic method of Scheme 9 as shown below.

Scheme 9

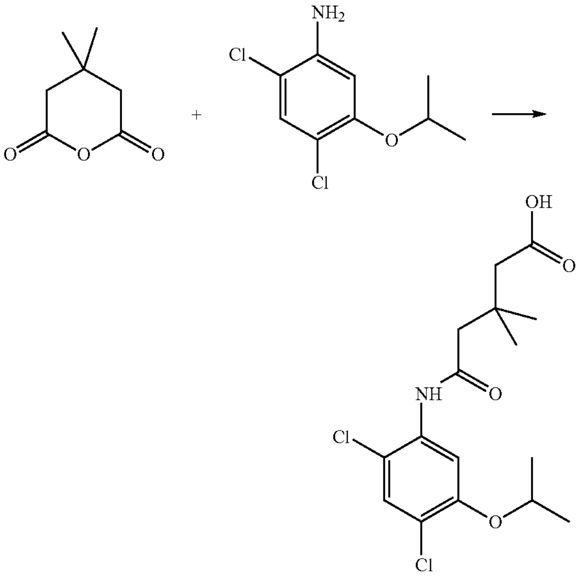

B116

Compound B116 was prepared according to the general method described in Example 2 for the preparation of compound B102. Briefly, to a 25 mL round bottom flask is charged 4,4-dimethyldihydro-2H-pyran-2,6(3H)-dione (0.540 mmol) and 2,4-dichloro-5-isopropoxyaniline (0.322 mmol, 0.75 eq.). The contents of the flask are dissolved in dry $CH_2Cl_2$ (10 mL) and allowed to stir for 24 hours at room temperature under inert atmosphere. The solvent is removed via rotary evaporation. The residue is dissolved in a minimal amount of ethyl acetate and then purified via silica column using a 40-100% gradient of ethyl acetate in hexanes. Fractions containing purified product are identified with silica TLC using a solvent system of 40% ethyl acetate in hexanes with 0.1% acetic acid. Product presence on TLC plate is first identified with PMA stain and then formation of the carboxylic acid is verified with bromocresol green stain. Fractions containing pure B116 are combined, and the product is recovered as a yellow oil after rotary evaporation (7.5 mg, 6.4%).

NMR analysis confirmed preparation of the desired product compound. $^1$H NMR (400 MHz): DMSO-$d_6$ δ 1.05 (m, 3H), 1.11 (m, 3H), 1.30 (dd, 6H, J=6.0 Hz), 2.29 (m, 2H), 2.33 (m, 2H), 4.58 (septet, 1H, J=12.02 Hz), 7.57 (s, 1H), 7.60 (s, 1H), 9.49 (s, 1H), 12.05 (s, 1H).

Example 10: Preparation of 2-(1-(2-((2,4-dichloro-5-isopropoxyphenyl)amino)-2-oxoethyl)cyclopentyl) acetic acid (Compound B118)

B118

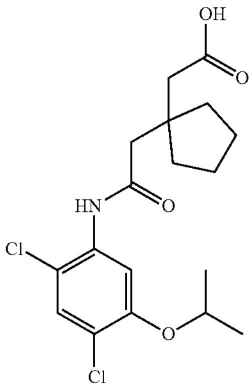

This example illustrates the preparation of the FABP4/5 inhibitor compound B118 via the synthetic method of Scheme 10 as shown below.

Scheme 10

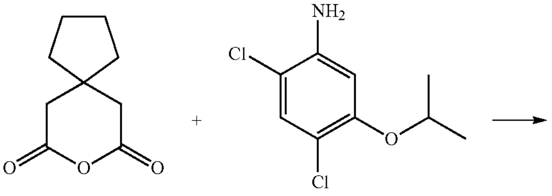

-continued

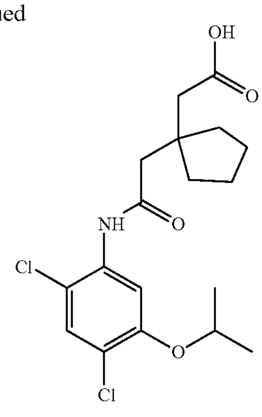

B118

Compound B118 was prepared according to the general method described in Example 2 for the preparation of compound B102. Briefly, to a 25 mL round bottom flask is charged 8-oxaspiro[4.5]decane-7,9-dione (0.320 mmol) and 2,4-dichloro-5-isopropoxyaniline (0.240 mmol, 0.75 eq.). The contents of the flask are dissolved in dry $CH_2Cl_2$ (10 mL) and allowed to stir for 24 hours at room temperature under inert atmosphere. The solvent is removed via rotary evaporation. The residue is dissolved in a minimal amount of ethyl acetate and then purified via silica column using a 40-100% gradient of ethyl acetate in hexanes. Fractions containing purified product are identified with silica TLC using a solvent system of 40% ethyl acetate in hexanes with 0.1% acetic acid. Product presence on TLC plate is first identified with PMA stain and then formation of the carboxylic acid is verified with bromocresol green stain. Fractions containing pure B118 are combined, and the product is recovered as a yellow oil after rotary evaporation (3.8 mg, 4.1%).

NMR analysis confirmed preparation of the desired product compound. $^1H$ NMR (400 MHz): DMSO-$d_6$ $\delta$ 1.30 (dd, 6H, J=6.01 Hz), 1.63-1.55 (m, 8H), 2.40 (m, 2H), 2.46 (m, 2H), 4.58 (septet, 1H, J=12.03 Hz), 7.59 (s, 2H), 9.47 (s, 1H), 12.08 (s, 1H).

Example 11: Preparation of 2-((2-((2,4-dichloro-5-ethoxyphenyl)amino)-2-oxoethyl)thio)acetic acid (Compound B120)

B120

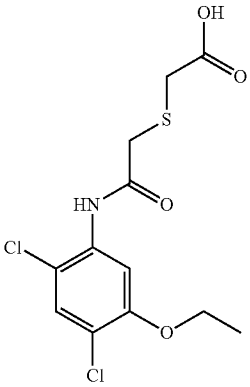

This example illustrates the preparation of the FABP4/5 inhibitor compound B120 via the synthetic method of Schemes 11A and 11B as shown below.

Scheme 11A

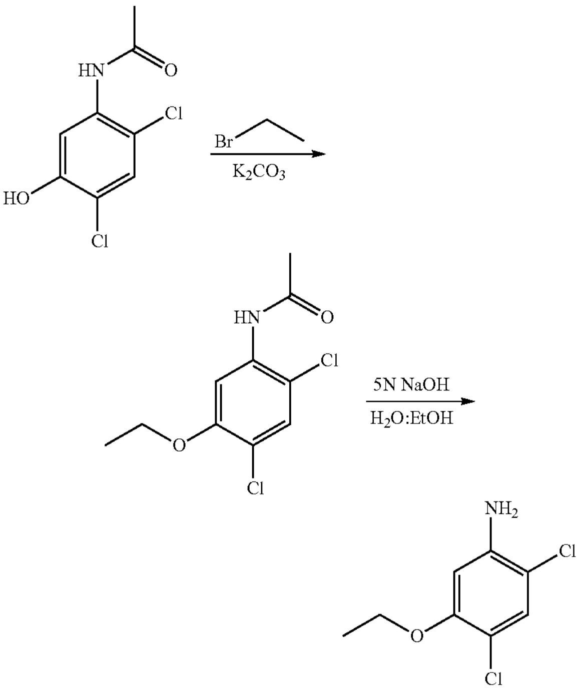

Scheme 11B

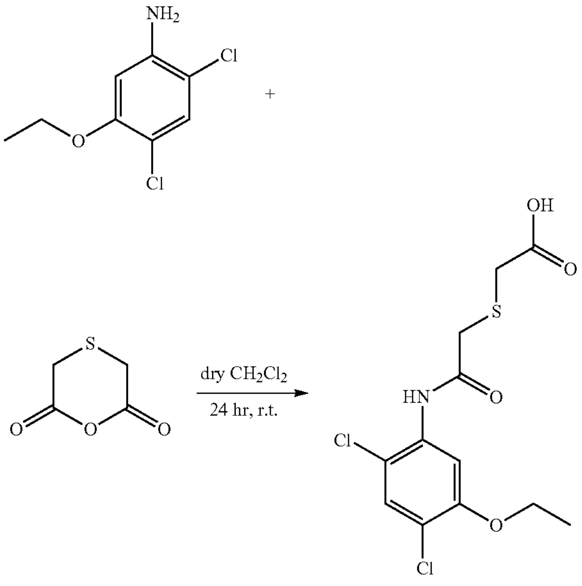

B120

A. Preparation of 2,4-dichloro-5-ethoxyaniline: To a round bottom flask is charged N-(2,4-dichloro-5-hydroxyphenyl)acetamide (0.235 mmol), bromoethane (0.353 mmol, 1.5 eq.) and potassium carbonate (0.353 mmol, 1.5 eq). The contents of the flask are dissolved in a mixture of 10 mL acetone: 10 mL $ddH_2O$ and refluxed for 4 hours. The reaction was cooled, extracted with ethyl acetate, washed with brine, and dried over anhydrous sodium sulfate. The solvent is removed with rotary evaporation. The resulting product is dissolved in 5 mL EtOH and 7 mL dd $H_2O$. 3 mL of 5N NaOH is added, and the mixture is allowed to reflux for 2 h. The mixture is allowed to stir at room temperature overnight and then brought back to reflux for 1 hour the following morning. The reaction mixture is cooled, and ethanol is removed via rotary evaporation. The crude mixture is extracted with dichloromethane, washed with brine, and dried over anhydrous sodium sulfate. Solvent is removed via rotary evaporation to yield 2,4-dichloro-5-ethoxyaniline (14 mg, 29.2%) as a light-yellow oil.

B. Preparation of B120: To a round bottom flask is charged 2,4-dichloro-5-ethoxyaniline (0.068 mmol, 0.75 eq.) and 1,4-oxathiane-2,6-dione (0.091 mmol, 1 eq.). The compounds are dissolved in dry $CH_2Cl_2$ and allowed to stir at room temperature for 24 h under inert atmosphere. A white precipitate is collected via filtration and purified via rapid cooling recrystallization in dichloromethane to yield B120 (8 mg, 34.9%, 10.2% overall).

NMR analysis confirmed preparation of the desired product compound. 1H NMR (500 MHz): DMSO-d6 δ 1.36 (t, 3H, J=6.95 Hz), 3.45 (s, 2H), 3.53 (s, 2H), 4.08 (quartet, 2H, J=6.96 Hz), 7.62 (s, 1H), 7.66 (s, 1H), 9.72 (s, 1H), 12.67 (s, 1H).

Example 12: Preparation of 2-((2-((5-(tert-butoxy)-2,4-dichlorophenyl)amino)-2-oxoethyl)thio)acetic acid (Compound B121)

B121

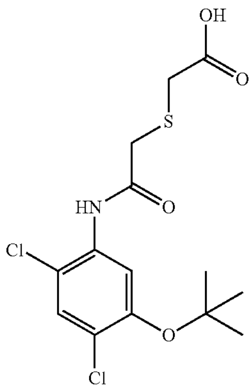

This example illustrates the preparation of the FABP4/5 inhibitor compound B121 via the synthetic method of Scheme 12 as shown below.

Scheme 12A

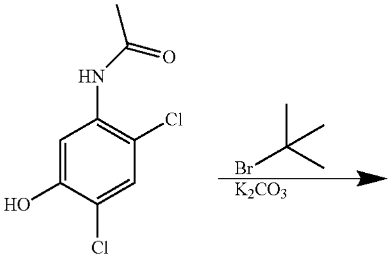

-continued

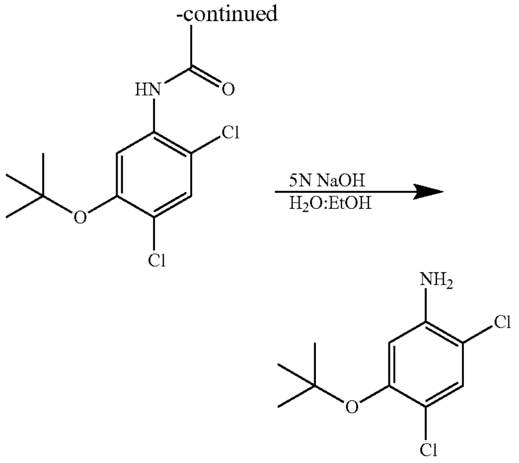

Scheme 12B

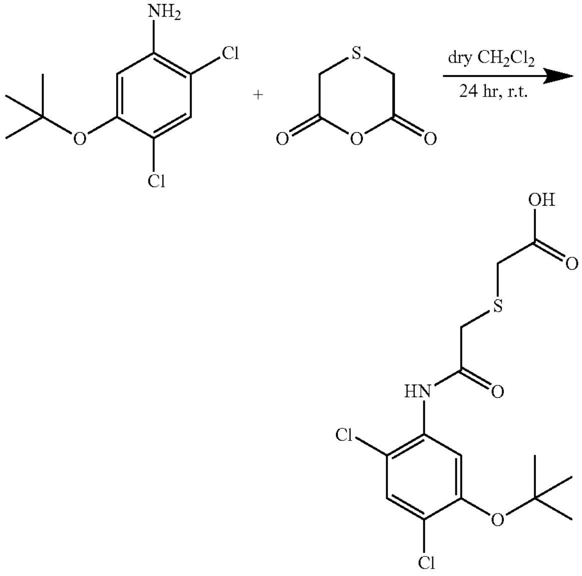

A. Preparation of 5-(tert-butoxy)-2,4-dichloroaniline: To a round bottom flask is charged N-(2,4-dichloro-5-hydroxyphenyl)acetamide (0.186 mmol), 2-bromo-2-methylpropane (0.279 mmol, 1.5 eq.) and potassium carbonate (0.279 mmol, 1.5 eq). The contents of the flask are dissolved in a mixture of 10 mL acetone: 10 mL $ddH_2O$ and refluxed for 4 hours. The reaction was cooled, extracted with ethyl acetate, washed with brine, and dried over anhydrous sodium sulfate. The solvent is removed with rotary evaporation. The resulting product is dissolved in 5 mL EtOH and 7 mL $ddH_2O$. 3 mL of 5N NaOH is added, and the mixture is allowed to reflux for 2 h. The mixture is allowed to stir at room temperature overnight and then brought back to reflux for 1 hour the following morning. The reaction mixture is cooled, and ethanol is removed via rotary evaporation. The crude mixture is extracted with dichloromethane, washed with brine, and dried over anhydrous sodium sulfate. Solvent is removed via rotary evaporation to yield 5-(tert-butoxy)-2,4-dichloroaniline (14 mg, 32.3%) as a colorless oil.

B. Preparation of B121: To a round bottom flask is charged 5-(tert-butoxy)-2,4-dichloroaniline (0.054 mmol, 0.75 eq.) and 1,4-oxathiane-2,6-dione (0.09 mmol, 1 eq.). The compounds are dissolved in dry CH2C12 and allowed to stir at room temperature for 24 h under inert atmosphere. A white precipitate is collected via filtration and purified via rapid cooling recrystallization in dichloromethane to yield B121 (5 mg, 23.1%, 7.5% overall.

Example 13: Preparation of 2-((2-((2,4-dichloro-5-propoxyphenyl)amino)-2-oxoethyl)thio)acetic acid (Compound B122)

B122

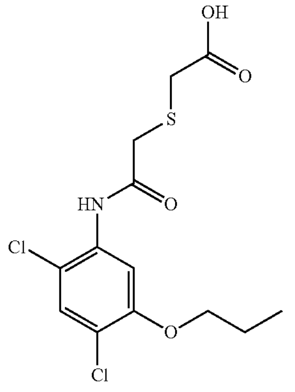

This example illustrates the preparation of the FABP4/5 inhibitor compound B122 via the proposed synthetic method of Scheme 13 as shown below.

Scheme 13

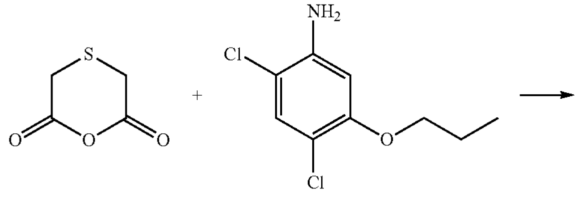

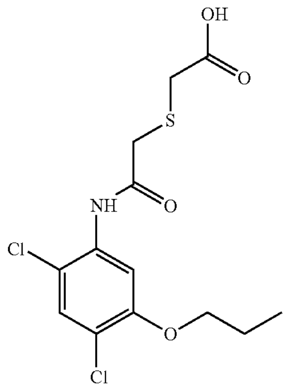

B122

B122 is prepared using the general synthetic method for B120 described in Example 11 except that 0.75 eq of the aniline reagent 2,4-dichloro-5-propoxyaniline is used instead of 2,4-dichloro-5-ethoxyaniline.

Example 14: Preparation of 2-((2-((2,4-dichloro-5-cyclopropoxyphenyl)amino)-2-oxoethyl)thio)acetic acid (Compound B123)

B123

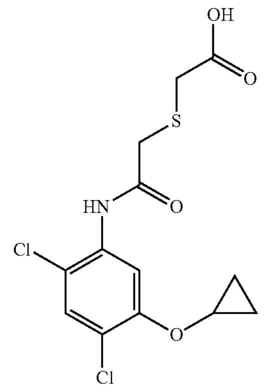

This example illustrates the preparation of the FABP4/5 inhibitor compound B123 via the proposed synthetic method of Scheme 14 as shown below.

Scheme 14

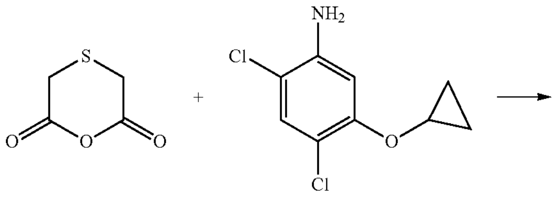

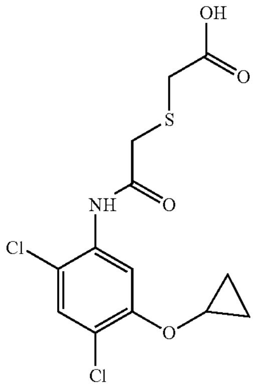

B123

B123 is prepared using the general synthetic method for B120 described in Example 11 except that 0.75 eq of the aniline reagent 2,4-dichloro-5-cyclopropoxyaniline was used instead of 2,4-dichloro-5-ethoxyaniline. Example 15: Preparation of 2-((2-((2,4-dichloro-5-isobutoxyphenyl)amino)-2-oxoethyl)thio)acetic acid (compound B124)

B124

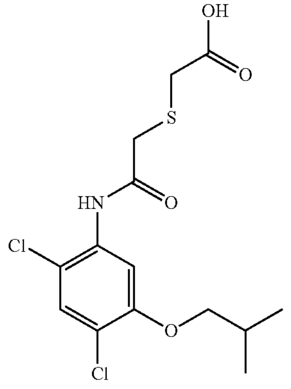

This example illustrates the preparation of the FABP4/5 inhibitor compound B124 via the proposed synthetic method of Scheme 15 as shown below.

Scheme 15

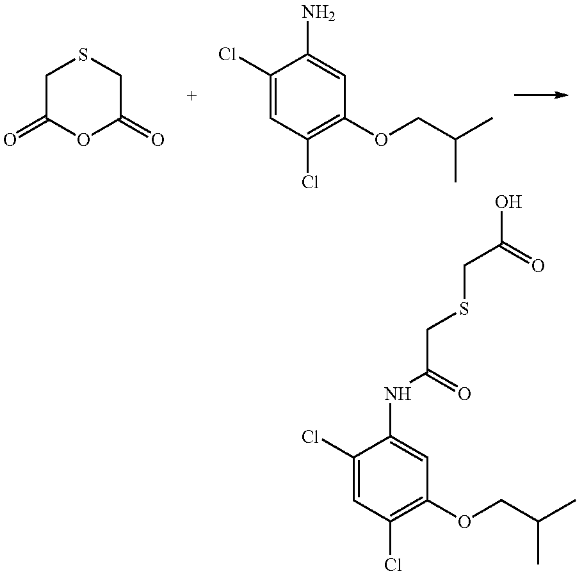

B124

B124 is prepared using the general synthetic method for B120 described in Example 11 except that 0.75 eq of the aniline reagent 2,4-dichloro-5-isopropoxyaniline is used instead of 2,4-dichloro-5-ethoxyaniline.

Example 16: FABP Binding Assay of Inhibitor Compounds

This example illustrates a binding assay study used to determine the binding affinity of the various inhibitor compounds disclosed herein with the various FABPs: FABP3, FABP4, FABP5 and FABP7.

Materials and Methods

Binding assays for FABP3, FABP4, FABP5 and FABP7 were carried out by fluorescence titrations. FABPs were bacterially expressed and purified and the equilibrium dissociation constants (Kd) that characterize their interactions with different compounds were measured by fluorescence competition assays. The method entails two steps as described in e.g., Lin, Q. et al., "Ligand selectivity of the peroxisome proliferator-activated receptor alpha," *Biochemistry* 38, 185-190, doi:10.1021/bi9816094 bi9816094 [pii] (1999). In the first step, Kd for the association of the protein with the fluorescent fatty acid probe ANS was measured. Protein (2 M) was titrated with ANS from a concentrated solution in DMSO. Ligand binding was monitored by following the increase in the fluorescence of the ligand upon binding to the protein, and Kd for the association of ANS with the each FABP was computed from titration curves as described in e.g., Norris, A. W. & Li, E., "Fluorometric titration of the CRABPs," *Methods Mol Biol* 89, 123-139 (1998)). Kds for binding of non-fluorescent ligands were then measured by monitoring their ability to displace ANS in the binding pocket of the protein. Each FABP was pre-complexed with ANS at 1:1 molar ratio and titrated with the different compounds whose binding was reflected by a decrease in probe fluorescence. Kds were extracted from the EC50 of the competition curve and the measured Kd for ANS.

Results

The following Table 8 shows the results of FABP5 and FABP4 binding assays of the disclosed compounds B4, B102, B104, B106, B108, B110, B112, B114, B116, and B118.

TABLE 8

| Compound | FABP5 binding | FABP4 binding |
|---|---|---|
| 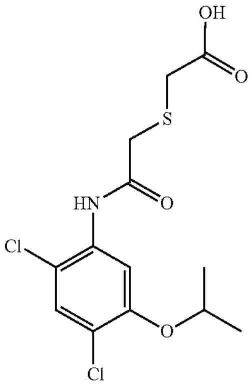 2-((2-((2,4-dichloro-5-isopropoxyphenyl)amino)-2-oxoethyl)thio)acetic acid (B4) | 36 nM | 66 nM |

TABLE 8-continued

| Compound | FABP5 binding | FABP4 binding |
|---|---|---|
| 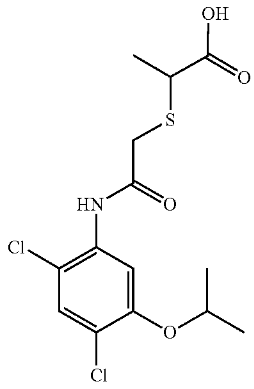 2-((2-((2,4-dichloro-5-isopropoxyphenyl)amino)-2-oxoethyl)thio)propanoic acid (B102) | 6 nM | 116 nM |
| 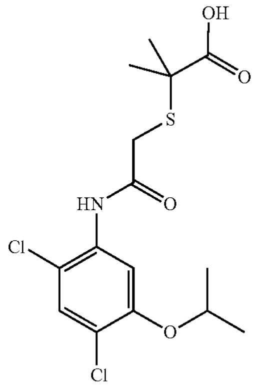 2-((2-((2,4-dichloro-5-isopropoxyphenyl)amino)-2-oxoethyl)thio)-2-methylpropanoic acid (B104) | 7 nM | 97 nM |
| 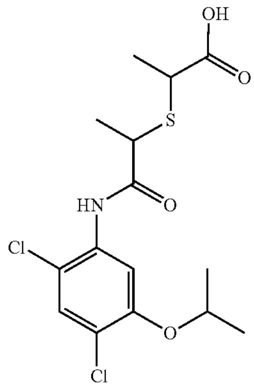 2-((1-((2,4-dichloro-5-isopropoxyphenyl)amino)-1-oxopropan-2-yl)thio)propanoic acid (B106) | 15 nM | 286 nM |
| 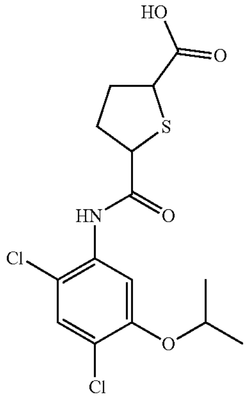 [SMILES: CC(C)Oc1cc(NC(=O)C2CCC(C(=O)O)S2)c(Cl)cc1Cl] 5-((2,4-dichloro-5-isopropoxyphenyl)-carbamoyl)tetrahydrothiophene-2-carboxylic acid (B108) | 2 nM | 48 nM |
| 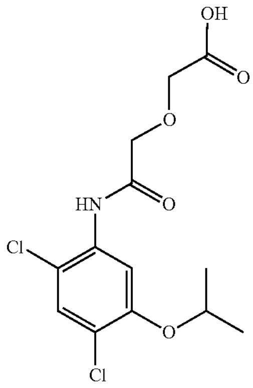 [SMILES: CC(C)Oc1cc(NC(=O)COCC(=O)O)c(Cl)cc1Cl] 2-(2-((2,4-dichloro-5-isopropoxyphenyl)amino)-2-oxoethoxy)acetic acid (B110) | 15 nM | 242 nM |
| 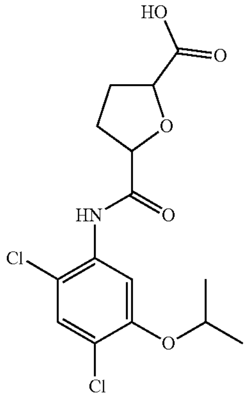 [SMILES: CC(C)Oc1cc(NC(=O)C2CCC(C(=O)O)O2)c(Cl)cc1Cl] 5-((2,4-dichloro-5-isopropoxyphenyl)carbamoyl)tetrahydrofuran-2-carboxylic acid (B112) | 15 nM | 116 nM |

TABLE 8-continued

| Compound | FABP5 binding | FABP4 binding |
|---|---|---|
| 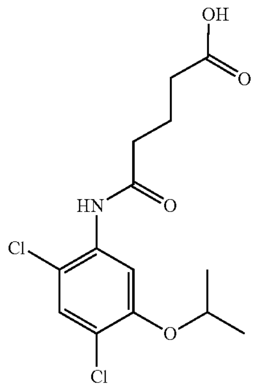 [SMILES: CC(C)Oc1cc(NC(=O)CCCC(=O)O)c(Cl)cc1Cl] 5-((2,4-dichloro-5-isopropoxyphenyl)amino)-5-oxopentanoic acid (B114) | 6 nM | 218 nM |
| 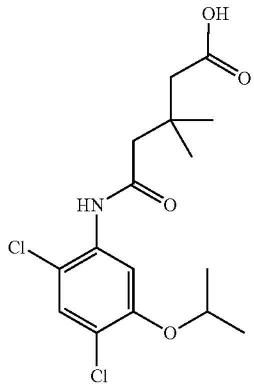 [SMILES: CC(C)Oc1cc(NC(=O)CC(C)(C)CC(=O)O)c(Cl)cc1Cl] 5-((2,4-dichloro-5-isopropoxyphenyl)amino)-3,3-dimethyl-5-oxopentanoic acid (B116) | 3 nM | 90 nM |
| 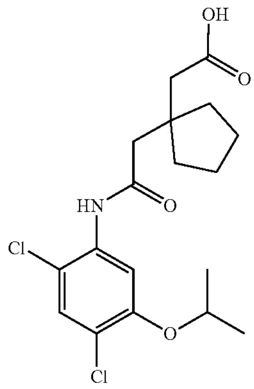 [SMILES: CC(C)Oc1cc(NC(=O)CC2(CC(=O)O)CCCC2)c(Cl)cc1Cl] 2-(1-(2-((2,4-dichloro-5-isopropoxyphenyl)amino)-2-oxoethyl)cyclopentyl) acetic acid (B118) | 2 nM | 78 nM |

Example 17: Biological Studies of FABP4/5 Inhibitor Compounds B4, B7 and B9

This example illustrates studies of the biological function of the FABP4/5 inhibitor compounds B4, B7 and B9, which have a diverse of structures based on the 5-position moiety.

Materials and Methods

A. Binding Assays for FABPs

Binding assays for FABP3, FABP4, FABP5 and FABP7 were carried out by fluorescence titrations as described in Example 16.

B. Cells Used

COS-7, MDA-MB-231, HepG2, LX-2, 3T3-L1, RAW 246.7, and MCF7 were cultured in Dulbecco's modified Eagle's medium (DMEM) supplemented with 10% fetal bovine serum (Invitrogen Life Sciences, Carlsbad, CA). MDA-MB-157 and MB-549 cells were cultured in L-Glutamine containing RPMI medium supplemented with 10% fetal calf serum (Invitrogen Life Sciences, Carlsbad, CA).

C. Transactivation Assays

COS-7 were cultured in 6-well plates and co-transfected with either a luciferase reporter driven by 3 copies of a PPRE and expression vector for either PPARδ, PPARα or PPARγ together with a vector harboring cDNA for β-galactosidase, serving as a transfection control. To test whether FABP4 or FABP5 mediate activation of their cognate receptors PPARγ and PPARδ, respectively, cells were also co-transfected with a plasmid harboring sequence of either FABP4 or FABP5. 18 h post-transfection, cells were placed in a serum-free medium and treated with agonist/compound. 18 h. later, cells were lysed, luciferase activity was assayed (Promega, WI, USA) and corrected for transfection efficiency by the activity of β-galactosidase.

D. Real-Time PCR

Cells were treated with a compound for 6 h. then lysed and RNA was extracted using Trizol, according to the manufacturer's instructions. cDNA was generated using GeneAmp RNA PCR (Applied Biosystems). qPCR was carried out using TaqMan chemistry and Assays-on-Demand probes (Applied Biosystems). 18s (4352930) rRNA was used for normalization. Relative expression was calculated as $2^{-\Delta\Delta CT}$.

E. Proliferation Assays 2000 cells were plated in each well of 96-well plate. The next day cells were treated with compounds and incubated in Incucyte for 4 days. Images taken every 4 hours for the duration of the time were analyzed to calculate percentage of confluency in response to the treatments. Growth inhibition was calculated as 1−(percentage of viable cells out of untreated cells).

F. Immunoblots

Cells were treated with compounds for 18 h. then total cell protein was extracted using RIPA buffer (25 mM Tris-HCl, 150 mM NaCl, 1% NP40, 1% sodium deoxycholate, 0.1%

SDS). Proteins were resolved by electrophoresis on SDS-PAGE gels and transferred onto nitrocellulose membrane. Membranes were incubated with primary antibodies, followed by washes with Tween-TBS, and incubation with HRP conjugated antibodies. Protein expression was detected by exposure to ECL and exposed to XR-B x-ray film. Band intensities were quantified using ImageJ 1.40 g software (Wayen Rasband, NIH, USA).

G. Lipid Uptake Assays

1) LX-2: Human LX-2 hepatic stellate cells were treated with compound for 2 days in the presence or absence of 2% lipid mixture (Sigma, USA) in the growth media. Cells were stained with Oil Red O and lipid content was quantified using ImageJ.

2) Hepg2 cells: 5000 cells were plated in 96-well plate. The next day cells were treated with tested compounds for 4 hours and then treated with 1 mM oleic acid for additional 24 hours. Cells were then stained with Nile Red and Dapi and lipid content was quantified using Cytation5 (Agilent).

3) 3T3-L1: Mouse 3T3-L1 cells were differentiated in culture according to ATCC protocol to become mature adipocytes. At day 6 of the differentiation, compound treatment started. Cells were stained by Nile Red on day and color intensity in each cell was measured relative to Dapi staining. Lipolysis was measured by measuring glycerol levels using lipolysis kit (Cayman, USA) according to the manufacturer manual.

H. Hepatic Stellate Cells Activation Assay

LX-2 cells were treated with compound for 6 h. then stimulated with TGF-β (4 ng/μl) for additional 24 h. Cells were fixed with 4% paraformaldehyde and immununostained with the fibrosis marker αSMA. Nuclei were stained with Dapi. Images and quantification of positive cells was done using Cytation5 (Agilent).

Results

Figure 1B:
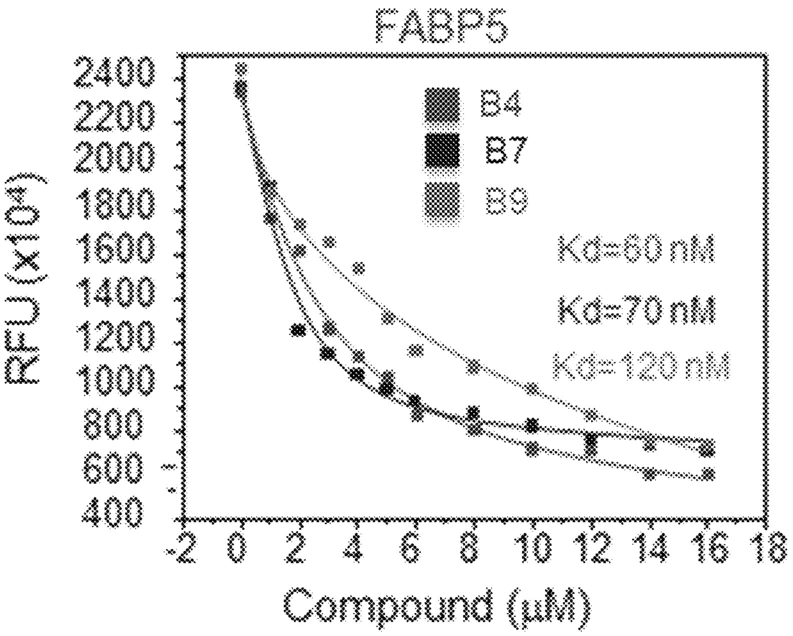
Figure 2:
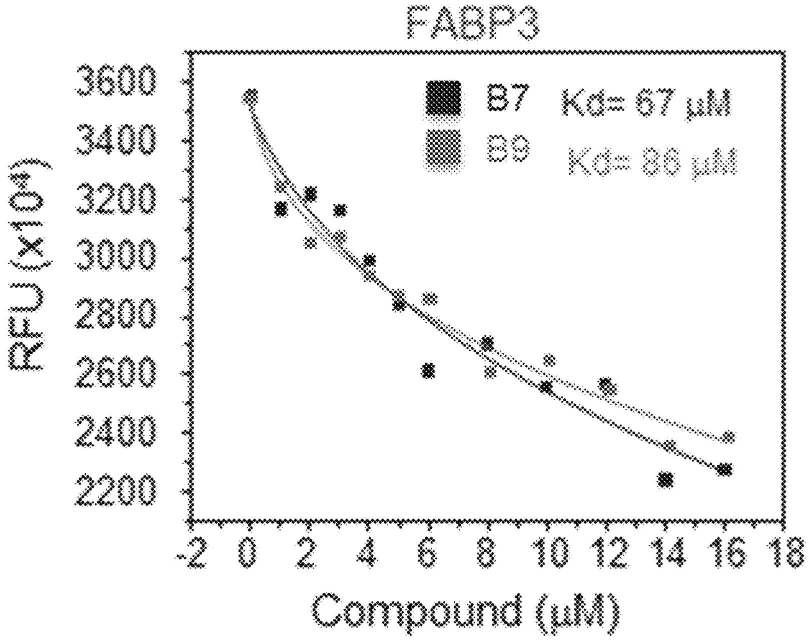
FIG. 2 depicts the binding affinity of the disclosed compounds B7 and B9 towards FABP3.
Figure 3:
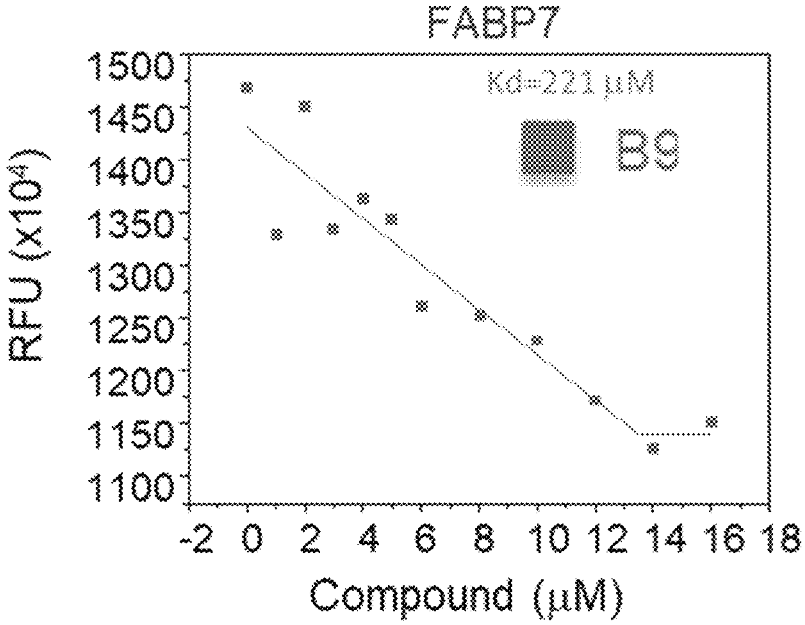
FIG. 3 depicts the binding affinity of the disclosed compound B9 towards FABP7.
Figure 4:
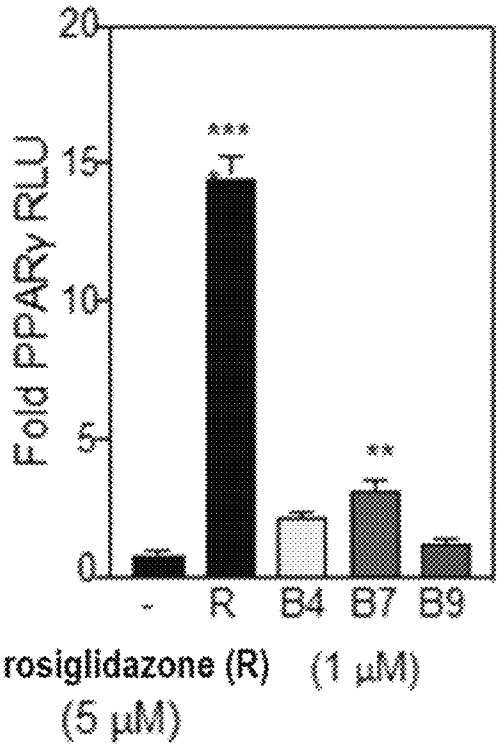
FIG. 4 shows that disclosed compounds B4, B7, and B9 did not activate transcription by PPARγ when tested against rosiglitazone a glycemic control compound.
Figure 5:
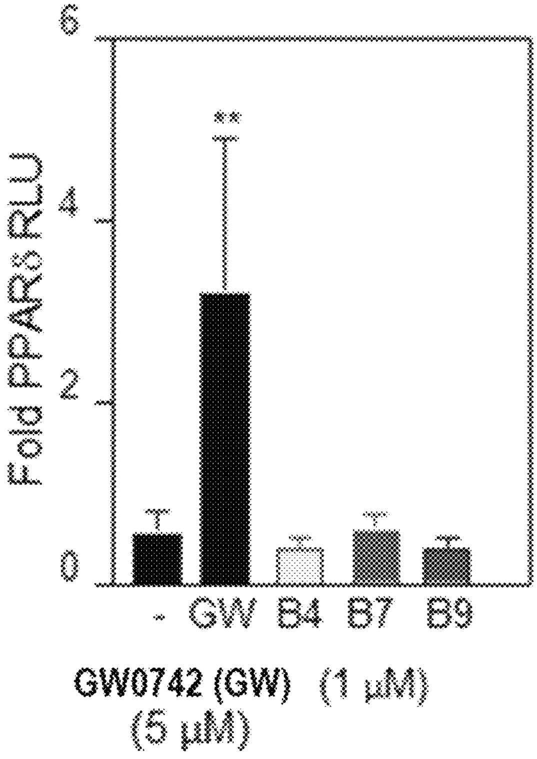
FIG. 5 shows that disclosed compounds B4, B7, and B9 did not active transcription by PPARδ as compared to GW0742, an activator of PPARδ.
Figure 6:
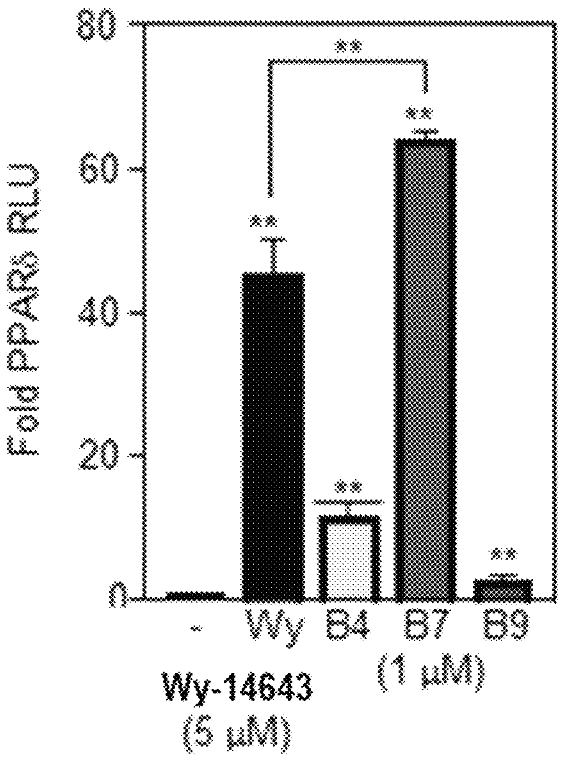
FIG. 6 depicts the fact that disclosed compound B7 was determined to activate PPARα as compared to WY-14643, a peroxisome proliferator and activator of PPARα.
Figure 7:
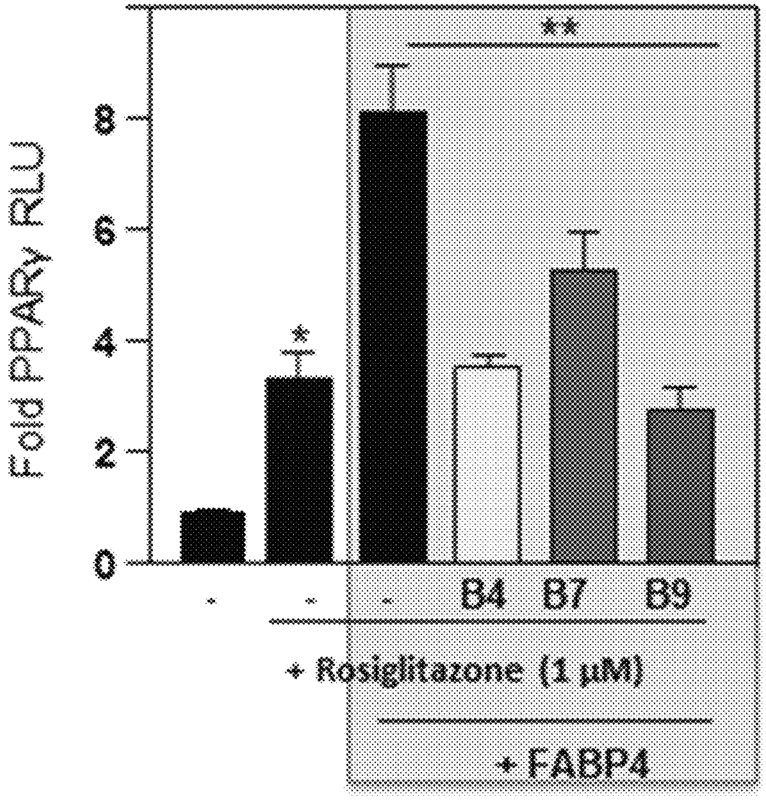
FIG. 7 shows the results of a transcriptional activation assay testing the disclosed compounds in cells that overexpress FABP4 when tested together with the PPARγ activator rosiglitazone.
Figure 8:
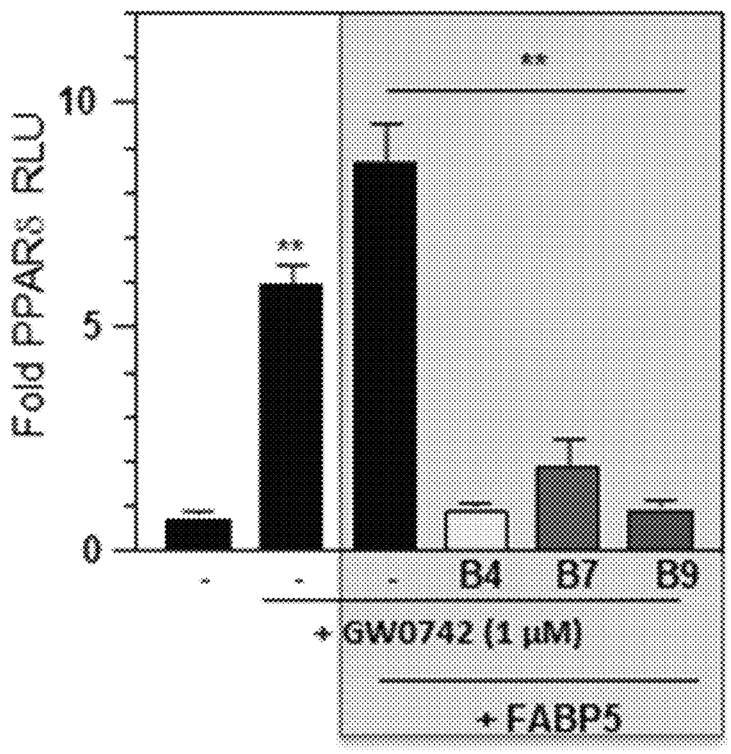
FIG. 8 shows the results of a transcriptional activation assay testing the disclosed compounds in cells that overexpress FABP5 when tested together with the PPARδ activator GW0742.
Figure 9:
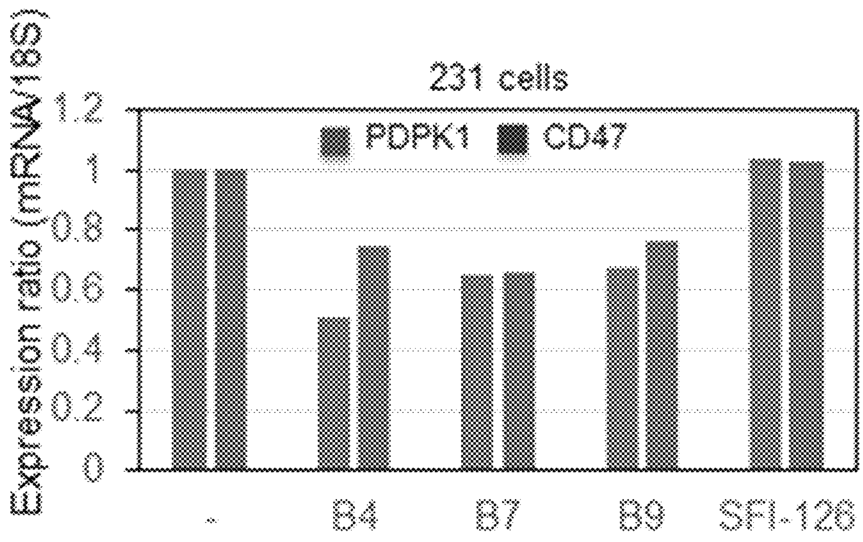
FIG. 9 depicts the effect of the disclosed compounds on the levels of PPARδ targets PDPK1 and CD47 in TNBC cells MB-231 after six hours.
Figure 10:
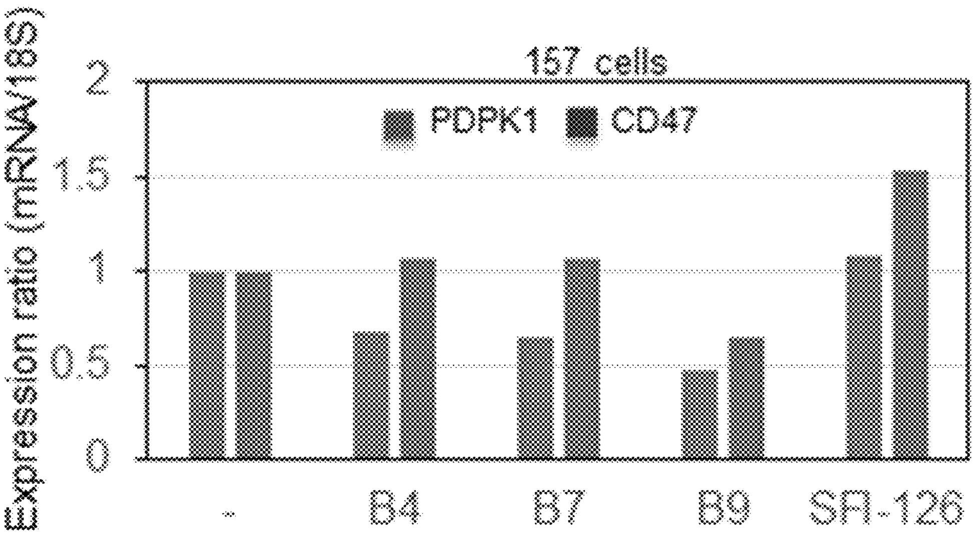
FIG. 10 depicts the effect of the disclosed compounds on the levels of PPARδ targets PDPK1 and CD47 in TNBC cells MB-157 after 6 hours.
Figure 11:
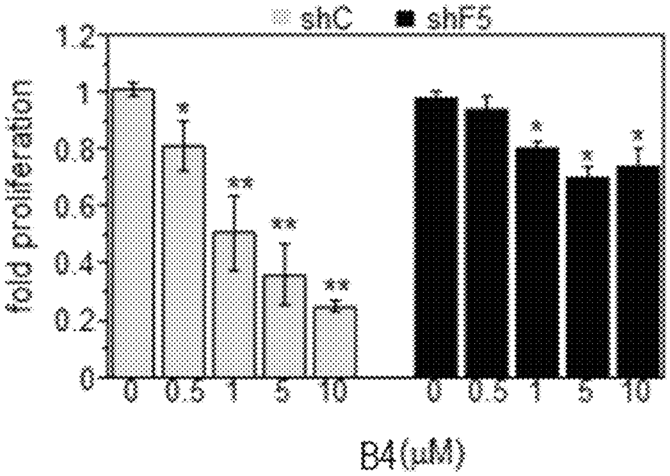
FIG. 11 shows plots of results indicating that compound B4 at different concentrations inhibits proliferation of MB-231 cell lines that stably express control shRNA ("shC") but not those cells stably expressing the FABP5 shRNA ("shF5").
Figure 12:
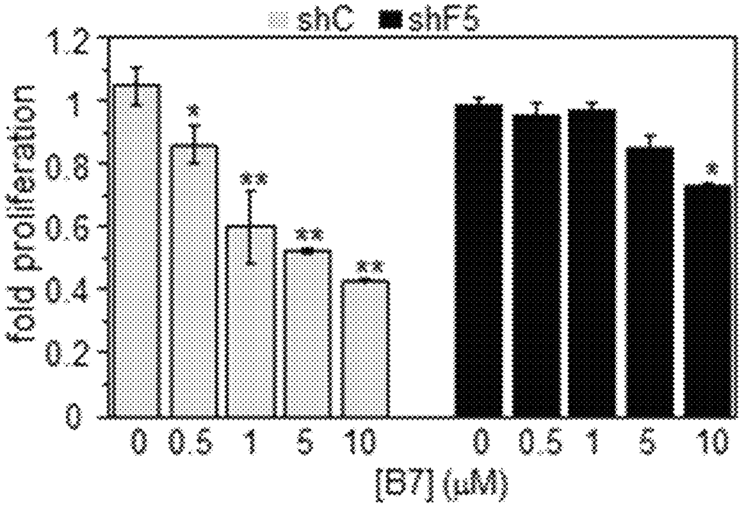
FIG. 12 shows plots of results indicating that compound B7 at different concentrations inhibits proliferation of MB-231 cell lines that stably express control shRNA ("shC") but not those cells stably expressing the FABP5 shRNA ("shF5").
Figure 13:
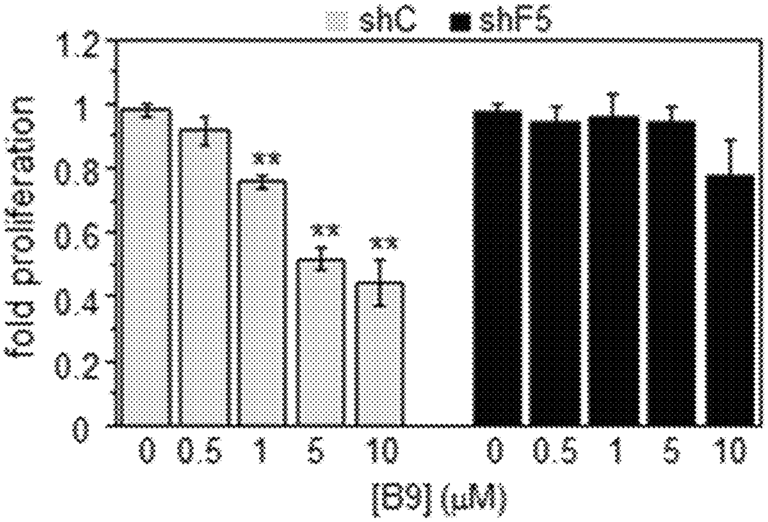
FIG. 13 shows plots of results indicating that compound B9 at different concentrations inhibits proliferation of MB-231 cell lines that stably express control shRNA ("shC") but not those cells stably expressing the FABP5 shRNA ("shF5").
Figure 14:
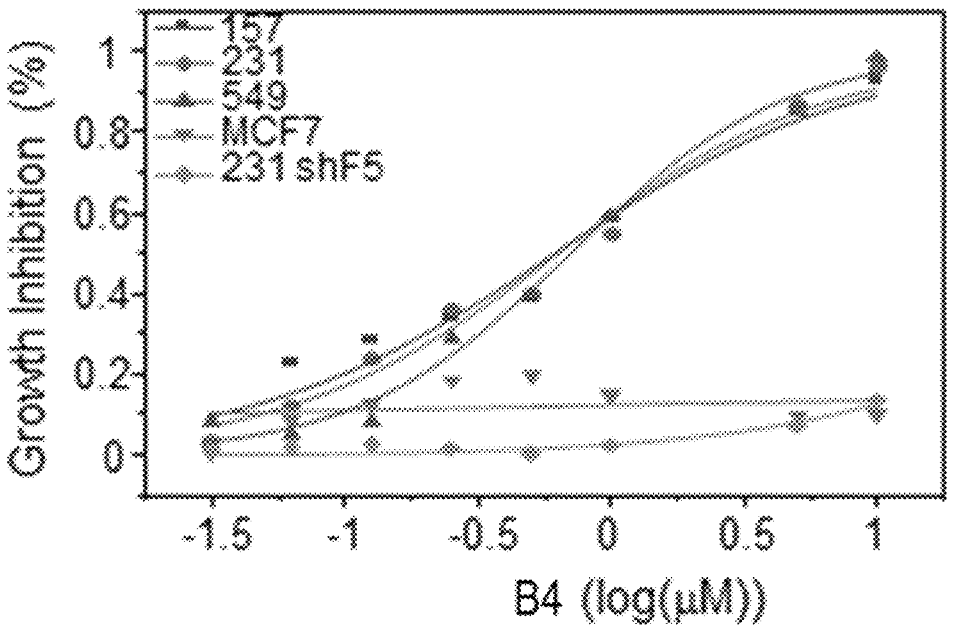
FIG. 14 shows plots of results indicating that compound B4 inhibited the growth of TNBC cell lines expressing high levels of FABP5 relative to the shRNA expressing MB231-shF5 control.
Figure 15:
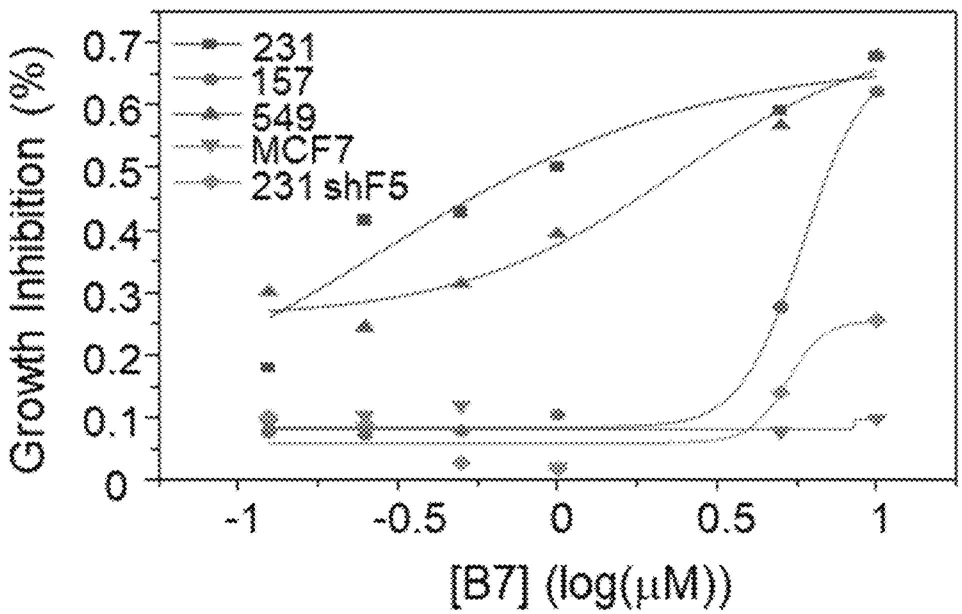
FIG. 15 shows plots of results indicating that compound B7 inhibited the growth of TNBC cell lines expressing high levels of FABP5 relative to the shRNA expressing MB231-shF5 control.
Figure 16:
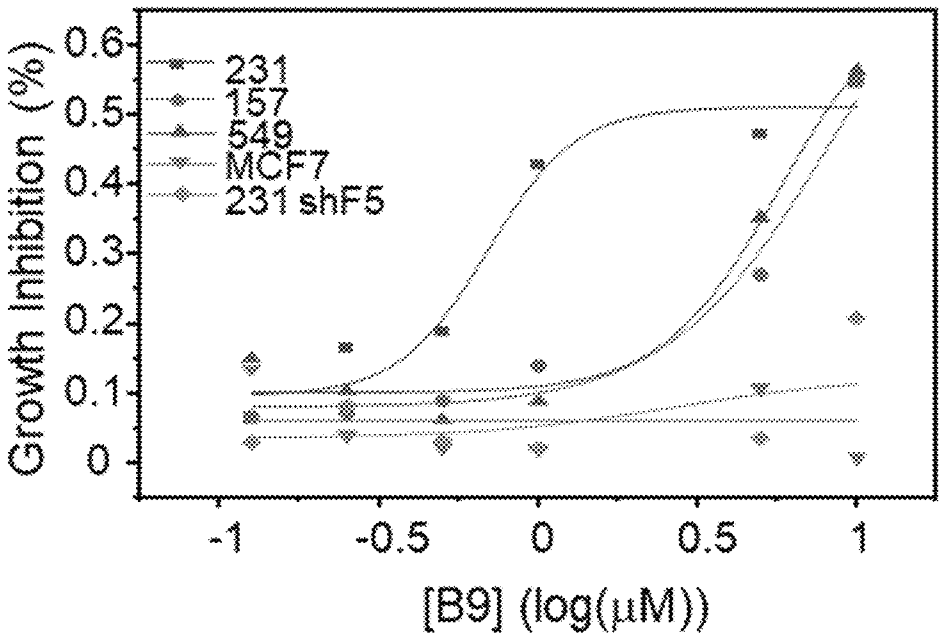
FIG. 16 shows plots of results indicating that compound B9 inhibited the growth of TNBC cell lines expressing high levels of FABP5 relative to the shRNA expressing MB231-shF5 control.

As shown in FIG. 1A and FIG. 1B, disclosed compounds B4, B7, and B9 showed high binding affinities towards FABP4 and FABP5 (Kd<1 μM) compared to affinity of binding FABP3 (FIG. 2) or FABP7 (FIG. 3). Each of these 3 compounds were found not to activate transcription by PPARγ (FIG. 4) or PPARδ (FIG. 5), however, B7 was found to activate PPARα (FIG. 6). Transcriptional activation assays in cells that overexpress either FABP4 together with PPARγ (FIG. 7) or FABP5 together with PPARδ (FIG. 8) show that B4, B7, and B9 inhibit activity of the nuclear receptors only in cells that express the binding proteins. This shows the specificity of B4, B7, and B9 to FABP4 and FABP5. As shown in FIG. 9 and FIG. 10, the levels of endogenous PPARδ targets PDPK1 and CD47 in TNBC cells MB-231 and MB-157 when treated with the B4, B7, and B9 at (1 μM) were significantly lower after only 6 hours.

As depicted in FIG. 11 through FIG. 16, compounds B4, B7, and B9 suppress the growth of TNBC cells and sensitize cells to standard chemotherapy. MB-231 lines stably expressing FABP5 shRNA ("shF5") or control shRNA ("shC") were treated with either B4 (FIG. 11), B7 (FIG. 12) or B9 (FIG. 13) in different concentrations and cell viability was assessed. Each of these compounds suppressed TNBC cell growth only in the cells highly expressing FABP5 (i.e., the cells not expressing shRNA). In addition, it was found that the efficacy of B4, B7, and B9 to inhibit cell growth was determined in multiple TNBC lines and in MCF7 using the stable line MB-231 shF5 as control for cell lines having low levels of FABP5. As shown by the plots of results depicted in FIG. 14, FIG. 15, and FIG. 16, compounds B4, B7, and B9 inhibited growth of only TNBC lines expressing high FABP5 levels. The $IC_{50}$ values calculated from this assay found that B4 was the most efficient inhibitor. As such, compound B4 was further evaluated for its effect on TNBC cells and in other disease models.

Figure 17:
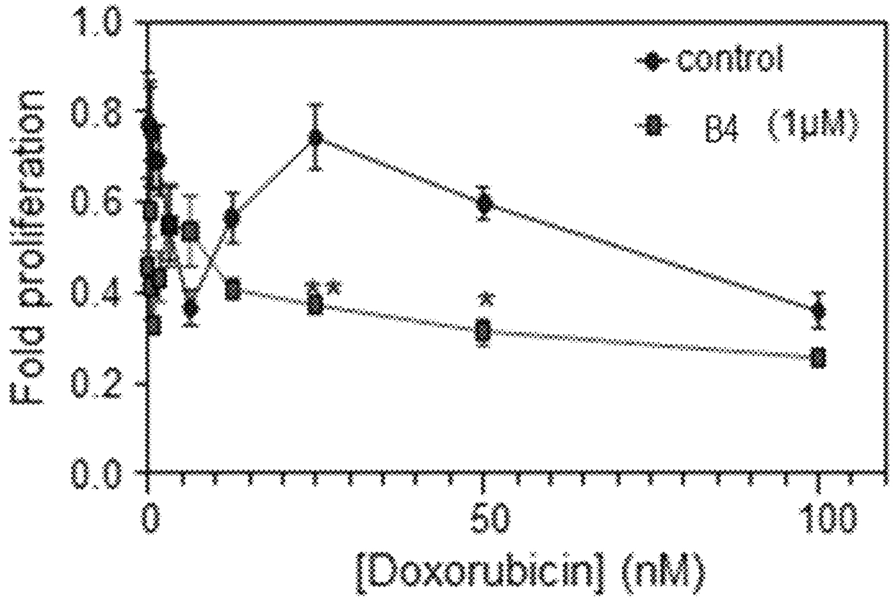
FIG. 17 shows the results of a cell proliferation assay when BT-549 cells were treated with the disclosed compound B4 at 1 μM in combination with doxorubicin over a concentration range of from 0 to 100 nM of doxorubicin.
Figure 18:
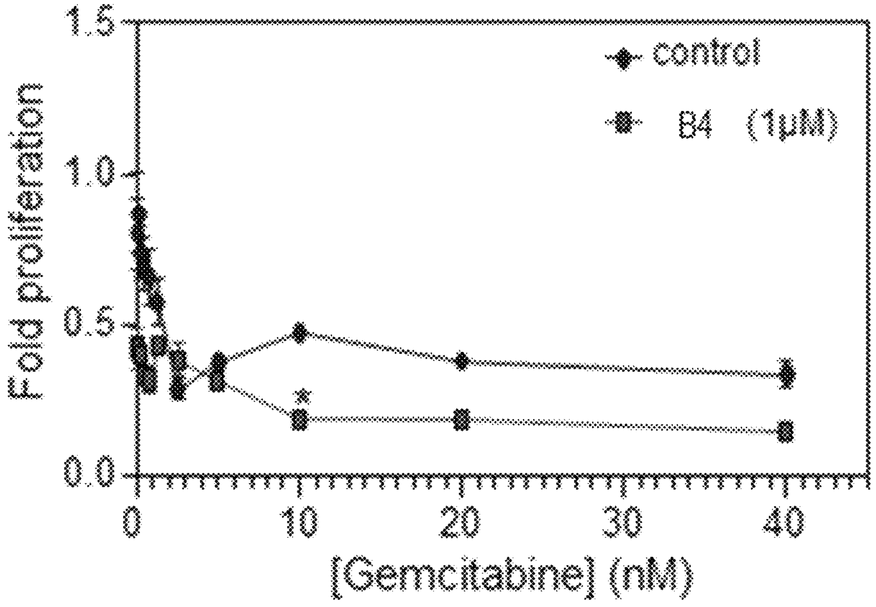
FIG. 18 shows the results of a cell proliferation assay when BT-549 cells were treated with the disclosed compound B4 at 1 μM in combination with gemcitabine over a concentration range of from 0 to 40 nM of gemcitabine.
Figure 19:
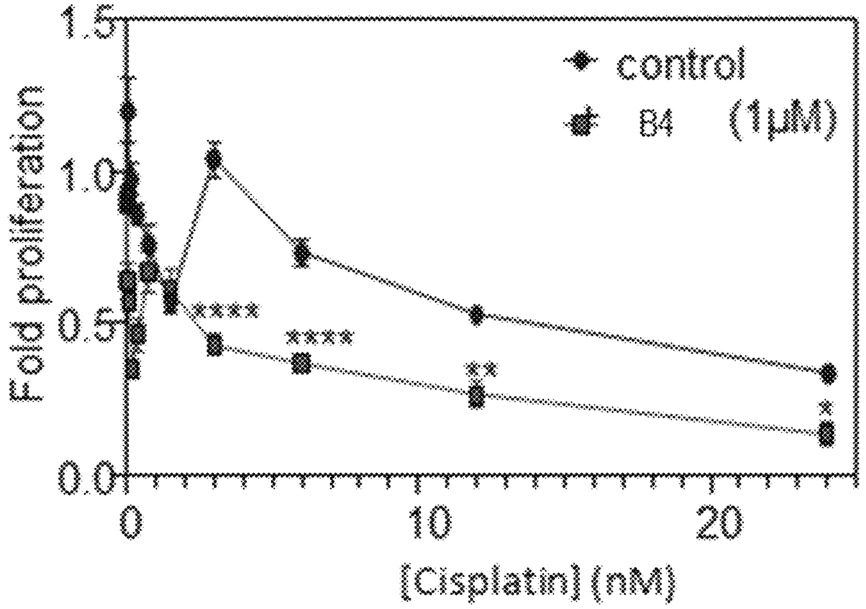
FIG. 19 shows the results of a cell proliferation assay when BT-549 cells were treated with the disclosed compound B4 at 1 μM in combination with cisplatin over a concentration range of from 0 to 24 nM of cisplatin.
Figure 20:
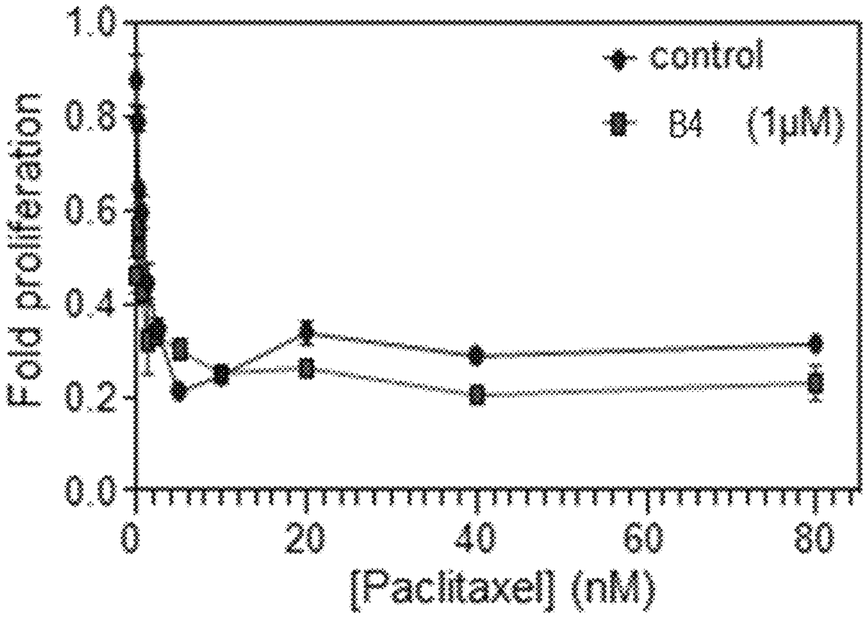
FIG. 20 shows the results of a cell proliferation assay when BT-549 cells were treated with the disclosed compound B4 at 1 μM in combination with paclitaxel over a concentration range of from 0 to 80 nM of paclitaxel.
Figure 21:
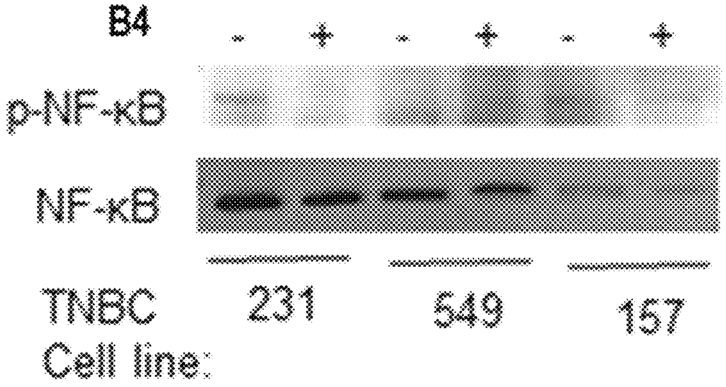
FIG. 21 discloses a Western blot of the levels of phosphorylated NF-kB and NF-kB in the TNBC lines 231, 549 and 157 after treatment with disclosed compound B4.
Figure 22:
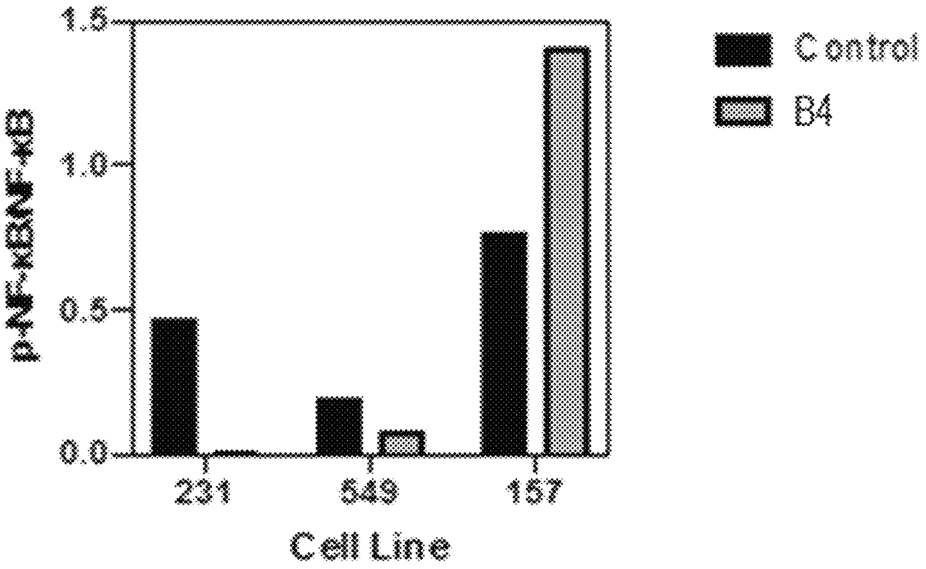
FIG. 22 is a quantitative extrapolation of the values visualized in FIG. 21 indicating that the disclosed compound B4 reduced the levels of activated NF-kB in cell lines thereby indicating the resulting anti-inflammatory and anti-carcinogenic effect for FABP5 inhibition.

Without wishing to be limited by theory, one mechanism by which cancer cells acquire resistance to therapy is known to be the cancer stem cells within tumors that can proliferate rapidly, metastasize, and generate new tumors. Therefore, compounds which effectively inhibit FABP5 target the cancer stem-cells and sensitize TNBC cells to standard chemotherapy. As shown in FIG. 17, when BT-549 cells were treated with doxorubicin in combination with compound B4, these cells were sensitized to chemotherapy. The same is true for the combination of compound B4 and gemcitabine (FIG. 18), cisplatin (FIG. 19), and paclitaxel (FIG. 20). Following treatment with compound B4, the levels of phosphorylated NF-kB was evaluated. As shown in FIG. 21 and FIG. 22, B4 significantly reduced the level of activated NF-kB in the cells, indicating an anti-inflammatory and anti-carcinogenic effect due to FABP5 inhibition.

Figure 23A:
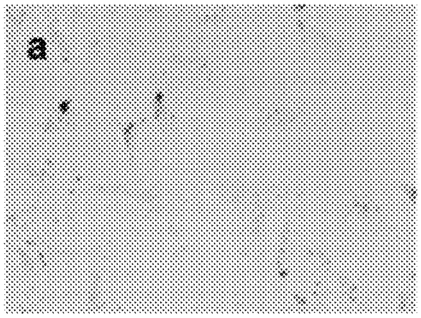
FIG. 23A, FIG. 23B, FIG. 23C, and FIG. 23D depict the reversion of activated LX-2 cells and the enlargement of their lipid droplets (LD). The control media are depicted in FIG. 23A and FIG. 23B while the media depicted in FIG. 23C and FIG. 23D contained a 2% lipid admixture with palmitate and oleic acid.
Figure 23B:
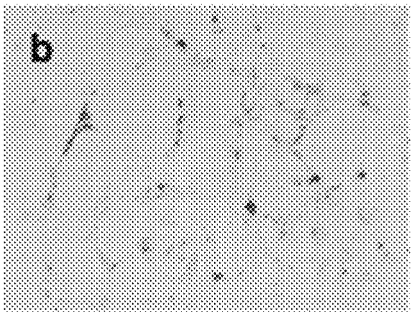
Figure 23C:
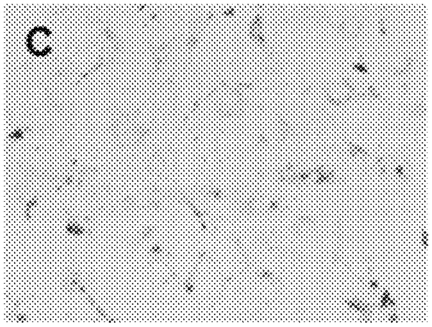
Figure 23D:
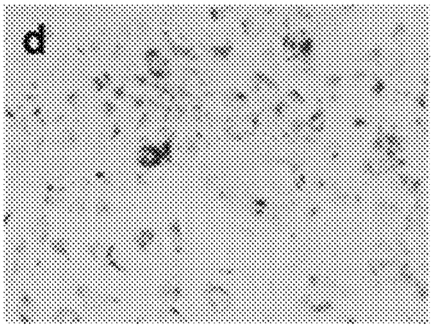
Figure 24:
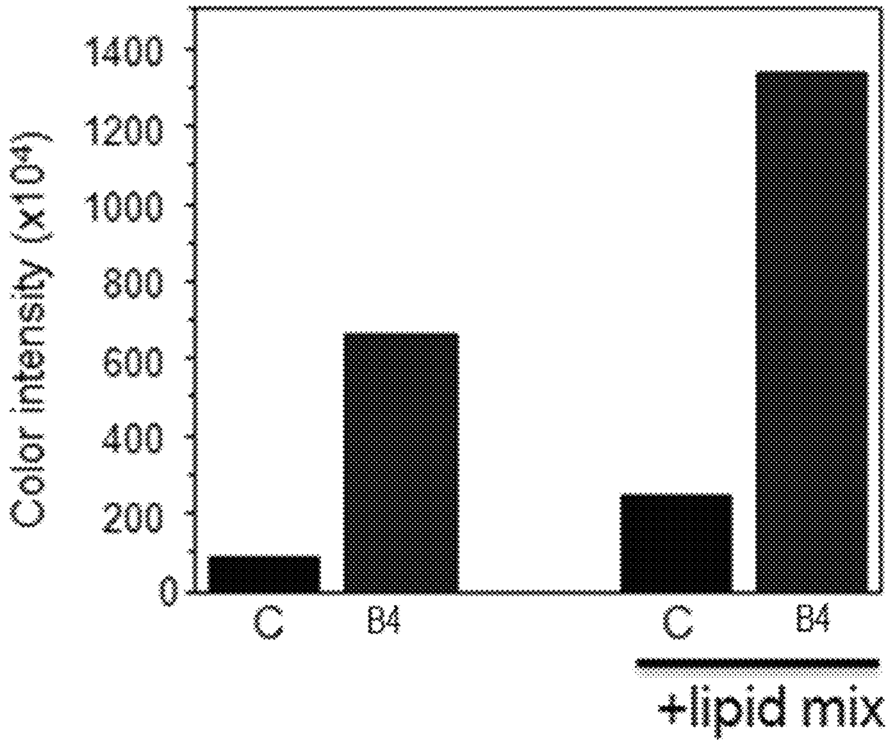
FIG. 24 shows the relative intensity of Oil Red O stained lipid droplets as measured for FIG. 23A-FIG. 23D.
Figures 25A, 25B, 25C:
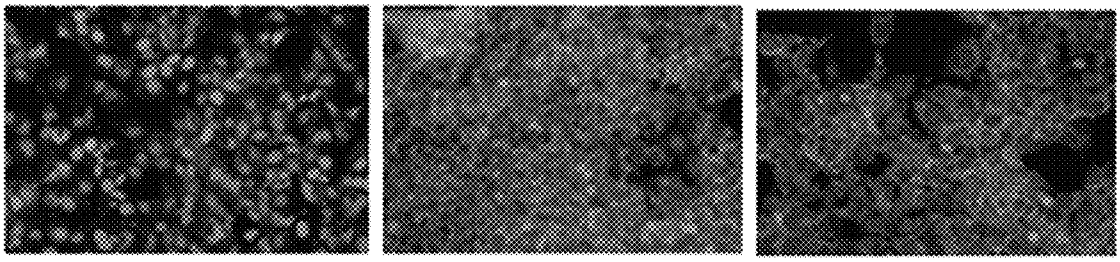
FIG. 25A, FIG. 25B, FIG. 25C, FIG. 25D, FIG. 25E, and FIG. 25F are photographs showing the effects on LX-2 Human Hepatic Stellate Cell activation by tracing the levels of α-SMA following activation by TGF-β and upon treatment with disclosed compound B4.
Figures 25D, 25E, 25F:
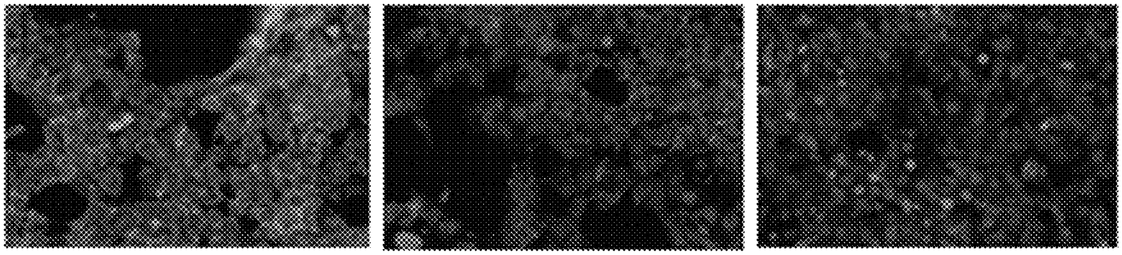
Figure 26:
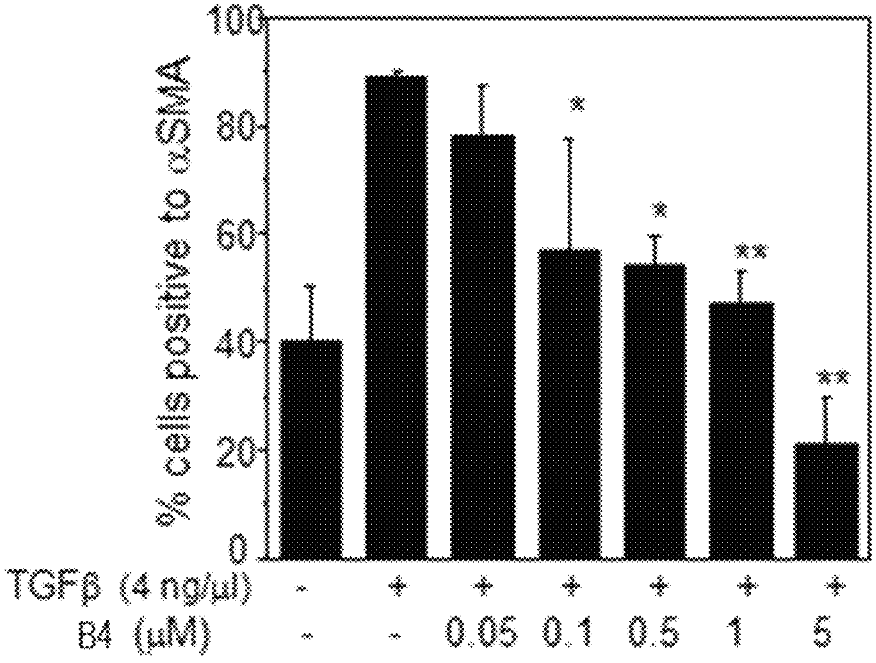
FIG. 26 is a histogram depicting the levels of α-SMA (relative to number of live cells) following activation determined from the data from FIG. 25A-FIG. 25F.
Figures 27A, 27B, 27C:
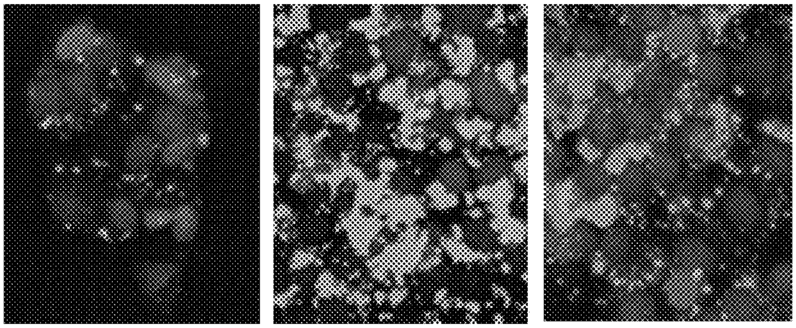
FIG. 27A, FIG. 27B, FIG. 27C, FIG. 27D, FIG. 27E, and FIG. 27F show the lipid accumulation by HepG2 Human Hepatic Cells as quantified by Nile Red. The cells, except for the control were pre-treated with oleic acid (1.0 mM).
Figures 27D, 27E, 27F:
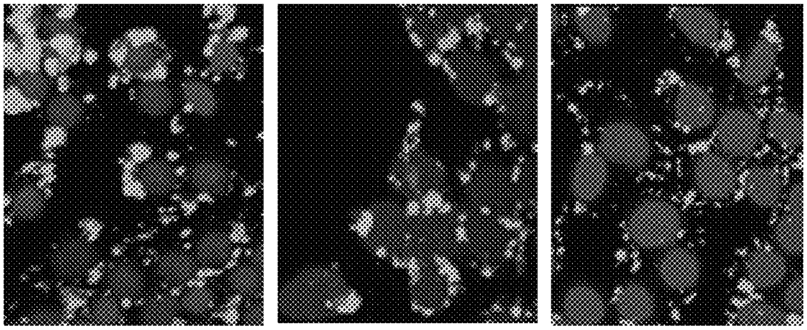
Figure 28:
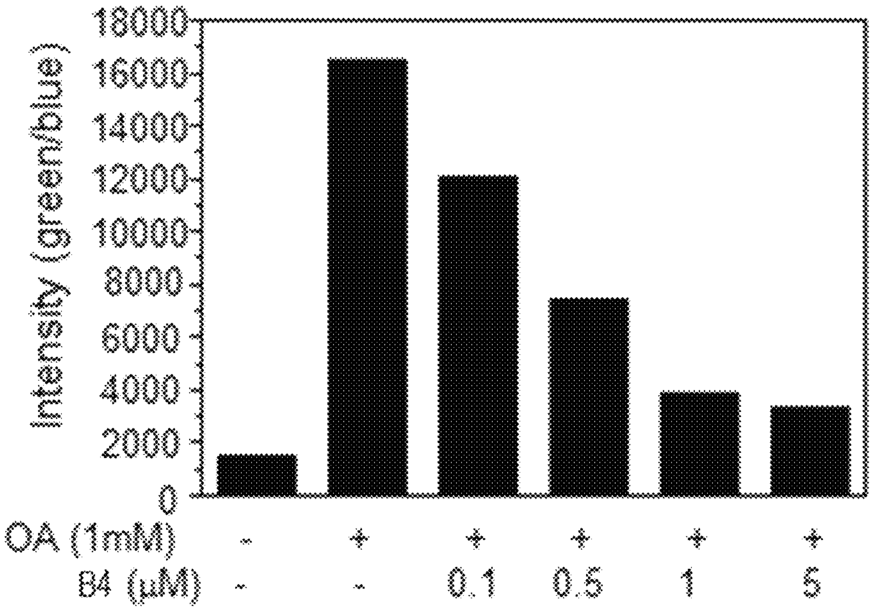
FIG. 28 is a histogram depicting the quantified amounts of uptake (Nile Red) for the samples shown in FIG. 27A-FIG. 27F.

Without wishing to be limited by theory, compound B4 reverses activation of hepatic stellate cells and prevents uptake of lipids into hepatocytes in in vitro models for liver steatosis and fibrosis. The effects of compound B4 on the reversion of activated LX-2 cells and the enlargement of their lipid droplets (LD) is shown in FIG. 23A to FIG. 23D. Activated LX-2 cells were treated with 2% lipid mix containing palmitate and oleic acid known to reverse activation of the cells. Treatment with either the lipid mixes or compound B4 increased the amount of LD in the cells as indicated by Oil Red O staining (FIG. 23B and FIG. 23C) and co-treatment with lipid mix and compound B4 increases the LD size even more (FIG. 23D and FIG. 24). The effect on LX-2 activation was also assessed by tracing levels of the fibrosis marker α-SMA following activation by TGF-β. Levels of α-SMA in cells treated with compound B4 was significantly lower than in untreated cells (FIG. 25A to FIG. 25F and FIG. 26). HepG2 cells were used to test effect of compound B4 on liver steatosis. Cells were treated with OA (1 mM) in the presence or absence of compound B4 and lipid accumulation in the cells was quantified using Nile Red. FIG. 27A to FIG. 27D and FIG. 28 show that treatment with compound B4 prevented uptake of lipids into hepatocytes. As seen in FIG. 29, the size of the lipid droplets in the cells was also affected by exhibiting significantly smaller droplets in the treated cells.

Figure 31:
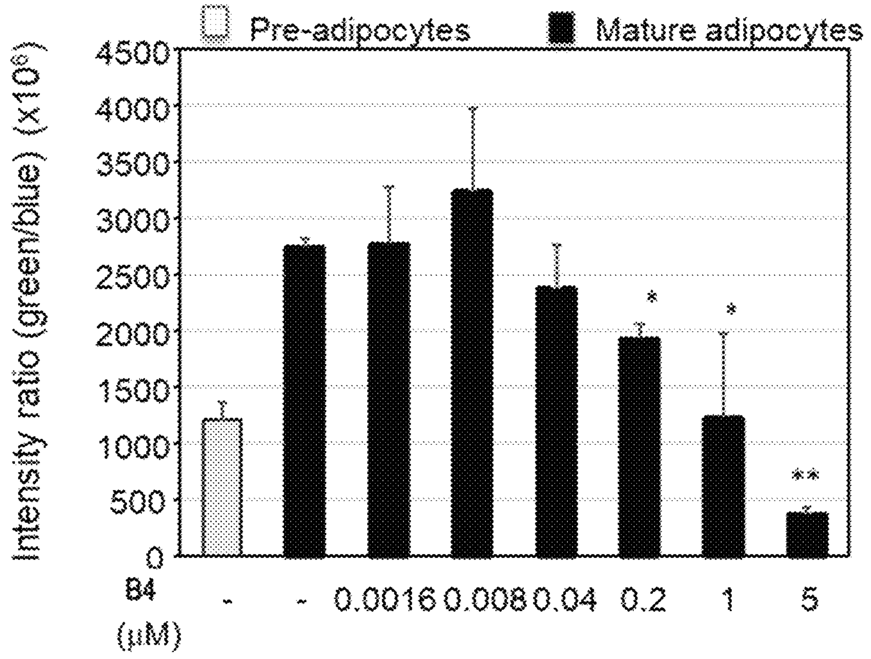
FIG. 31 is a histogram depicting the results of treatment with B4 in mouse 3T3-L1 differentiated cells. The differentiated cells were treated on day six and stained with Nile Red on day 12.
Figure 32:
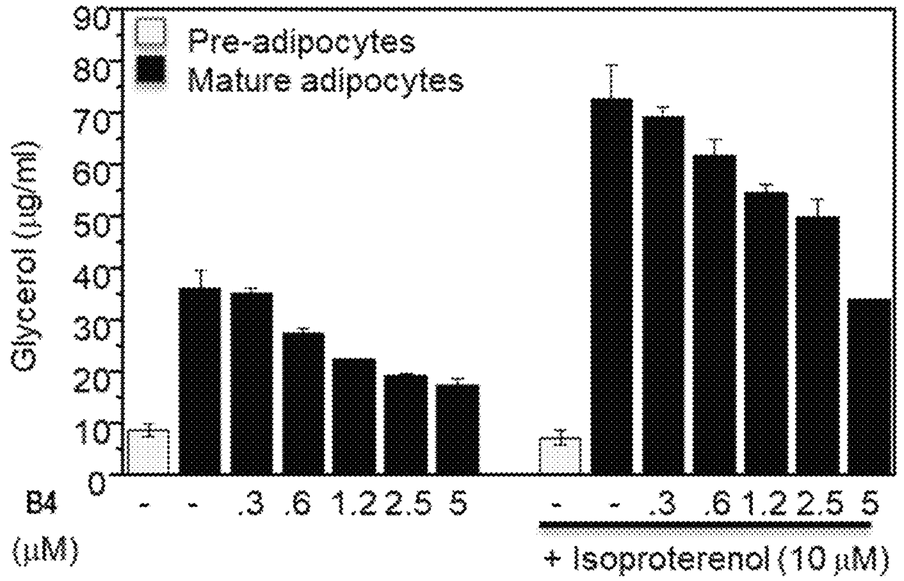
FIG. 32 shows the inhibition of glycerol release when mature adipocytes are treated with the disclosed compound B4. As depicted in FIG. 32 the effect was more potent in isoproterenol-stimulated lipolysis.

As evidenced in FIG. 30A to FIG. 30F, FIG. 31 and FIG. 32, compound B4 inhibits lipid uptake, and basal and isoproterenol-stimulated lipolysis in 3T3-L1 adipocytes. Mouse 3T3-L1 cells were differentiated in culture to become mature adipocytes. Compound B4 in varying concentrations was added starting at day 6 of the differentiation. On day 12, the lipid droplets were stained by Nile Red and quantified (FIG. 30A to FIG. 30F). Compound B4 treated adipocytes had fewer LD within the cells (FIG. 31). Next, the effect of compound B4 was tested on lipolysis in the mature adipocytes. Compound B4 inhibited basal lipolysis (represented by reduced glycerol release into the culture medium as seen in FIG. 32) and the effect was more potent in isoproterenol-stimulated lipolysis.

Figure 33:
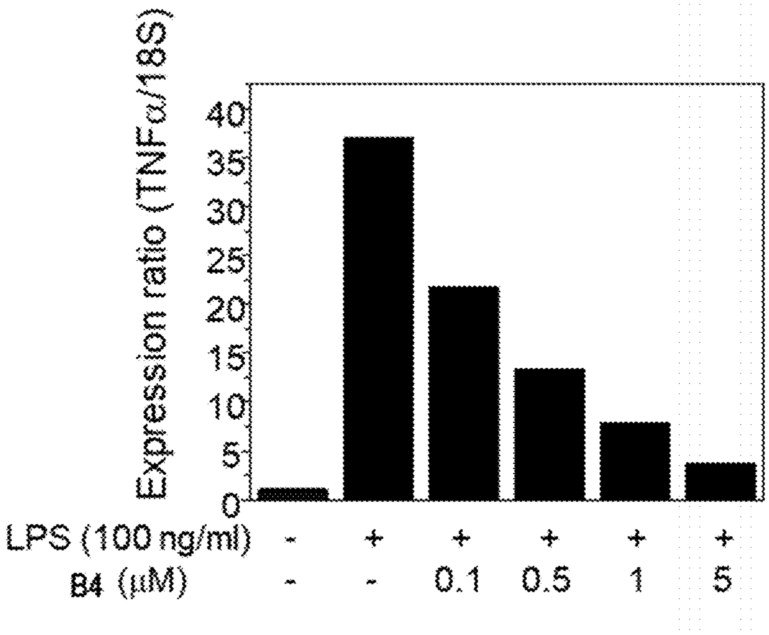
FIG. 33 shows the decrease in expression of TNFα when RAW 264.7 murine macrophage cells are treated with the disclosed compound B4 over the concentration range of 0 to 5 μM then stimulated with LPS at concentration of 100 ng/ml.
Figure 34:
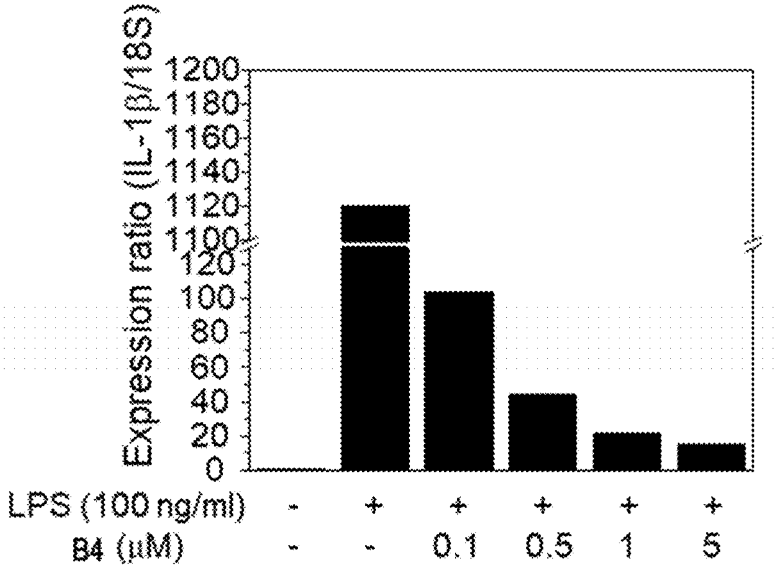
FIG. 34 shows the decrease in expression of IL-1μ when RAW 264.7 murine macrophage cells are treated with the disclosed compound B4 over the concentration range of 0 to 5 μM then stimulated with LPS at concentration of 100 ng/ml.
Figure 35:
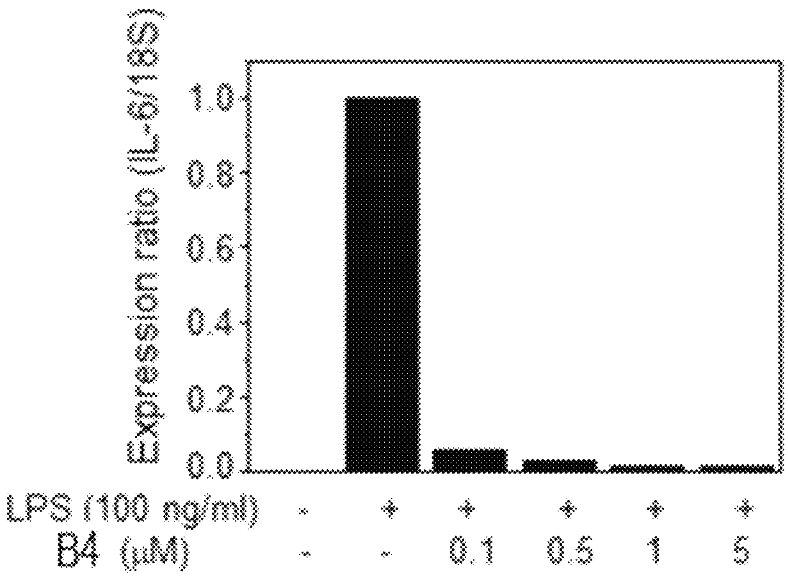
FIG. 35 shows the decrease in expression of IL-6 when RAW 264.7 murine macrophage cells are treated with the disclosed compound B4 over the concentration range of 0 to 5 μM then stimulated with LPS at concentration of 100 ng/ml.

FIG. 33, FIG. 34, and FIG. 35 show the anti-inflammatory effects of compound B4 on RAW264.7 murine macrophage cells. Cells were pre-treated with compound B4 then stimulated by lipopolysaccharide (LPS) and expression levels of proinflammatory cytokines TNFα, IL-1β and IL-6 were measured by QPCR. mRNA levels for all 3 cytokines were lower in the treated cells indicating that dual inhibition of FABP4 and FABP5 can provide a beneficial anti-inflammatory effect.

Example 18: Biological Studies of FABP4/5 Inhibitor Compounds B4, B104, B108, B110, B116, and B118

This example illustrates studies of biological function and effect of the FABP4/5 inhibitor compounds B4, B104, B108, B110, B116, and B118.

Materials and Methods

A. Cells Used

COS-7, MDA-MB-231, HepG2, LX-2, 3T3-L1, NPG, and MCF7 were cultured in Dulbecco's modified Eagle's medium (DMEM) supplemented with 10% fetal bovine serum (Invitrogen Life Sciences, Carlsbad, CA). MDA-MB-157 and MB-549 cells were cultured in L-Glutamine containing RPMI medium supplemented with 10% fetal calf serum (Invitrogen Life Sciences, Carlsbad, CA). For proliferation assays, 2000 cells were plated in each well of 96-well plate. The next day cells were treated with compounds and incubated in Incucyte for 4 days. Images taken every 4 hours for the duration of the time were analyzed to calculate percentage of confluency in response to the treatments.

B. Transactivation Assays

COS-7 were cultured in 6-well plates and co-transfected with either a luciferase reporter driven by 3 copies of a PPRE and expression vector for either PPARδ, PPARα or PPARγ together with a vector harboring cDNA for β-galactosidase, serving as a transfection control. 18 h. post-transfection, cells were placed in a serum-free medium and treated with agonist/compound. 18 h. later, cells were lysed, luciferase activity was assayed (Promega, WI, USA) and corrected for transfection efficiency by the activity of β-galactosidase.

C. Xenograft Experiments

Eight-week-old NSG nude females were injected subcutaneously into the right flank with $5\times10^6$ MB-231 cells 1:1 with matrigel. Treatments started the day after cells injections 5 days a week. Mice were treated with either vehicle (5% DMSO, 15%-HPCBD (PH 9.0) in water), 20 mg/kg, or 40 mg/kg B4 dissolved in vehicle. Tumor size was assessed twice per week using a digital caliper. Tumor volumes were determined by measuring the length (l) and the width (w) of the tumor and calculating the volume ($V=lw^2/2$). Mice were scarified 14 days after injection. Statistical significance between the control and treated mice in both experiments was evaluated using a Student's t test. Mouse experiments were conducted after approval by the institutional animal care and use committee at Case Western Reserve University.

D. Lipid Uptake Assays 1) 3T3-L1: Mouse 3T3-L1 cells were differentiated in culture according to ATCC protocol to become mature adipocytes. At day 6 of the differentiation, compound treatment started. Cells were stained by Nile Red on day and color intensity in each cell was measured relative to Dapi staining. Lipolysis was measured by measuring glycerol levels using lipolysis kit (Cayman, USA) according to the manufacturer manual.

2) Hepg2 cells: 5000 cells were plated in 96-well plate. The next day cells were treated with tested compounds for 4 hours and then treated with 1 mM oleic acid for additional 24 hours. Cells were then stained with Nile Red and Dapi and lipid content was quantified.

Results

A. Compounds B104, B108, B110, B116, and B118 do not Activate Transcription by PPARδ

Figure 36A:
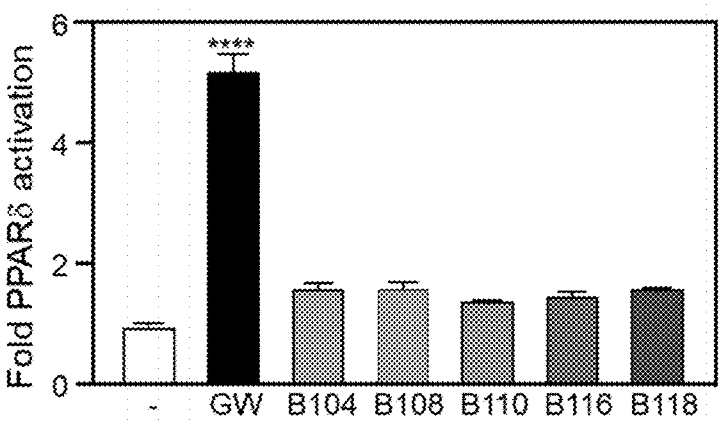
FIG. 36A, FIG. 36B, and FIG. 36C show compounds B104, B108, B110, B116, and B118 do not activate transcription by PPARδ. Transcriptional activation assays in COS7 cells co-transfected with vectors encoding either PPARδ (FIG. 36A), PPARα (FIG. 36B), or PPARγ (FIG. 36C), together with a PPAR response element (PPRE), and a vector harboring β-galactosidase, serving as a transfection control. Cells were treated with PPARs' specific agonists GW0742 (GW) (1 M), WY-14643 (Wy) (5 μM) rosiglitazone (R) (1 μM), or one of the compounds B104, B108, B110, B116, or B118 (5 μM).
Figure 36B:
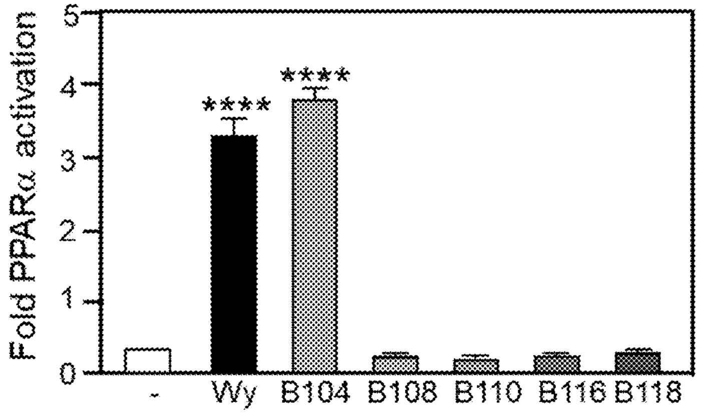
Figure 36C:
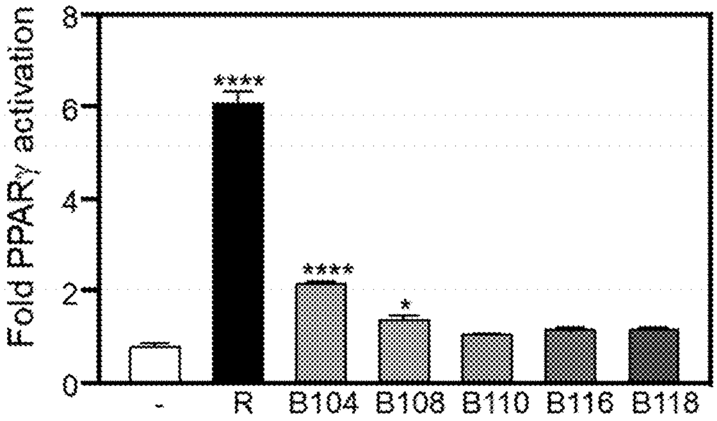

To eliminate the possibility that the aniline compounds B104, B106, B110, B116, and B118 are ligands of the nuclear receptor PPARδ and will activate transcription of this pro-carcinogenic transcription factor, transcriptional activation assays were conducted utilizing COS7 cells. Unlike PPARδ specific agonist, GW0742 (1 mM) that induce activation of PPARδ by 5.5-fold, none of the tested aniline compounds affected activation of the receptor (FIG. 36A). Next, the effect of these compounds was tested on activation of other members of the PPAR family, PPARα and PPARγ using their specific agonists Wy-14643 (5 mM) and rosiglitazone (1 mM), respectively. Other then B104 that was found to activate both PPARα and PPARγ (FIG. 36B and FIG. 36C) and B108 that activated PPARγ (FIG. 36C), the other tested compounds did not affect transcription activity of the PPARs.

B. Compounds B104, B108, B110, B116, and B118 Suppress Growth of TNBC Cells More Effectively than the Commercially Available Inhibitor SBF-I26

Figure 37A:
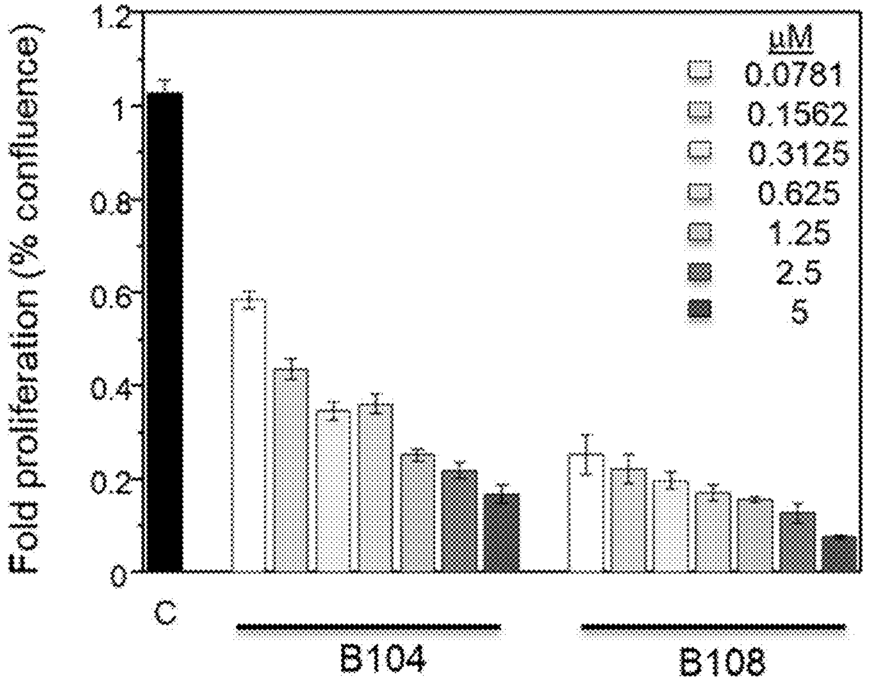
FIG. 37A, FIG. 37B, FIG. 37C, FIG. 37D, FIG. 37E, and FIG. 37F depict plots of results showing that the FABP4/5 inhibitor compounds B104, B108, B116, and B118 inhibit growth of TNBC cells more efficiently than FABP5/7 inhibitor SBF-126. A), B), C), D) MB-231 cells were treated with one of the denoted compounds at indicated concentrations for 4 days. Cells confluency was measured using Incucyte software. b), d) $EC_{50}$ values were calculated using GraphPad fitting algorithms. E), F) TNBC lines MB-157 (E), and BT-549 (F) were treated with the compounds for 4 days at designated concentrations. Cells confluency was measured using Incucyte software.
Figure 37B:
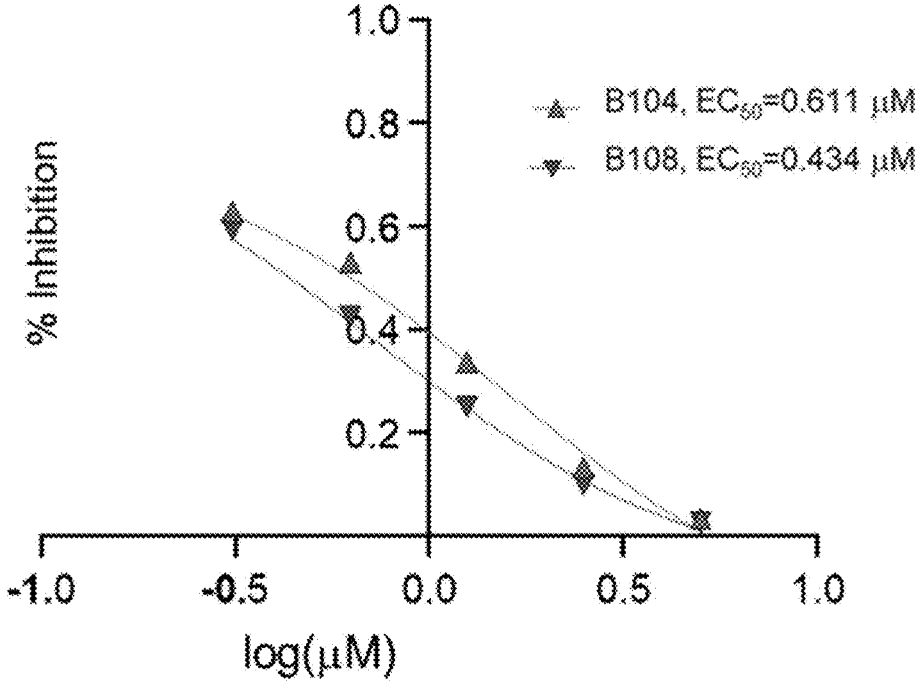
Figure 37C:
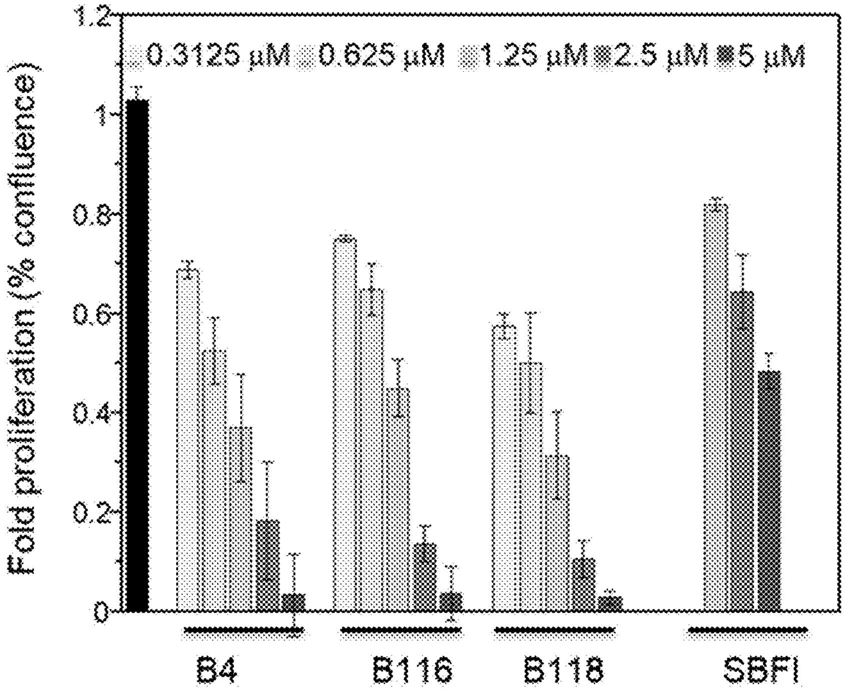
Figure 37D:
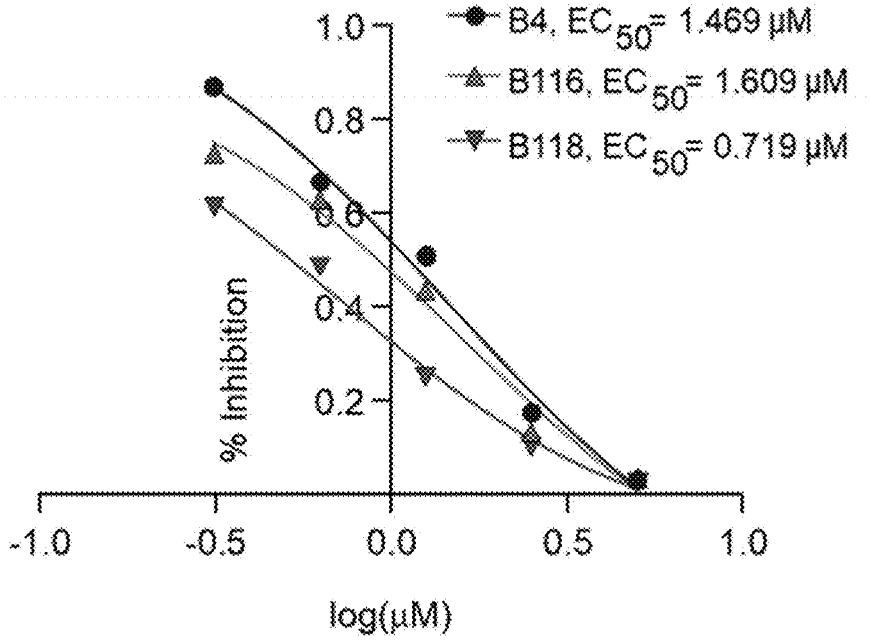
Figure 37E:
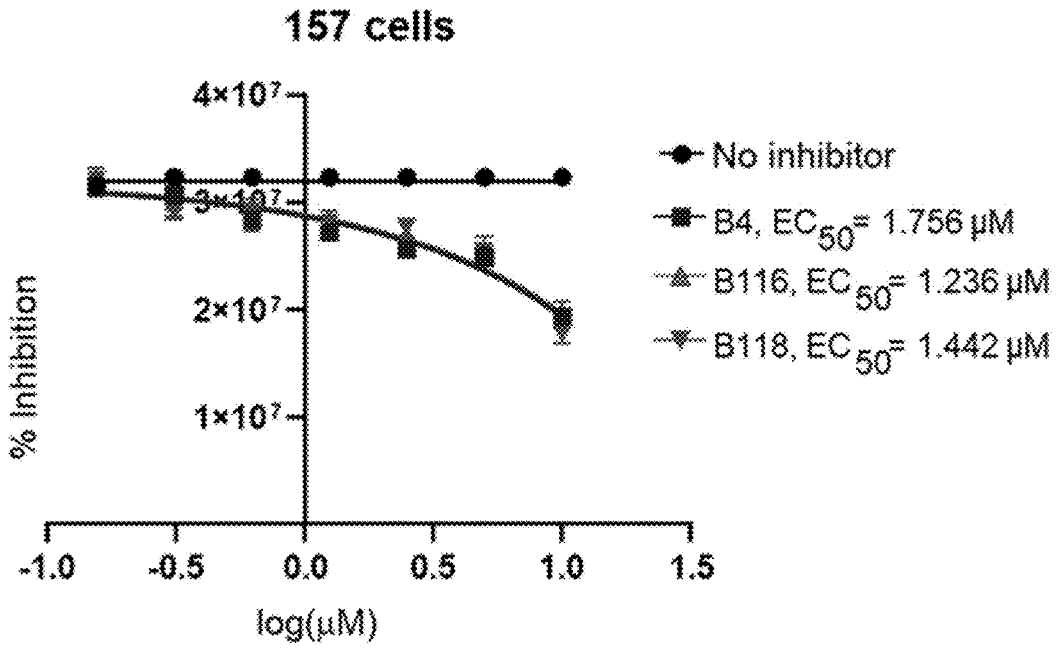
Figure 37F:
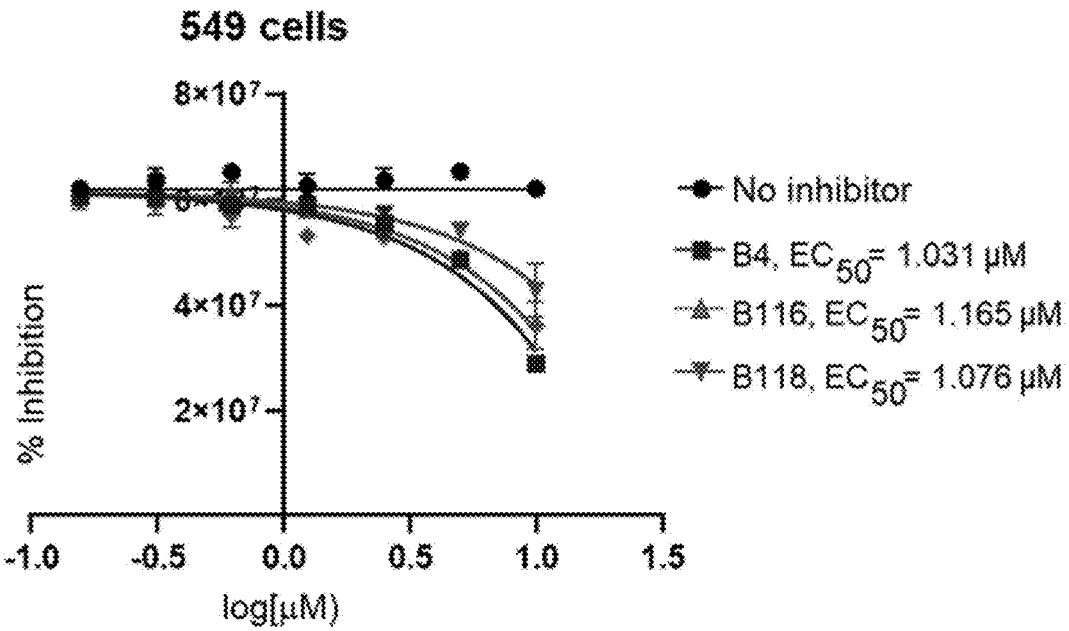

The TNBC line MB-231 was used to calculate the efficacy of compounds B104, B106, B110, B116, and B118 in inhibiting proliferation of the cancer cells. Cells were treated with serial dilution of the compounds or the known FABP5/7 inhibitor SBF-I26 and proliferation was measured in Incucyte by calculating percentage of confluency every 4 hours over 4 days. The data clearly show that treatment of 231 cells with the aniline compounds suppress proliferation of the TNBC cells 5-fold more effectively than the SBF-I26 (FIG. 37A and FIG. 37C). The $EC_{50}$ for each compound was calculated by fitting the percentage of inhibition vs. the logarithmic transformation of the used concentrations (FIG. 37B and FIG. 37D). Additionally, the effect of B116 and B118 was also tested on proliferation of the human TNBC lines MDA-MB-157 (FIG. 37E) and MB-549 (FIG. 37F). Similarly, to the effect observed in the 231 cells, B116 and B118 inhibited proliferation of both TNBC lines (FIG. 37E and FIG. 37F).

C. Compound B4 Suppresses Growth of TNBC Tumors In Vivo

Figure 38A:
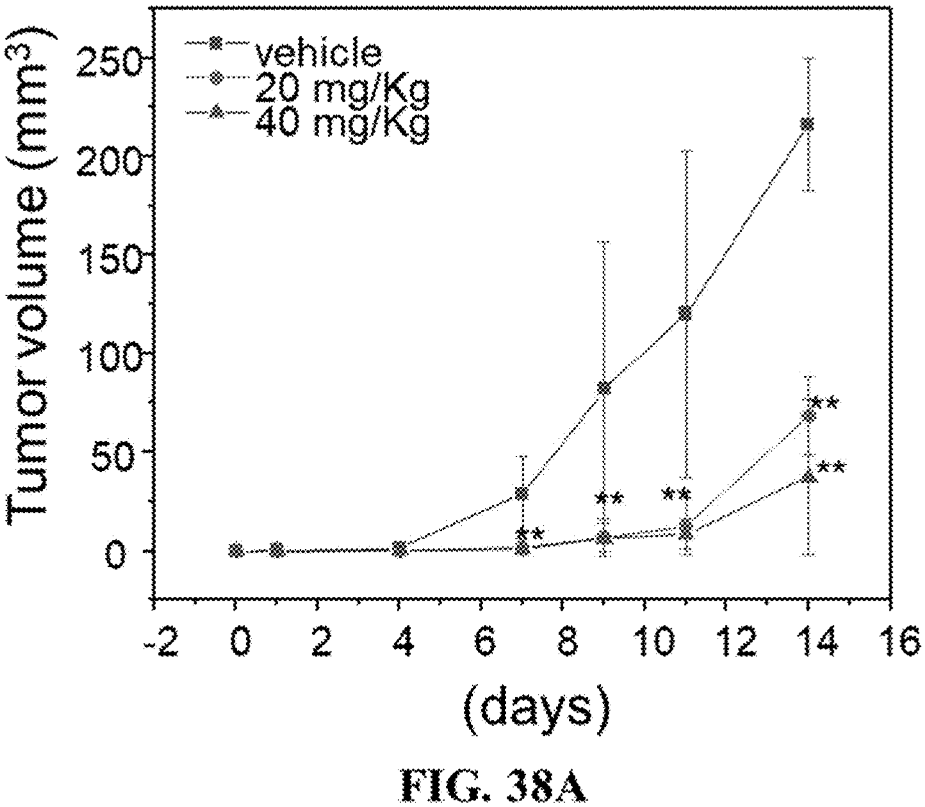
FIG. 38A and FIG. 38B depict results showing FABP5 inhibitor B4 suppress tumor growth in vivo.
Figure 38B:
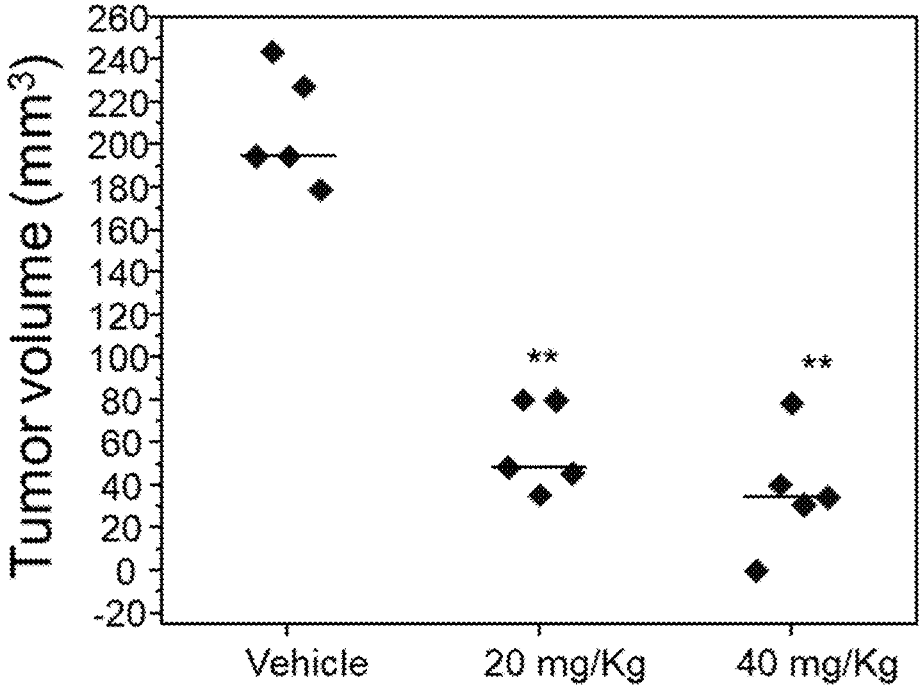

TNBC xenograft model was used to test the efficacy of B4 in suppressing growth on tumors in vivo. $5\times10^6$ MB-231 cells were subcutaneously injected into the right flank of NSG mice. B4 (20, or 40 mg/kg) or a vehicle were IP injected 5 times a week and tumor growth was monitored. Strikingly, B4 almost completely abolished growth of 231 tumors after 14 days (FIG. 38A and FIG. 38B). The 2 doses of B4 tested resulted in similar inhibition indicating even the lower dose is sufficient to inhibit tumor growth. As can be seen from size of the tumors in individual mice (FIG. 38B), inhibition of tumor growth was consistent among all mice in the groups.

Figure 39:
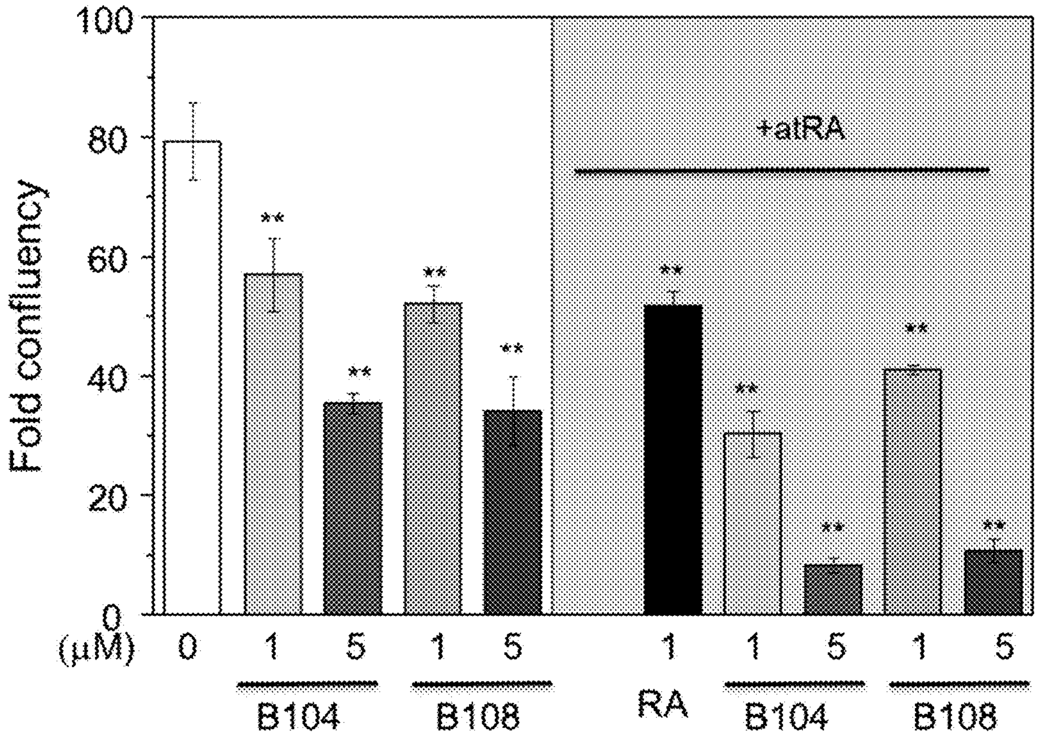
FIG. 39 shows FABP4/5 inhibitors B104, B108, B116, and B118 inhibit growth of neuroblastoma and sensitize cells to all-trans retinoic acid treatments. NPG human neuroblastoma cells were treated with either B104 or B108 at indicated concentrations in the presence or absence of retinoic acid (1 mM) for 4 days. Cells confluency was measured using Incucyte software.

D. Compounds B104 and B108 Suppress Growth of Neuroblastoma (NB) Cells More and Increase Sensitivity to all-Trans Retinoic Acid (atRA) Treatment in Combination Treatments When available in the cell, FABP5 was shown to bind atRA, deliver it to PPARδ and activate the nuclear receptor. Activation of PPARβ by atRA shifts the signaling of this vitamin from its cognate receptor RAR that is known to have anti-carcinogenic activities in multiple cancers to the pro-carcinogenic PPARβ. Hence, inhibition of FABP5 is expected to sensitize cancer cells to atRA by shifting their signaling back to RAR. Accordingly, NB, human NPG cells were used to test the effect of FABP5 inhibitors on cells' proliferation in combination with atRA. Cells were treated with either B104 or B108 in the presence or absence of atRA. Treatment of the cells with B104 and B108 significantly inhibited proliferation of the cells, a trend that was enhanced when the compounds were combined with atRA (FIG. 39).

Figure 40:
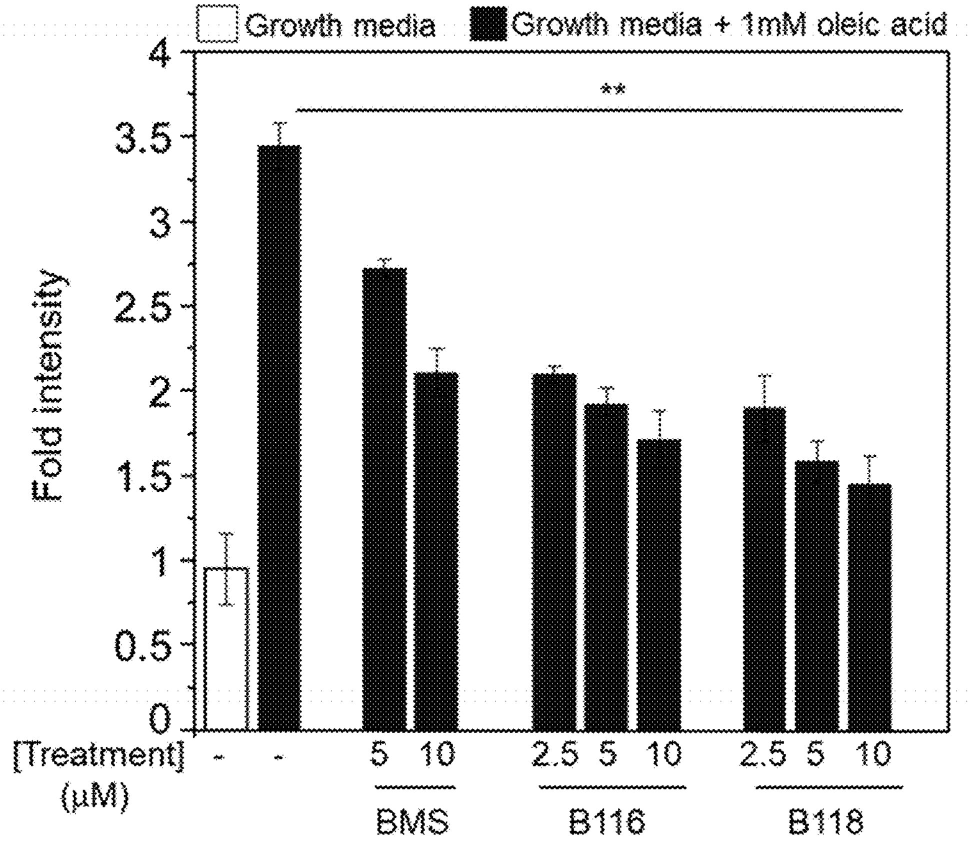
FIG. 40 shows B116 and B118 inhibit lipid uptake in cell culture model of steatosis. Hepatic HepG2 cells were treated with designated concentrations of B116 and B118 for 4 h following by oleic acid treatment (OA) (1 mM, 24 h). Nile Red (green) was used to quantify lipid accumulation and Dapi (blue) was used to identify live cells. Quantification of total lipid uptake was done using Biotech Cytation 5 plate reader.

E. B116 and B118 Inhibit Uptake of Lipids into Hepatocytes in In Vitro Model for Liver Steatosis HepG2 cells were used to test effect of B116 and B118 on uptake of lipid into hepatic cells in an in vitro liver steatosis model. Cells were treated with OA (1 mM) in the presence or absence of the aniline compounds or the known FABP4 inhibitor BMS-309403 (BMS) and lipid accumulation in the cells was quantified using Nile Red. Uptake of lipid into hepatic cells treated with either B116 or B118 was markedly inhibited (FIG. 40). Inhibition of lipid uptake was more efficient by B116 and B188 compared with BMS. For comparison, lipids accumulated in the cells following treatment with 2.5 mM B116 or B118 was comparable to that established after treatment with 10 mM BMS (FIG. 40), indicating the aniline compounds are more efficient than BMS.

F. B4 is Absorbed in Mouse Tissues in Response to Both IP Injections and Oral Administration Male CD-1 mice (n=3) were treated with B4 either by IP injections (5 mg/kg) or by oral gavage (10 mg/kg). At times, 3, 6, and 24 hours after treatment, mice were euthanized and serum, liver, adipose, muscle and brain tissues were collected and analyzed to determine level of B4. Untreated mice were used as controls. As shown by the results summarized in Table 9 (below), B4 was cleared from the serum and tissues after 24 hours but levels of the compounds maintained high in all tissues, except brain, at 6 h. Using oral gavage, levels of B4 observed in the adipose tissue is comparable to that found in the liver even after 6 hours.

TABLE 9

| Administration: Oral Gavage (0.71 μmole/mouse) Drug Concentration | | | |
|---|---|---|---|
| Tissue | 3 hr | 6 hr | 24 hr |
| Blood (HM) | 1.24 ± 0.25 | 0.98 ± 0.50 | 0.0072 ± 0.002 |
| Liver (μmole/kg) | 8.93 ± 2.2 | 6.47 ± 2.3 | 0.035 ± 0.013 |
| Adipose (μmole/kg) | 1.41 ± 0.002 | 1.38 ± 0.05 | 0.11 ± 0.05 |
| Brain (μmole/kg) | 0.1 ± 0.04 | 0.09 ± 0.04 | 0.0009 ± 0.0007 |
| Muscle (μmole/kg) | 1.33 ± 0.74 | 0.95 ± 0.45 | 0.014 ± 0.018 |
| **Administration: IP Injection (0.35 μmole/mouse) Drug Concentration** | | | |
| Tissue | 3 hr | 6 hr | 24 hr |
| Blood (HM) | 1.91 ± 0.14 | 1.37 ± 0.12 | 0.0054 ± 0.002 |
| Liver (μmole/kg) | 7.05 ± 2.0 | 3.45 ± 1.49 | 0.035 ± 0.016 |
| Adipose (μmole/kg) | 7.98 ± 3.82 | 2.45 ± 1.12 | 0.013 ± 0.006 |
| Brain (μmole/kg) | 0.15 ± 0.04 | 0.09 ± 0.01 | 0.0003 ± 0.0002 |
| Muscle (μmole/kg) | 1.7 ± 0.8 | 1.07 ± 0.8 | 0.008 ± 0.002 |

While the foregoing disclosure of the present invention has been described in some detail by way of example and illustration for purposes of clarity and understanding, this disclosure including the examples, descriptions, and embodiments described herein are for illustrative purposes, are intended to be exemplary, and should not be construed as limiting the present disclosure. It will be clear to one skilled in the art that various modifications or changes to the examples, descriptions, and embodiments described herein can be made and are to be included within the spirit and purview of this disclosure and the appended claims. Further, one of skill in the art will recognize a number of equivalent methods and procedure to those described herein. All such equivalents are to be understood to be within the scope of the present disclosure and are covered by the appended claims.

Additional embodiments of the invention are set forth in the following claims.

The disclosures of all publications, patent applications, patents, or other documents mentioned herein are expressly incorporated by reference in their entirety for all purposes to the same extent as if each such individual publication, patent, patent application or other document were individually specifically indicated to be incorporated by reference herein in its entirety for all purposes and were set forth in its entirety herein. In case of conflict, the present specification, including specified terms, will control.

What is claimed is:

1. A compound of structural formula I:

(I)

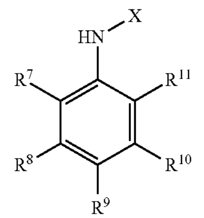

wherein $R^8$ and $R^{11}$ is each independently selected from hydrogen or a substitution for hydrogen, wherein at least one of $R^8$ and $R^{11}$ is a hydrogen, $R^7$, $R^9$, and $R^{10}$ is each an independently selected substitution for hydrogen, wherein at least one of $R^7$ and $R^9$ is halogen;

wherein X has the formula:

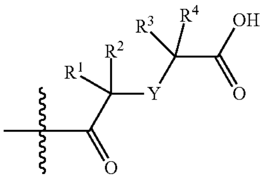

wherein Y is —S—;

wherein $R^1$, $R^2$, $R^3$ and $R^4$ is each independently selected from hydrogen, $C_1$-$C_4$ linear or branched alkyl, phenyl, and benzyl, $R^1$ and $R^4$ can be taken together to form a carbocyclic or heterocyclic ring containing from 5 to 6 atoms;

or a pharmaceutically acceptable salt thereof, with the proviso that:

when $R^1$, $R^2$, $R^3$, $R^4$, $R^8$, and $R^{11}$ are hydrogen, and $R^7$ and $R^9$ are Cl, then $R^{10}$ is not hydrogen, isopropoxy, benzyloxy, prop-2-yn-1-yloxy, methoxy, 2-methoxy-ethoxy, 2-ethoxy-2-oxoethoxy.

2. The compound according to claim 1, wherein $R^1$, $R^2$, $R^3$ and $R^4$ are each independently hydrogen or $C_1$-$C_4$ linear or branched alkyl.

3. The compound according to claim 1, wherein X has a formula selected from:

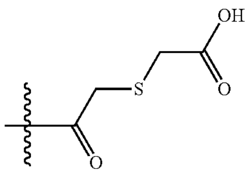

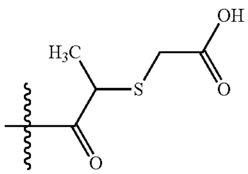 ;

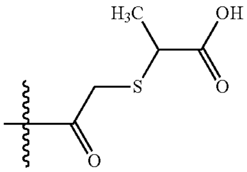 ;

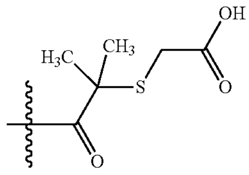 ;

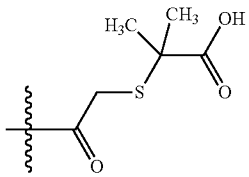 ;

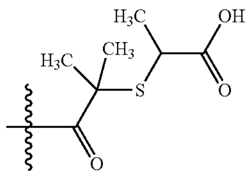 ;

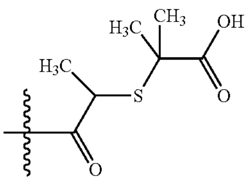 ; and

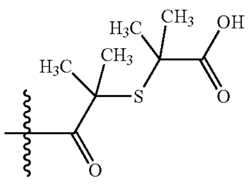 .

4. The compound according to claim 1, wherein X has a formula selected from:

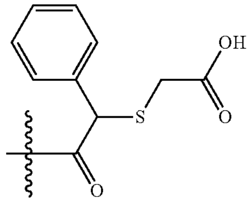 ;

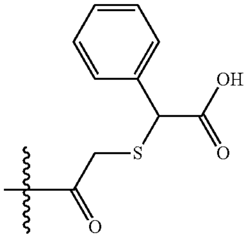 ; and

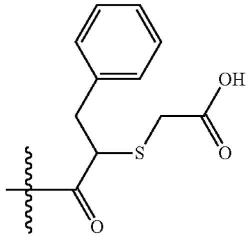 .

5. The compound according to claim 1, wherein X has a formula selected from:

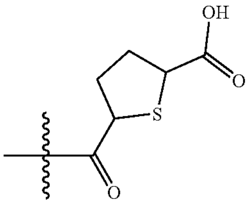 and

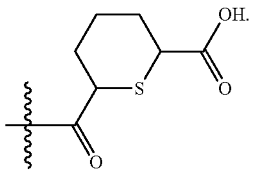

6. The compound according to claim 1, wherein each independently selected substitution for hydrogen is selected from:

i) halogen;

ii) $C_1$-$C_4$ linear or branched, saturated or unsaturated alkyl;

iii) $C_1$-$C_4$ linear or branched, saturated or unsaturated alkoxy;

iv) $—(CR^{12a}R^{12b})_qOR^{13}$;

v) $—(CR^{12a}R^{12b})_qC(O)R^{13}$;

vi) $—(CR^{12a}R^{12b})_qC(O)OR^{13}$;

vii) $—O(CR^{12a}R^{12b})_qC(O)OR^{13}$;

viii) $—(CR^{12a}R^{12b})_qN(R^{13})_2$;

ix) $—CH_mX_n$; wherein X is halogen, m is from 0 to 2, m+n=3;

x) $—(CR^{12a}R^{12b})_qCN$; and xi) $—(CR^{12a}R^{12b})_qNO_2$;

wherein $R^{13}$ is independently hydrogen, $C_1$-$C_4$ linear or branched alkyl, phenyl, or benzyl; and wherein $R^{12a}$ and $R^{12b}$ are each independently hydrogen, methyl ($C_1$), or ethyl ($C_2$) and the index q is an integer from 0 to 4.

7. The compound according to claim 1, wherein each independently selected substitution for hydrogen at $R^1$, $R^8$, $R^9$, $R^{10}$, or $R^{11}$ is selected from halogen, $C_1$-$C_4$ linear, branched, or cyclic, saturated or unsaturated alkyl, phenyl, benzyl, substituted or unsubstituted $C_1$-$C_4$ linear, branched, or cyclic, saturated or unsaturated alkoxy, phenoxy, or benzyloxy.

8. The compound according to claim 1, wherein each independently selected substitution for hydrogen at $R^7$, $R^8$, $R^9$, $R^{10}$, or $R^{11}$ is selected from chloro, methoxy, ethoxy, propoxy, isopropoxy, cyclopropoxy, propargyloxy, butoxy, iso-butoxy, sec-butoxy, tert-butoxy, 2-methoxyethoxy, 2-ethoxy-2-oxoethoxy, or benzyloxy.

9. The compound according to claim 1, wherein the compound is selected from:

i) 2-((2-((2,4-dichloro-5-ethoxyphenyl)amino)-2-oxoethyl)thio)acetic acid;

ii) 2-((2-((2,4-dichloro-5-propoxyphenyl)amino)-2-oxoethyl)thio)acetic acid;

iii) 2-((2-((2,4-dichloro-5-isobutoxyphenyl)amino)-2-oxoethyl)thio)acetic acid;

iv) 2-((2-((5-(tert-butoxy)-2,4-dichlorophenyl)amino)-2-oxoethyl)thio)acetic acid;

v) 2-((2-((2,4-dichloro-5-cyclopropoxyphenyl)amino)-2-oxoethyl)thio)acetic acid;

vi) 2-((2-((2,4-dichloro-5-isopropoxyphenyl)amino)-2-oxoethyl)thio)propanoic acid;

vii) 2-((2-((2,4-dichloro-5-isopropoxyphenyl)amino)-2-oxoethyl)thio)-2-methyl-propanoic acid;

viii) 2-((1-((2,4-dichloro-5-isopropoxyphenyl)amino)-1-oxopropan-2-yl)thio)-propanoic acid;

and ix) 5-((2,4-dichloro-5-isopropoxyphenyl)carbamoyl)tetrahydrothiophene-2-carboxylic acid.

10. A compound of the structure:

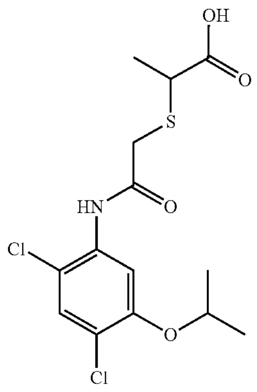 [SMILES: CC(C)Oc1cc(NC(=O)CSC(C)C(=O)O)c(Cl)cc1Cl]

or a pharmaceutically acceptable salt thereof.

11. A compound of the structure:

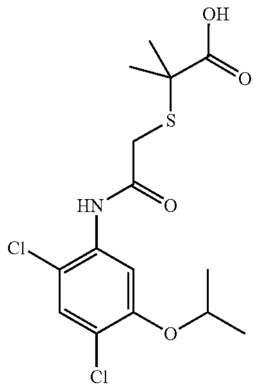 [SMILES: CC(C)Oc1cc(NC(=O)CSC(C)(C)C(=O)O)c(Cl)cc1Cl]

or a pharmaceutically acceptable salt thereof.

* * * * *